US011981942B2

(12) United States Patent
Romero Millan et al.

(10) Patent No.: US 11,981,942 B2
(45) Date of Patent: *May 14, 2024

(54) XYLANASES FOR SOLUBILIZING ARABINOXYLAN-CONTAINING MATERIAL

(71) Applicant: International N&H Denmark Aps, Kongens Lyngby (DK)

(72) Inventors: Luis Fernando Romero Millan, Wilshire (GB); Susan Arent Lund, Brabrand (DK); Brian Soegaard Laursen, Kalundborg (DK); Elijah Gituanjah Kiarie, Waukesha, WI (US); Zhenghong Zhang, Shanghai (CN); Rosalyn Lau, Shanghai (CN); Zheyong Yu, Shanghai (CN); Floor Klaaske Kooy, Leiden (NL); Jan Hendrik Van Tuijl, Zoetermeer (NL); Bart Christiaan Koops, Pijnacker (NL); Mads Brogger Pedersen, Frederiksberg (DK); Soren Dalsgaard, Silkeborg (DK)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,173

(22) Filed: Sep. 1, 2022

(65) Prior Publication Data

US 2023/0093634 A1 Mar. 23, 2023

Related U.S. Application Data

(60) Division of application No. 16/839,897, filed on Apr. 3, 2020, now abandoned, which is a division of
(Continued)

(30) Foreign Application Priority Data

Jul. 23, 2013 (CN) .......................... 201310311358.1

(51) Int. Cl.
  *C12N 9/24* (2006.01)
  *A23K 10/10* (2016.01)
  (Continued)

(52) U.S. Cl.
  CPC ............ *C12N 9/2482* (2013.01); *A23K 10/10* (2016.05); *A23K 10/14* (2016.05); *A23K 10/38* (2016.05);
  (Continued)

(58) Field of Classification Search
  CPC ................................. C12N 9/2482; C12P 7/10
  See application file for complete search history.

(56) References Cited

U.S. PATENT DOCUMENTS

| 4,683,202 A | 7/1987 | Mullis |
| 5,612,055 A | 3/1997 | Bedford et al. |

(Continued)

FOREIGN PATENT DOCUMENTS

| EP | 0238023 B1 | 12/1993 |
| WO | 1991017243 | 11/1991 |

(Continued)

OTHER PUBLICATIONS

Fransceus. J Ind Microbiol Biotechnol. May 2017;44(4-5):687-695.*

(Continued)

*Primary Examiner* — Yong D Pak

(57) ABSTRACT

The present invention relates to a method for solubilising arabinoxylan-containing material (particularly insoluble arabinoxylan-containing material), comprising admixing a xylan-containing material with a xylanase comprising a polypeptide sequence shown herein as SEQ ID No. 3, SEQ ID No. 2, SEQ ID No. 1, SEQ ID No. 9, SEQ ID No. 10. SEQ ID No. 11 or SEQ ID No. 15, or a variant, homologue, fragment or derivative thereof having at least 75% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9, SEQ ID No. 10. SEQ ID No. 11 or SEQ ID No. 15 with a conservative substitution of at least one of the amino acids; or a xylanase which is encoded by a nucleotide sequence shown herein as SEQ ID No. 6, SEQ ID No. 5, SEQ ID No. 4, SEQ ID No. 12. SEQ ID No. 13. SEQ ID No. 14. SEQ ID No. 16. SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14. SEQ ID No. 16. SEQ ID No. 17 or SEQ ID No. 18 under high stringency conditions, or a nucleotide sequence which has at least 75% identity with SEQ ID No. 6, SEQ ID No. 5, SEQ ID No. 4, SEQ ID No. 12, SEQ ID No. 13, SEQ ID No. 14, SEQ ID No. 16. SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides*. The present invention also relates to a novel xylanase comprising (or consisting of) a polypeptide sequence shown herein as SEQ ID No. 3, SEQ ID No. 2 or SEQ ID No. 1, or a variant, homologue, fragment or derivative thereof having at least 99% identity with SEQ ID No. 3 or SEQ ID No. 2 or SEQ ID No. 1; or a xylanase which is encoded by a nucleotide sequence shown herein as SEQ ID No. 6, SEQ ID No. 5 or SEQ ID No. 4, or a nucleotide sequence which can hybridize to SEQ ID No. 4 or SEQ ID No. 5 under high stringency conditions, or a nucleotide sequence which has at least 97.7% identity (preferably 98%

(Continued)

identity) with SEQ ID No. 6, SEQ ID No. 5 or SEQ ID No. 4. The present invention yet further relates to methods relating to feedstuffs, malting and brewing, processing of grain-based materials such as during the production of bioethanol or biochemical (e.g. bio-based isopropanol), or wheat gluten-starch separation processes and the like.

12 Claims, 27 Drawing Sheets

Specification includes a Sequence Listing.

Related U.S. Application Data application No. 15/843,023, filed on Dec. 15, 2017, now Pat. No. 10,612,014, which is a continuation of application No. 14/418,900, filed as application No. PCT/EP2013/066255 on Aug. 2, 2013, now abandoned.

(51) Int. Cl.

| | | |
|---|---|---|
| *A23K 10/14* | (2016.01) | |
| *A23K 10/38* | (2016.01) | |
| *A23K 50/30* | (2016.01) | |
| *A23K 50/75* | (2016.01) | |
| *C12C 5/00* | (2006.01) | |
| *C12P 5/00* | (2006.01) | |
| *C12P 7/10* | (2006.01) | |
| *C12P 19/14* | (2006.01) | |
| *C13K 1/02* | (2006.01) | |
| *C13K 1/06* | (2006.01) | |

(52) U.S. Cl.
CPC .............. *A23K 50/30* (2016.05); *A23K 50/75* (2016.05); *C12C 5/004* (2013.01); *C12P 5/007* (2013.01); *C12P 7/10* (2013.01); *C12P 19/14* (2013.01); *C12Y 302/01008* (2013.01); *C13K 1/02* (2013.01); *C13K 1/06* (2013.01); *Y02E 50/10* (2013.01); *Y02P 60/87* (2015.11)

(56) References Cited

U.S. PATENT DOCUMENTS

| | | |
|---|---|---|
| 6,768,001 B2 | 7/2004 | Saloheimo et al. |
| 7,320,876 B2 | 1/2008 | Webel et al. |
| 7,504,120 B2 | 3/2009 | Steer et al. |
| 10,165,787 B2 | 1/2019 | Lorentsen et al. |
| 10,253,304 B2 | 4/2019 | Lorentsen et al. |
| 2015/0216203 A1 | 8/2015 | Isaksen et al. |
| 2015/0337247 A1 | 11/2015 | Sorensen et al. |

FOREIGN PATENT DOCUMENTS

| | | |
|---|---|---|
| WO | 1992012645 | 8/1992 |
| WO | 1997016076 | 5/1997 |
| WO | 2005001036 A2 | 1/2005 |
| WO | 2007044968 A2 | 4/2007 |
| WO | 2007095398 A2 | 8/2007 |
| WO | 2009108941 A2 | 9/2009 |

OTHER PUBLICATIONS

Sanavia. Computational and Structural Biotechnology Journal, vol. 18, 2020, pp. 1968-1979.*
Ravn. Combined endo-β-1,4-xylanase and α-I-arabinofuranosidase increases butyrate concentration during broiler cecal fermentation of maize glucurono-arabinoxylan, Animal Feed Science and Technology, vol. 236, 2018, pp. 159-169.*
Studer. Residue mutations and their impact on protein structure and function: detecting beneficial and pathogenic changes. Biochem. J. (2013) 449, 581-594.*
EWG55328.1 GenBank Database. 2014.*
Courtin (Relative Activity of Endoxylanases Towards Water-extractable and Water-unextractable Arabinoxylan. Journal of Cereal Science, vol. 33, Issue 3, 2001, pp. 301-331.*
International Search Report, PCT International Application PCT/EP2013/066255 dated Nov. 22, 2013, 8 pages.
Ravalason et al., "Secretome as a Source of Auxiliary Enzymes to Enhance Saccharification of Wheat Straw", Bioresource Technology, vol. 114 (2012), pp. 589-596.
Correia et al., "Structure and Function of an Arabinoxylan-Specific Xylanase", Journal of Biological Chemistry, vol. 286, No. 25 (2011 ), pp. 22510-22520.
Saha et al., "Hemicellulose Bioconversation", J. Ind. Microbiol. Biotechnol., vol. 30 (2003), pp. 279-291.
Jaroszuk-Scisel et al., "Hydrolysis of Fungal and Plant Cell Walls by Eniymatic Complexes From Cultures of Isolates With Different Aggressiveness to Rye", Archives of Microbiology, vol. 194, No. 8 (2012), pp. 653-665.
Ruiz-Roldan et al., "Two xylanase genes of the vascular wilt pathogen Fusarium oxysporum are differentially expressed during infection of tomato plants", Mol. Gen. Genet., Apr. 1999, vol. 261, No. 3, pp. 530-536.
Branden et al., Introduction to Protein Structure, Garland Publishing Inc., New York, p. 247, 1991.

* cited by examiner

FIGURE 1

(SEQ ID NO. 1)

<u>mklssflytaslvaa</u>*IPTAIEPR*QAADSINKLIKNKGKLYYGTITDPNLLGVAKDTAIIKADFGAVTPEN
SGKWDATEPSQGKFNFGSFDQVVNFAQQNGLKVRGHTLVWHSQLPQWVKNINDKATLTK
VIENHVTQVVGRYKGKIYAWDVVNEIFEWDGTLRKDSHFNNVFGNDDYVGIAFRAARKADP
NAKLYINDYSLDSGSASKVTKGMVPSVKKWLSQGVPVDGIGSQTHLDPGAAGQIQGALTAL
ANSGVKEVAITELDIRTAPANDYATVTKACLNVPKCIGITVWGVSDKNSWRKEHDSLLFDAN
YNPKPAYTAVVNALR

FIGURE 2

(SEQ ID No. 2)

*IPTAIEPR*QAADSINKLIKNKGKLYYGTITDPNLLGVAKDTAIIKADFGAVTPENSGKWDATEP
SQGKFNFGSFDQVVNFAQQNGLKVRGHTLVWHSQLPQWVKNINDKATLTKVIENHVTQVV
GRYKGKIYAWDVVNEIFEWDGTLRKDSHFNNVFGNDDYVGIAFRAARKADPNAKLYINDYS
LDSGSASKVTKGMVPSVKKWLSQGVPVDGIGSQTHLDPGAAGQIQGALTALANSGVKEVAI
TELDIRTAPANDYATVTKACLNVPKCIGITVWGVSDKNSWRKEHDSLLFDANYNPKPAYTAV
VNALR

FIGURE 3

(SEQ ID No. 3)

QAADSINKLIKNKGKLYYGTITDPNLLGVAKDTAIIKADFGAVTPENSGKWDATEPSQGKFNF
GSFDQVVNFAQQNGLKVRGHTLVWHSQLPQWVKNINDKATLTKVIENHVTQVVGRYKGKIY
AWDVVNEIFEWDGTLRKDSHFNNVFGNDDYVGIAFRAARKADPNAKLYINDYSLDSGSASK
VTKGMVPSVKKWLSQGVPVDGIGSQTHLDPGAAGQIQGALTALANSGVKEVAITELDIRTAP
ANDYATVTKACLNVPKCIGITVWGVSDKNSWRKEHDSLLFDANYNPKPAYTAVVNALR

FIGURE 4

(SEQ ID NO. 4)

ATGAAGCTGTCTTCTTTCCTCTACACCGCCTCGCTGGTCGCGGCCATTCCCACCGCCA
TCGAGCCCCGCCAGGCTGCCGACAGCATCAACAAGCTGATCAAGAACAAGGGCAAGCT
CTACTACGGAACCATCACCGACCCCAACCTGCTCGGCGTCGCAAAGGACACCGCCATC
ATCAAGGCCGACTTTGGCGCCGTTACCCCCGAGAACTCGGGCAAGTGGGACGCCACC
GAGCCCAGCCAGGGCAAGTTCAACTTCGGTAGCTTCGACCAGGTTGTCAACTTTGCCC
AGCAGAATGGCCTCAAGGTCCGAGGTCACACTCTGGTCTGGCACTCTCAGCTCCCTCA
GTGGGTTAAGAACATCAACGACAAGGCTACTCTGACCAAGGTCATTGAGAACCACGTCA
CCCAAGTCGTTGGACGCTACAAGGGCAAGATCTACGCCTGG*gtatgttttattcccccagacttctt*
*cgaaatgactttgctaacatgttcag*GACGTCGTCAACGAGATCTTCGAGTGGGACGGTACCCTCC
GAAAGGACTCTCACTTCAACAACGTCTTCGGCAACGACGACTACGTTGGCATTGCCTTC
CGCGCCGCCCGCAAGGCTGACCCCAACGCCAAGCTGTACATCAACGACTACAGCCTCG
ACTCCGGCAGCGCCTCCAAGGTCACCAAGGGTATGGTTCCCTCCGTCAAGAAGTGGCT
CAGCCAGGGCGTTCCCGTCGACGGCATTGGCTCTCAGACTCACCTTGACCCCGGTGCC
GCTGGCCAAATCCAGGGTGCTCTCACTGCCCTCGCCAATTCTGGTGTCAAGGAGGTTG
CCATCACCGAGCTCGACATCCGCACTGCCCCGCCAACGACTACGCTACCGTCACCAA
GGCCTGCCTCAACGTCCCCAAGTGCATTGGTATCACCGTCTGGGGTGTCTCTGACAAG
AACTCTTGGCGCAAGGAGCACGACAGTCTTCTGTTCGATGCTAACTACAACCCCAAGCC
TGCTTACACTGCTGTTGTCAACGCTCTCCGCTAA

FIGURE 5

(SEQ ID NO. 5)

ATGAAGCTGTCTTCTTTCCTCTACACCGCCTCGCTGGTCGCGGCCATTCCCACCGCCA
TCGAGCCCCGCCAGGCTGCCGACAGCATCAACAAGCTGATCAAGAACAAGGGCAAGCT
CTACTACGGAACCATCACCGACCCCAACCTGCTCGGCGTCGCAAAGGACACCGCCATC
ATCAAGGCCGACTTTGGCGCCGTTACCCCCGAGAACTCGGGCAAGTGGGACGCCACC
GAGCCCAGCCAGGGCAAGTTCAACTTCGGTAGCTTCGACCAGGTTGTCAACTTTGCCC
AGCAGAATGGCCTCAAGGTCCGAGGTCACACTCTGGTCTGGCACTCTCAGCTCCCTCA
GTGGGTTAAGAACATCAACGACAAGGCTACTCTGACCAAGGTCATTGAGAACCACGTCA
CCCAAGTCGTTGGACGCTACAAGGGCAAGATCTACGCCTGGGACGTCGTCAACGAGAT
CTTCGAGTGGGACGGTACCCTCCGAAAGGACTCTCACTTCAACAACGTCTTCGGCAAC
GACGACTACGTTGGCATTGCCTTCCGCGCCGCCCGCAAGGCTGACCCCAACGCCAAGC
TGTACATCAACGACTACAGCCTCGACTCCGGCAGCGCCTCCAAGGTCACCAAGGGTAT
GGTTCCCTCCGTCAAGAAGTGGCTCAGCCAGGGCGTTCCCGTCGACGGCATTGGCTCT
CAGACTCACCTTGACCCCGGTGCCGCTGGCCAAATCCAGGGTGCTCTCACTGCCCTCG
CCAATTCTGGTGTCAAGGAGGTTGCCATCACCGAGCTCGACATCCGCACTGCCCCGC
CAACGACTACGCTACCGTCACCAAGGCCTGCCTCAACGTCCCCAAGTGCATTGGTATCA
CCGTCTGGGGTGTCTCTGACAAGAACTCTTGGCGCAAGGAGCACGACAGTCTTCTGTT
CGATGCTAACTACAACCCCAAGCCTGCTTACACTGCTGTTGTCAACGCTCTCCGCTAA

FIGURE 6

(SEQ ID NO. 6)

ATTCCCACCGCCATCGAGCCCCGCCAGGCTGCCGACAGCATCAACAAGCTGATCAAGA
ACAAGGGCAAGCTCTACTACGGAACCATCACCGACCCCAACCTGCTCGGCGTCGCAAA
GGACACCGCCATCATCAAGGCCGACTTTGGCGCCGTTACCCCCGAGAACTCGGGCAAG
TGGGACGCCACCGAGCCCAGCCAGGGCAAGTTCAACTTCGGTAGCTTCGACCAGGTTG
TCAACTTTGCCCAGCAGAATGGCCTCAAGGTCCGAGGTCACACTCTGGTCTGGCACTCT
CAGCTCCCTCAGTGGGTTAAGAACATCAACGACAAGGCTACTCTGACCAAGGTCATTGA
GAACCACGTCACCCAAGTCGTTGGACGCTACAAGGGCAAGATCTACGCCTGGGACGTC
GTCAACGAGATCTTCGAGTGGGACGGTACCCTCCGAAAGGACTCTCACTTCAACAACGT
CTTCGGCAACGACGACTACGTTGGCATTGCCTTCCGCGCCGCCCGCAAGGCTGACCCC
AACGCCAAGCTGTACATCAACGACTACAGCCTCGACTCCGGCAGCGCCTCCAAGGTCA
CCAAGGGTATGGTTCCCTCCGTCAAGAAGTGGCTCAGCCAGGGCGTTCCCGTCGACGG
CATTGGCTCTCAGACTCACCTTGACCCCGGTGCCGCTGGCCAAATCCAGGGTGCTCTC
ACTGCCCTCGCCAATTCTGGTGTCAAGGAGGTTGCCATCACCGAGCTCGACATCCGCA
CTGCCCCCGCCAACGACTACGCTACCGTCACCAAGGCCTGCCTAACGTCCCCAAGTG
CATTGGTATCACCGTCTGGGGTGTCTCTGACAAGAACTCTTGGCGCAAGGAGCACGAC
AGTCTTCTGTTCGATGCTAACTACAACCCCAAGCCTGCTTACACTGCTGTTGTCAACGCT
CTCCGCTAA

FIGURE 15

(SEQ ID No. 9)

mklssflytaslvaa*IPTAIEPR*QASDSINKLIKNKGKLYYGTITDPNLLGVAKDTAIIKADFGAVTPEN
SGKWDATEPSQGKFNFGSFDQVVNFAQQNGLKVRGHTLVWHSQLPQWVKNINDKATLTK
VIENHVTNVVGRYKGKIYAWDVVNEIFDWDGTLRKDSHFNNVFGNDDYVGIAFRAARKADP
NAKLYINDYSLDSGSASKVTKGMVPSVKKWLSQGVPVDGIGSQTHLDPGAAGQIQGALTAL
ANSGVKEVAITELDIRTAPANDYATVTKACLNVPKCIGITVWGVSDKNSWRKEHDSLLFDAN
YNPKAAYTAVVNALR

FIGURE 16

(SEQ ID No. 10)

*IPTAIEPR*QASDSINKLIKNKGKLYYGTITDPNLLGVAKDTAIIKADFGAVTPENSGKWDATEP
SQGKFNFGSFDQVVNFAQQNGLKVRGHTLVWHSQLPQWVKNINDKATLTKVIENHVTNVV
GRYKGKIYAWDVVNEIFDWDGTLRKDSHFNNVFGNDDYVGIAFRAARKADPNAKLYINDYS
LDSGSASKVTKGMVPSVKKWLSQGVPVDGIGSQTHLDPGAAGQIQGALTALANSGVKEVAI
TELDIRTAPANDYATVTKACLNVPKCIGITVWGVSDKNSWRKEHDSLLFDANYNPKAAYTAV
VNALR

FIGURE 17

(SEQ ID No. 11)

QASDSINKLIKNKGKLYYGTITDPNLLGVAKDTAIIKADFGAVTPENSGKWDATEPSQGKFNF
GSFDQVVNFAQQNGLKVRGHTLVWHSQLPQWVKNINDKATLTKVIENHVTNVVGRYKGKIY
AWDVVNEIFDWDGTLRKDSHFNNVFGNDDYVGIAFRAARKADPNAKLYINDYSLDSGSASK
VTKGMVPSVKKWLSQGVPVDGIGSQTHLDPGAAGQIQGALTALANSGVKEVAITELDIRTAP
ANDYATVTKACLNVPKCIGITVWGVSDKNSWRKEHDSLLFDANYNPKAAYTAVVNALR

FIGURE 19

SEQ ID No. 12

ATGAAGCTGTCTTCCTTCCTCTACACCGCCTCGCTGGTCGCGGCCATTCCCACCGCCA
TCGAGCCCCGCCAGGCCTCCGACAGCATCAACAAGCTGATCAAGAACAAGGGCAAGCT
CTACTACGGAACCATCACCGACCCCAACCTGCTCGGCGTCGCAAAGGACACTGCCATC
ATCAAGGCTGACTTTGGCGCCGTCACACCCGAGAACTCGGGTAAGTGGGATGCCACCG
AGCCCAGCCAGGGCAAGTTCAACTTCGGCAGCTTCGACCAGGTCGTCAACTTTGCTCA
GCAGAATGGCCTCAAGGTCCGAGGTCACACTCTAGTCTGGCACTCCCAGCTCCCTCAG
TGGGTTAAGAACATCAACGACAAGGCTACTTTGACCAAGGTCATCGAGAACCACGTCAC
CAACGTCGTTGGACGCTACAAGGGCAAGATCTACGCCTGG*gtatgttttcttcactcgaacttcttataaa*
*tggctttactaacatgttcag*GACGTCGTTAACGAGATCTTCGACTGGGATGGTACCCTCCGAAAG
GACTCTCACTTCAACAACGTCTTCGGCAACGACGACTACGTTGGCATTGCCTTCCGCGC
TGCCCGCAAGGCTGACCCCAACGCCAAGCTGTACATCAACGACTACAGCCTCGACTCC
GGCAGCGCCTCCAAGGTCACCAAGGGCATGGTTCCCTCTGTCAAGAAGTGGCTCAGCC
AGGGCGTCCCCGTCGACGGTATTGGTTCTCAGACTCACCTTGACCCCGGTGCCGCTGG
CCAAATCCAGGGTGCTCTCACTGCCCTCGCCAACTCTGGTGTGAAGGAGGTTGCCATC
ACCGAGCTCGACATCCGCACTGCCCCCGCCAACGACTACGCTACCGTTACCAAGGCCT
GCCTCAACGTCCCCAAGTGCATTGGTATCACCGTCTGGGGCGTATCTGACAAGAACTCT
TGGCGCAAGGAGCACGACAGCCTTCTGTTCGATGCTAACTACAACCCCAAGGCTGCTTA
CACTGCTGTTGTCAACGCTCTCCGCTAA

FIGURE 20

SEQ ID No. 13

ATGAAGCTGTCTTCCTTCCTCTACACCGCCTCGCTGGTCGCGGCCATTCCCACCGCCA
TCGAGCCCCGCCAGGCCTCCGACAGCATCAACAAGCTGATCAAGAACAAGGGCAAGCT
CTACTACGGAACCATCACCGACCCCAACCTGCTCGGCGTCGCAAAGGACACTGCCATC
ATCAAGGCTGACTTTGGCGCCGTCACACCCGAGAACTCGGGTAAGTGGGATGCCACCG
AGCCCAGCCAGGGCAAGTTCAACTTCGGCAGCTTCGACCAGGTCGTCAACTTTGCTCA
GCAGAATGGCCTCAAGGTCCGAGGTCACACTCTAGTCTGGCACTCCCAGCTCCCTCAG
TGGGTTAAGAACATCAACGACAAGGCTACTTTGACCAAGGTCATCGAGAACCACGTCAC
CAACGTCGTTGGACGCTACAAGGGCAAGATCTACGCCTGGGACGTCGTTAACGAGATC
TTCGACTGGGATGGTACCCTCCGAAAGGACTCTCACTTCAACAACGTCTTCGGCAACGA
CGACTACGTTGGCATTGCCTTCCGCGCTGCCCGCAAGGCTGACCCCAACGCCAAGCTG
TACATCAACGACTACAGCCTCGACTCCGGCAGCGCCTCCAAGGTCACCAAGGGCATGG
TTCCCTCTGTCAAGAAGTGGCTCAGCCAGGGCGTCCCCGTCGACGGTATTGGTTCTCA
GACTCACCTTGACCCCGGTGCCGCTGGCCAAATCCAGGGTGCTCTCACTGCCCTCGCC
AACTCTGGTGTGAAGGAGGTTGCCATCACCGAGCTCGACATCCGCACTGCCCCCGCCA
ACGACTACGCTACCGTTACCAAGGCCTGCCTCAACGTCCCCAAGTGCATTGGTATCACC
GTCTGGGGCGTATCTGACAAGAACTCTTGGCGCAAGGAGCACGACAGCCTTCTGTTCG
ATGCTAACTACAACCCCAAGGCTGCTTACACTGCTGTTGTCAACGCTCTCCGCTAA

FIGURE 21

SEQ ID No. 14

ATTCCCACCGCCATCGAGCCCCGCCAGGCCTCCGACAGCATCAACAAGCTGATCAAGA
ACAAGGGCAAGCTCTACTACGGAACCATCACCGACCCCAACCTGCTCGGCGTCGCAAA
GGACACTGCCATCATCAAGGCTGACTTTGGCGCCGTCACACCCGAGAACTCGGGTAAG
TGGGATGCCACCGAGCCCAGCCAGGGCAAGTTCAACTTCGGCAGCTTCGACCAGGTCG
TCAACTTTGCTCAGCAGAATGGCCTCAAGGTCCGAGGTCACACTCTAGTCTGGCACTCC
CAGCTCCCTCAGTGGGTTAAGAACATCAACGACAAGGCTACTTTGACCAAGGTCATCGA
GAACCACGTCACCAACGTCGTTGGACGCTACAAGGGCAAGATCTACGCCTGGGACGTC
GTTAACGAGATCTTCGACTGGGATGGTACCCTCCGAAAGGACTCTCACTTCAACAACGT
CTTCGGCAACGACGACTACGTTGGCATTGCCTTCCGCGCTGCCCGCAAGGCTGACCCC
AACGCCAAGCTGTACATCAACGACTACAGCCTCGACTCCGGCAGCGCCTCCAAGGTCA
CCAAGGGCATGGTTCCCTCTGTCAAGAAGTGGCTCAGCCAGGGCGTCCCCGTCGACG
GTATTGGTTCTCAGACTCACCTTGACCCCGGTGCCGCTGGCCAAATCCAGGGTGCTCT
CACTGCCCTCGCCAACTCTGGTGTGAAGGAGGTTGCCATCACCGAGCTCGACATCCGC
ACTGCCCCGCCAACGACTACGCTACCGTTACCAAGGCCTGCCTCAACGTCCCCAAGT
GCATTGGTATCACCGTCTGGGGCGTATCTGACAAGAACTCTTGGCGCAAGGAGCACGA
CAGCCTTCTGTTCGATGCTAACTACAACCCCAAGGCTGCTTACACTGCTGTTGTCAACG
CTCTCCGCTAA

FIGURE 25

SEQ ID No. 15

QAADSINKLIKNKGKLYYGTITDPNLLGVAKDTAVIKADFGAVTPENSGKWDATEPSQGNFN
FGSFDQVVNFAQQNGLKVRGHTLVWHSQLPQWVKNINDKATLTKVIENHVTQVVGRYKGKI
YAWDVVNEIFDWDGTLRKDSHFNNVFGNDDYVGIAFRAARKADPNAKLYINDYSLDSASAS
KVTKGMVPSVKKWLSQGVPVDGIGSQSHLDPGAAGQVQGALTALANSGVKEVAITELDIRT
APANDYATVTKACLNVPKCIGITVWGVSDKNSWRKEHDSLLFDSNYNPKPAYTAVVNALR

FIG. 26

| | 10 | 20 | 30 | 40 | 50 | |
|---|---|---|---|---|---|---|
| SEQ_ID No.3  | QAADSINKLIKNKGKLYYGTITDPNLLGVAKDTAI | IKADFGAVTPENSGKWDAITE | 55 |
| SEQ_ID No.11 | QASDSINKLIKNKGKLYYGTITDPNLLGVAKDTAI | IKADFGAVTPENSGKWDAITE | 55 |
| SEQ_ID No.15 | QAADSINKLIKNKGKLYYGTITDPNLLGVAKDTAV | IKADFGAVTPENSGKWDAITE | 55 |

| | 60 | 70 | 80 | 90 | 100 | 110 | |
|---|---|---|---|---|---|---|---|
| SEQ_ID No.3  | PSQGKFNFIGSFDQVVNFAQQNGLKVRGHTLVWHSQLPQWVKNINDKATLTKVIIEN | 110 |
| SEQ_ID No.11 | PSQGKFNFIGSFDQVVNFAQQNGLKVRGHTLVWHSQLPQWVKNINDKATLTKVIIEN | 110 |
| SEQ_ID No.15 | PSQGNFNFIGSFDQVVNFAQQNGLKVRGHTLVWHSQLPQWVKNINDKATLTKVIIEN | 110 |

| | 120 | 130 | 140 | 150 | 160 | |
|---|---|---|---|---|---|---|
| SEQ_ID No.3  | HVTQVVGRYKGKIYAWDVVNEIFEWDGTLRKDSHFNNVFGNDDYVGIAFRAARKA | 165 |
| SEQ_ID No.11 | HVTNVVGRYKGKIYAWDVVNEIFDWDGTLRKDSHFNNVFGNDDYVGIAFRAARKA | 165 |
| SEQ_ID No.15 | HVTQVVGRYKGKIYAWDVVNEIFDWDGTLRKDSHFNNVFGNDDYVGIAFRAARKA | 165 |

| | 170 | 180 | 190 | 200 | 210 | 220 | |
|---|---|---|---|---|---|---|---|
| SEQ_ID No.3  | DPNAKLYINDYSLDSGSASKVTKGMVPSVKKNLISQGGVPVDGIGSQTHLDPGAAGQ | 220 |
| SEQ_ID No.11 | DPNAKLYINDYSLDSGSASKVTKGMVPSVKKNLISQGGVPVDGIGSQTHLDPGAAGQ | 220 |
| SEQ_ID No.15 | DPNAKLYINDYSLDSASASKVTKGMVPSVKKNLISQGGVPVDGIGSQSHLDPGAAGQ | 220 |

| | 230 | 240 | 250 | 260 | 270 | |
|---|---|---|---|---|---|---|
| SEQ_ID No.3  | IQGALTALANSGVKEVAITELDIRTAPANDYATVTKACLNVPKCIGITVWGVSDK | 275 |
| SEQ_ID No.11 | IQGALTALANSGVKEVAITELDIRTAPANDYATVTKACLNVPKCIGITVWGVSDK | 275 |
| SEQ_ID No.15 | VQGALTALANSGVKEVAITELDIRTAPANDYATVTKACLNVPKCIGITVWGVSDK | 275 |

| | 280 | 290 | 300 | 310 | |
|---|---|---|---|---|---|
| SEQ_ID No.3  | NSWRKEHDSLILFDANYNPKPAYTAVVNALR | 305 |
| SEQ_ID No.11 | NSWRKEHDSLILFDANYNPKAAYTAVVNALR | 305 |
| SEQ_ID No.15 | NSWRKEHDSLILFDSNYNPKPAYTAVVNALR | 305 |

Corn In DDGS:

Wheat In DDGS:

FIGURE 30

(SEQ ID NO. 16)

ATGAAGCTGTCTTCTTTCCTCTACACCGCCTCGCTGGTCGCGGCCATTCCCACCGCCA
TCGAGCCCCGCCAGGCCGCCGACAGCATCAACAAGCTGATCAAGAACAAGGGCAAGCT
CTACTACGGAACCATCACCGACCCCAACCTGCTCGGCGTCGCAAAGGACACCGCCGTC
ATCAAGGCCGACTTTGGCGCCGTCACCCCCGAGAACTCGGGCAAGTGGGACGCCACC
GAGCCCAGCCAGGGCAACTTCAACTTCGGTAGCTTCGACCAGGTCGTCAACTTTGCTCA
GCAGAATGGCCTCAAGGTCCGAGGTCACACTCTGGTCTGGCACTCTCAGCTCCCTCAG
TGGGTTAAGAACATCAACGACAAGGCTACTCTGACCAAGGTCATTGAGAACCACGTCAC
CCAAGTCGTTGGACGCTACAAGGGCAAGATCTACGCCTGGgtatgttttcttgcctcgaccttctca
aagatgaatttgctaacatgttcagGACGTTGTCAACGAGATCTTCGACTGGGACGGTACCCTCCG
AAAGGATTCTCACTTCAACAACGTCTTCGGCAACGATGACTACGTTGGCATTGCCTTCC
GCGCCGCCCGCAAGGCTGACCCCAACGCCAAGCTGTACATCAACGACTACAGCCTCGA
CTCCGCCAGCGCCTCCAAGGTCACCAAGGGCATGGTCCCCTCCGTCAAGAAGTGGCTC
AGCCAGGGCGTTCCCGTCGACGGCATTGGCTCCAGTCTCACCTTGACCCCGGTGCCG
CTGGCCAAGTCCAGGGTGCTCTCACTGCCCTCGCCAACTCTGGTGTCAAGGAGGTTGC
CATCACCGAGCTCGACATCCGCACTGCCCCGCCAACGACTACGCCACCGTCACCAAG
GCCTGCCTAAACGTCCCCAAGTGCATTGGTATCACCGTCTGGGGTGTCTCTGACAAGAA
CTCTTGGCGCAAGGAGCACGACAGCCTTCTGTTCGACTCCAACTACAACCCCAAGCCT
GCTTACACTGCTGTTGTCAACGCTCTCCGCTAA

FIGURE 31

(SEQ ID NO. 17)

ATGAAGCTGTCTTCTTTCCTCTACACCGCCTCGCTGGTCGCGGCCATTCCCACCGCCA
TCGAGCCCCGCCAGGCCGCCGACAGCATCAACAAGCTGATCAAGAACAAGGGCAAGCT
CTACTACGGAACCATCACCGACCCCAACCTGCTCGGCGTCGCAAAGGACACCGCCGTC
ATCAAGGCCGACTTTGGCGCCGTCACCCCCGAGAACTCGGGCAAGTGGGACGCCACC
GAGCCCAGCCAGGGCAACTTCAACTTCGGTAGCTTCGACCAGGTCGTCAACTTTGCTCA
GCAGAATGGCCTCAAGGTCCGAGGTCACACTCTGGTCTGGCACTCTCAGCTCCCTCAG
TGGGTTAAGAACATCAACGACAAGGCTACTCTGACCAAGGTCATTGAGAACCACGTCAC
CCAAGTCGTTGGACGCTACAAGGGCAAGATCTACGCCTGGGACGTTGTCAACGAGATC
TTCGACTGGGACGGTACCCTCCGAAAGGATTCTCACTTCAACAACGTCTTCGGCAACGA
TGACTACGTTGGCATTGCCTTCCGCGCCGCCCGCAAGGCTGACCCCAACGCCAAGCTG
TACATCAACGACTACAGCCTCGACTCCGCCAGCGCCTCCAAGGTCACCAAGGGCATGG
TCCCTCCGTCAAGAAGTGGCTCAGCCAGGGCGTTCCCGTCGACGGCATTGGCTCCCA
GTCTCACCTTGACCCCGGTGCCGCTGGCCAAGTCCAGGGTGCTCTCACTGCCCTCGCC
AACTCTGGTGTCAAGGAGGTTGCCATCACCGAGCTCGACATCCGCACTGCCCCCGCCA
ACGACTACGCCACCGTCACCAAGGCCTGCCTAAACGTCCCCAAGTGCATTGGTATCAC
CGTCTGGGGTGTCTCTGACAAGAACTCTTGGCGCAAGGAGCACGACAGCCTTCTGTTC
GACTCCAACTACAACCCCAAGCCTGCTTACACTGCTGTTGTCAACGCTCTCCGCTAA

FIGURE 32

(SEQ ID NO. 18)

ATTCCCACCGCCATCGAGCCCCGCCAGGCCGCCGACAGCATCAACAAGCTGATCAAGA
ACAAGGGCAAGCTCTACTACGGAACCATCACCGACCCCAACCTGCTCGGCGTCGCAAA
GGACACCGCCGTCATCAAGGCCGACTTTGGCGCCGTCACCCCCGAGAACTCGGGCAA
GTGGGACGCCACCGAGCCCAGCCAGGGCAACTTCAACTTCGGTAGCTTCGACCAGGTC
GTCAACTTTGCTCAGCAGAATGGCCTCAAGGTCCGAGGTCACACTCTGGTCTGGCACTC
TCAGCTCCCTCAGTGGGTTAAGAACATCAACGACAAGGCTACTCTGACCAAGGTCATTG
AGAACCACGTCACCCAAGTCGTTGGACGCTACAAGGGCAAGATCTACGCCTGGGACGT
TGTCAACGAGATCTTCGACTGGGACGGTACCCTCCGAAAGGATTCTCACTTCAACAACG
TCTTCGGCAACGATGACTACGTTGGCATTGCCTTCCGCGCCGCCCGCAAGGCTGACCC
CAACGCCAAGCTGTACATCAACGACTACAGCCTCGACTCCGCCAGCGCCTCCAAGGTC
ACCAAGGGCATGGTCCCCTCCGTCAAGAAGTGGCTCAGCCAGGGCGTTCCCGTCGAC
GGCATTGGCTCCCAGTCTCACCTTGACCCCGGTGCCGCTGGCCAAGTCCAGGGTGCTC
TCACTGCCCTCGCCAACTCTGGTGTCAAGGAGGTTGCCATCACCGAGCTCGACATCCG
CACTGCCCCGCCAACGACTACGCCACCGTCACCAAGGCCTGCCTAAACGTCCCCAAG
TGCATTGGTATCACCGTCTGGGGTGTCTCTGACAAGAACTCTTGGCGCAAGGAGCACG
ACAGCCTTCTGTTCGACTCCAACTACAACCCCAAGCCTGCTTACACTGCTGTTGTCAAC
GCTCTCCGCTAA

SEQUENCE LISTING

```
Sequence total quantity: 20
SEQ ID NO: 1              moltype = AA   length = 328
FEATURE                   Location/Qualifiers
source                    1..328
                          mol_type = protein
                          organism = Fusarium verticillioides
SEQUENCE: 1
MKLSSFLYTA SLVAAIPTAI EPRQAADSIN KLIKNKGKLY YGTITDPNLL GVAKDTAIIK   60
ADFGAVTPEN SGKWDATEPS QGKFNFGSFD QVVNFAQQNG LKVRGHTLVW HSQLPQWVKN  120
INDKATLTKV IENHVTQVVG RYKGKIYAWD VVNEIFEWDG TLRKDSHFNN VFGNDDYVGI  180
AFRAARKADP NAKLYINDYS LDSGSASKVT KGMVPSVKKW LSQGVPVDGI GSQTHLDPGA  240
AGQIQGALTA LANSGVKEVA ITELDIRTAP ANDYATVTKA CLNVPKCIGI TVWGVSDKNS  300
WRKEHDSLLF DANYNPKPAY TAVVNALR                                     328

SEQ ID NO: 2              moltype = AA   length = 313
FEATURE                   Location/Qualifiers
source                    1..313
                          mol_type = protein
                          organism = Fusarium verticillioides
SEQUENCE: 2
IPTAIEPRQA ADSINKLIKN KGKLYYGTIT DPNLLGVAKD TAIIKADFGA VTPENSGKWD   60
ATEPSQGKFN FGSFDQVVNF AQQNGLKVRG HTLVWHSQLP QWVKNINDKA TLTKVIENHV  120
TQVVGRYKGK IYAWDVVNEI FEWDGTLRKD SHFNNVFGND DYVGIAFRAA RKADPNAKLY  180
INDYSLDSGS ASKVTKGMVP SVKKWLSQGV PVDGIGSQTH LDPGAAGQIQ GALTALANSG  240
VKEVAITELD IRTAPANDYA TVTKACLNVP KCIGITVWGV SDKNSWRKEH DSLLFDANYN  300
PKPAYTAVVN ALR                                                     313

SEQ ID NO: 3              moltype = AA   length = 305
FEATURE                   Location/Qualifiers
source                    1..305
                          mol_type = protein
                          organism = Fusarium verticillioides
SEQUENCE: 3
QAADSINKLI KNKGKLYYGT ITDPNLLGVA KDTAIIKADF GAVTPENSGK WDATEPSQGK   60
FNFGSFDQVV NFAQQNGLKV RGHTLVWHSQ LPQWVKNIND KATLTKVIEN HVTQVVGRYK  120
GKIYAWDVVN EIFEWDGTLR KDSHFNNVFG NDDYVGIAFR AARKADPNAK LYINDYSLDS  180
GSASKVTKGM VPSVKKWLSQ GVPVDGIGSQ THLDPGAAGQ IQGALTALAN SGVKEVAITE  240
LDIRTAPAND YATVTKACLN VPKCIGITVW GVSDKNSWRK EHDSLLFDAN YNPKPAYTAV  300
VNALR                                                              305

SEQ ID NO: 4              moltype = DNA   length = 1039
FEATURE                   Location/Qualifiers
source                    1..1039
                          mol_type = other DNA
                          organism = Fusarium verticillioides
SEQUENCE: 4
atgaagctgt cttctttcct ctacaccgcc tcgctggtcg cggccattcc caccgccatc   60
gagccccgcc aggctgccga cagcatcaac aagctgatca gaacaagggg caagctctac  120
tacggaacca tcaccgaccc caacctgctc ggcgtcgcaa aggacaccgc catcatcaag  180
gccgactttg gcgccgttac ccccgagaac tcgggcaagt gggacgccac cgagcccagc  240
cagggcaagt tcaacttcgg tagcttcgac caggttgtca actttgccca gcagaatggc  300
ctcaaggtcc gaggtcacac tctggtctgg cactctcagc tccctcagtg ggttaagaac  360
atcaacgaca aggctactct gaccaaggtc attgagaacc acgtcaccca agtcgttgga  420
cgctacaagg gcaagatcta cgcctgggta tgttttattc cccagacttt cttcgaaatg  480
actttgctaa catgttcagg acgtcgtcaa cgagatcttc gagtgggacg gtaccctccg  540
aaaggactct cacttcaaca acgtcttcgg caacgacgac tacgttggca ttgccttccg  600
```

```
cgccgcccgc aaggctgacc ccaacgccaa gctgtacatc aacgactaca gcctcgactc  660
cggcagcgcc tccaaggtca ccaagggtat ggttccctcc gtcaagaagt ggctcagcca  720
gggcgttccc gtcgacggca ttggctctca gactcacctt gaccccggtg ccgctggcca  780
aatccagggt gctctcactg ccctcgccaa ttctggtgtc aaggaggttg ccatcaccga  840
gctcgacatc cgcactgccc ccgccaacga ctacgctacc gtcaccaagg cctgcctcaa  900
cgtccccaag tgcattggta tcaccgtctg ggtgtctct gacaagaact cttggcgcaa  960
ggagcacgac agtcttctgt tcgatgctaa ctacaacccc aagcctgctt acactgctgt  1020
tgtcaacgct ctccgctaa                                               1039

SEQ ID NO: 5            moltype = DNA  length = 987
FEATURE                 Location/Qualifiers
source                  1..987
                        mol_type = other DNA
                        organism = Fusarium verticillioides
SEQUENCE: 5
atgaagctgt cttctttcct ctacaccgcc tcgctggtcg cggccattcc caccgccatc  60
gagccccgcc aggctgccga cagcatcaac aagctgatca agaacaaggg caagctctac  120
tacggaacca tcaccgaccc caacctgctc ggcgtcgcaa aggacaccgc catcatcaag  180
gccgactttg gcgccgttac ccccgagaac tcgggcaagt gggacgccac cgagcccagc  240
cagggcaagt tcaacttcgg tagcttcgac caggttgtca actttgccca gcagaatggc  300
ctcaaggtcc gaggtcacac tctggtctgg cactctcagc tccctcagtg ggttaagaac  360
atcaacgaca aggctactct gaccaaggtc attgagaacc acgtcaccca agtcgttgga  420
cgctacaagg gcaagatcta cgcctgggac gtcgtcaacg agatcttcga gtgggacggt  480
accctccgaa aggactctca cttcaacaac gtcttcggca acgacgacta cgttggcatt  540
gccttccgcg ccgcccgcaa ggctgacccc aacgccaagc tgtacatcaa cgactacagc  600
ctcgactccg gcagcgcctc caaggtcacc aagggtatgg ttccctccgt caagaagtgg  660
ctcagccagg gcgttcccgt cgacggcatt ggctctcaga ctcaccttga ccccggtgcc  720
gctggccaaa tccagggtgc tctcactgcc ctcgccaatt ctggtgtcaa ggaggttgcc  780
atcaccgagc tcgacatccg cactgccccc gccaacgact acgctaccgt caccaaggcc  840
tgcctcaacg tccccaagtg cattggtatc accgtctggg gtgtctctga caagaactct  900
tggcgcaagg agcacgacag tcttctgttc gatgctaact acaaccccaa gcctgcttac  960
actgctgttg tcaacgctct ccgctaa                                      987

SEQ ID NO: 6            moltype = DNA  length = 942
FEATURE                 Location/Qualifiers
source                  1..942
                        mol_type = other DNA
                        organism = Fusarium verticillioides
SEQUENCE: 6
attcccaccg ccatcgagcc ccgccaggct gccgacagca tcaacaagct gatcaagaac  60
aagggcaagc tctactacgg aaccatcacc gaccccaacc tgctcggcgt cgcaaaggac  120
accgccatca tcaaggccga ctttggcgcc gttacccccg agaactcggg caagtgggac  180
gccaccgagc ccagccaggg caagttcaac ttcggtagct tcgaccaggt tgtcaacttt  240
gcccagcaga atggcctcaa ggtccgaggt cacactctgg tctggcactc tcagctccct  300
cagtgggtta agaacatcaa cgacaaggct actctgacca aggtcattga gaaccacgtc  360
acccaagtcg ttggacgcta caagggcaag atctacgcct gggacgtcgt caacgagatc  420
ttcgagtggg acggtaccct ccgaaaggac tctcacttca acaacgtctt cggcaacgac  480
gactacgttg gcattgcctt ccgcgccgcc cgcaaggctg accccaacgc caagctgtac  540
atcaacgact acagcctcga ctccggcagc gcctccaagg tcaccaaggg tatggttccc  600
tccgtcaaga agtggctcag ccagggcgtt cccgtcgacg gcattggctc tcagactcac  660
cttgaccccg gtgccgctgg ccaaatccag ggtgctctca ctgccctcgc caattctggt  720
gtcaaggagg ttgccatcac cgagctcgac atccgcactg cccccgccaa cgactacgct  780
accgtcacca aggcctgcct caacgtcccc aagtgcattg gtatcaccgt ctggggtgtc  840
tctgacaaga actcttggcg caaggagcac gacagtcttc tgttcgatgc taactacaac  900
cccaagcctg cttacactgc tgttgtcaac gctctccgct aa                     942

SEQ ID NO: 7            moltype = DNA  length = 27
FEATURE                 Location/Qualifiers
misc_feature            1..27
                        note = Primer 1
source                  1..27
                        mol_type = other DNA
                        organism = synthetic construct
SEQUENCE: 7
caccatgaag ctgtcttctt tcctcta                                      27

SEQ ID NO: 8            moltype = DNA  length = 27
FEATURE                 Location/Qualifiers
misc_feature            1..27
                        note = Primer 2
source                  1..27
                        mol_type = other DNA
                        organism = synthetic construct
SEQUENCE: 8
tttttagcgg agagcgttga caacagc                                      27

SEQ ID NO: 9            moltype = AA  length = 328
FEATURE                 Location/Qualifiers
source                  1..328
```

```
                          mol_type = protein
                          organism = Fusarium oxysporum
SEQUENCE: 9
MKLSSFLYTA SLVAAIPTAI EPRQASDSIN KLIKNKGKLY YGTITDPNLL GVAKDTAIIK    60
ADFGAVTPEN SGKWDATEPS QGKFNFGSFD QVVNFAQQNG LKVRGHTLVW HSQLPQWVKN   120
INDKATLTKV IENHVTNVVG RYKGKIYAWD VVNEIFDWDG TLRKDSHFNN VFGNDDYVGI   180
AFRAARKADP NAKLYINDYS LDSGSASKVT KGMVPSVKKW LSQGVPVDGI GSQTHLDPGA   240
AGQIQGALTA LANSGVKEVA ITELDIRTAP ANDYATVTKA CLNVPKCIGI TVWGVSDKNS   300
WRKEHDSLLF DANYNPKAAY TAVVNALR                                     328

SEQ ID NO: 10             moltype = AA  length = 313
FEATURE                   Location/Qualifiers
source                    1..313
                          mol_type = protein
                          organism = Fusarium oxysporum
SEQUENCE: 10
IPTAIEPRQA SDSINKLIKN KGKLYYGTIT DPNLLGVAKD TAIIKADFGA VTPENSGKWD    60
ATEPSQGKFN FGSFDQVVNF AQQNGLKVRG HTLVWHSQLP QWVKNINDKA TLTKVIENHV   120
TNVVGRYKGK IYAWDVVNEI FDWDGTLRKD SHFNNVFGND DYVGIAFRAA RKADPNAKLY   180
INDYSLDSGS ASKVTKGMVP SVKKWLSQGV PVDGIGSQTH LDPGAAGQIQ GALTALANSG   240
VKEVAITELD IRTAPANDYA TVTKACLNVP KCIGITVWGV SDKNSWRKEH DSLLFDANYN   300
PKAAYTAVVN ALR                                                     313

SEQ ID NO: 11             moltype = AA  length = 305
FEATURE                   Location/Qualifiers
source                    1..305
                          mol_type = protein
                          organism = Fusarium oxysporum
SEQUENCE: 11
QASDSINKLI KNKGKLYYGT ITDPNLLGVA KDTAIIKADF GAVTPENSGK WDATEPSQGK    60
FNFGSFDQVV NFAQQNGLKV RGHTLVWHSQ LPQWVKNIND KATLTKVIEN HVTNVVGRYK   120
GKIYAWDVVN EIFDWDGTLR KDSHFNNVFG NDDYVGIAFR AARKADPNAK LYINDYSLDS   180
GSASKVTKGM VPSVKKWLSQ GVPVDGIGSQ THLDPGAAGQ IQGALTALAN SGVKEVAITE   240
LDIRTAPAND YATVTKACLN VPKCIGITVW GVSDKNSWRK EHDSLLFDAN YNPKAAYTAV   300
VNALR                                                              305

SEQ ID NO: 12             moltype = DNA  length = 1039
FEATURE                   Location/Qualifiers
source                    1..1039
                          mol_type = other DNA
                          organism = Fusarium oxysporum
SEQUENCE: 12
atgaagctgt cttccttcct ctacaccgcc tcgctggtcg cggccattcc caccgccatc    60
gagccccgcc aggcctccga cagcatcaac aagctgatca gaacaagggg caagctctac   120
tacggaacca tcaccgaccc caacctgctc ggcgtcgcaa aggacactgc catcatcaag   180
gctgactttg gcgccgtcac acccgagaac tcgggtaagt gggatgccac cgagcccagc   240
cagggcaagt tcaacttcgg cagcttcgac caggtcgtca actttgctca gcagaatggc   300
ctcaaggtcc gaggtcacac tctagtctgg cactcccagc tccctcagtg ggttaagaac   360
atcaacgaca aggctacttt gaccaaggtc atcgagaacc acgtcaccaa cgtcgttgga   420
cgctacaagg gcaagatcta cgcctgggta tgttttcttc actcgaactt cttataaatg   480
gctttactaa catgttcagg acgtcgttaa cgagatcttc gactgggatg gtaccctccg   540
aaaggactct cacttcaaca acgtcttcgg caacgacgac tacgttggca ttgccttccg   600
cgctgcccgc aaggctgacc ccaacgccaa gctgtacatc aacgactaca gcctcgactc   660
cggcagcgcc tccaaggtca ccaagggcat ggttccctct gtcaagaagt ggctcagcca   720
gggcgtcccc gtcgacggta ttggttctca gactcacctt gaccccggtg ccgctggcca   780
aatccagggt gctctcactg ccctcgccaa ctctggtgtg aaggaggttg ccatccacga   840
gctcgacatc cgcactgccc ccgccaacga ctacgctacc gttaccaagg cctgcctcaa   900
cgtccccaag tgcattggta tcaccgtctg ggcgtatct gacaagaact cttggcgcaa   960
ggagcacgac agccttctgt tcgatgctaa ctacaacccc aaggctgctt acactgctgt  1020
tgtcaacgct ctccgctaa                                               1039

SEQ ID NO: 13             moltype = DNA  length = 987
FEATURE                   Location/Qualifiers
source                    1..987
                          mol_type = other DNA
                          organism = Fusarium oxysporum
SEQUENCE: 13
atgaagctgt cttccttcct ctacaccgcc tcgctggtcg cggccattcc caccgccatc    60
gagccccgcc aggcctccga cagcatcaac aagctgatca gaacaagggg caagctctac   120
tacggaacca tcaccgaccc caacctgctc ggcgtcgcaa aggacactgc catcatcaag   180
gctgactttg gcgccgtcac acccgagaac tcgggtaagt gggatgccac cgagcccagc   240
cagggcaagt tcaacttcgg cagcttcgac caggtcgtca actttgctca gcagaatggc   300
ctcaaggtcc gaggtcacac tctagtctgg cactcccagc tccctcagtg ggttaagaac   360
atcaacgaca aggctacttt gaccaaggtc atcgagaacc acgtcaccaa cgtcgttgga   420
cgctacaagg gcaagatcta cgcctgggac gtcgttaacg agatcttcga ctgggatggt   480
accctccgaa aggactctca cttcaacaac gtcttcggca acgacgacta cgttggcatt   540
gccttccgct gccgcaa ggctgacccc aacgccaagc tgtacatcaa cgactacagc     600
ctcgactccg gcagcgcctc caaggtcacc aagggcatgg ttccctctgt caagaagtgg   660
ctcagccagg gcgtccccgt cgacggtatt ggttctcaga ctcaccttga ccccggtgcc   720
```

```
gctggccaaa tccagggtgc tctcactgcc ctcgccaact ctggtgtgaa ggaggttgcc    780
atcaccgagc tcgacatccg cactgccccc gccaacgact acgctaccgt taccaaggcc    840
tgcctcaacg tccccaagtg cattggtatc accgtctggg gcgtatcgta caagaactct    900
tggcgcaagg agcacgacag ccttctgttc gatgctaact acaaccccaa ggctgcttac    960
actgctgttg tcaacgctct ccgctaa                                         987

SEQ ID NO: 14            moltype = DNA  length = 942
FEATURE                  Location/Qualifiers
source                   1..942
                         mol_type = other DNA
                         organism = Fusarium oxysporum
SEQUENCE: 14
attcccaccg ccatcgagcc ccgccaggcc tccgacagca tcaacaagct gatcaagaac     60
aagggcaagc tctactacgg aaccatcacc gaccccaacc tgctcggcgt cgcaaaggac    120
actgccatca tcaaggctga ctttggcgcc gtcacacccg agaactcggg taagtgggat    180
gccaccgagc tccagccaggg caagttcaac ttcggcagct tcgaccaggt cgtcaacttt    240
gctcagcaga atggcctcaa ggtccgaggt cacactctag tctggcactc ccagctccct    300
cagtgggtta agaacatcaa cgacaaggct actttgacca aggtcatcga gaaccacgtc    360
accaacgtcg ttggacgcta caagggcaag atctacgcct gggacgtcgt taacgagatc    420
ttcgactggg atggtaccct ccgaaaggac tctcacttca caacgtctt cggcaacgac    480
gactacgttg gcattgcctt ccgcgctgcc cgcaaggctg accccaacgc caagctgtac    540
atcaacgact acagcctcga ctccggcagc gcctccaagg tcaccaaggg catggttccc    600
tctgtcaaga gtggctcag ccagggcgtc cccgtcgacg gtattggttc tcagactcac    660
cttgaccccg gtgccgctgg ccaaatccag ggtgctctca ctgccctcgc caactctggt    720
gtgaaggagg ttgccatcac cgagctcgac atccgcactg ccccgccaa cgactacgct    780
accgttacca aggcctgcct caacgtcccc aagtgcatcg gtatcaccgt ctgggcgta    840
tctgacaaga actcttggcg caaggagcac gacagccttc tgttcgatgc taactacaac    900
cccaaggctg cttacactgc tgttgtcaac gctctccgct aa                        942

SEQ ID NO: 15            moltype = AA  length = 305
FEATURE                  Location/Qualifiers
source                   1..305
                         mol_type = protein
                         organism = Fusarium sp.
SEQUENCE: 15
QAADSINKLI KNKGKLYYGT ITDPNLLGVA KDTAVIKADF GAVTPENSGK WDATEPSQGN     60
FNFGSFDQVV NFAQQNGLKV RGHTLVWHSQ LPQWVKNIND KATLTKVIEN HVTQVVGRYK    120
GKIYAWDVVN EIFDWDGTLR KDSHFNNVFG NDDYVGIAFR AARKADPNAK LYINDYSLDS    180
ASASKVTKGM VPSVKKWLSQ GVPVDGIGSQ SHLDPGAAGQ VQGALTALAN SGVKEVAITE    240
LDIRTAPAND YATVTKACLN VPKCIGITVW GVSDKNSWRK EHDSLLFDSN YNPKPAYTAV    300
VNALR                                                                 305

SEQ ID NO: 16            moltype = DNA  length = 1039
FEATURE                  Location/Qualifiers
source                   1..1039
                         mol_type = other DNA
                         organism = Fusarium sp.
SEQUENCE: 16
atgaagctgt cttctttcct ctacaccgcc tcgctggtcg cggccattcc caccgccatc     60
gagccccgcc aggccgccga cagcatcaac aagctgatca gaacaagggg caagctctac    120
tacggaacca tcaccgaccc caacctgctc ggcgtcgcaa aggacaccgc cgtcatcaag    180
gccgactttg gcgccgtcac ccccgagaac tcgggcaagt gggacgccac cgagcccagc    240
cagggcaact tcaacttcgg tagcttcgac caggtcgtca ctttgctca gcagaatggc    300
ctcaaggtcc gaggtcacac tctggtctgg cactctcagc tccctcagtg ggttaagaac    360
atcaacgaca aggctactct gaccaaggtc attgagaacc acgtcaccca agtcgttgga    420
cgctacaagg gcaagatcta cgcctgggta tgttttcttg cctcgacctt ctcaaagatg    480
aatttgctaa catgttcagg acgttgtcaa cgagatcttc gactgggacg gtaccctccg    540
aaaggattct cacttcaaca acgtcttcgg caacgatgac tacgttggca ttgccttccg    600
cgccgcccgc aaggctgacc ccaacgccaa gctgtacatc aacgactaca gcctcgactc    660
cgccagcgcc tccaaggtca caagggcat ggtcccctcc gtcaagaagt ggctcagcca    720
gggcgttccc gtcgacggca ttggctccca gtctcacctt gaccccggtg ccgctggcca    780
agtccagggt gctctcactg ccctcgccaa ctctggtgtc aaggaggttg ccatcaccga    840
gctcgacatc cgcactgccc ccgccaacga ctacgccacc gtcaccaagg cctgcctaaa    900
cgtccccaag tgcattggta tcaccgtctg ggtgtctct gacaagaact cttggcgcaa    960
ggagcacgac agccttctgt tcgactccaa ctacaacccc aagcctgctt acactgctgt   1020
tgtcaacgct ctccgctaa                                                1039

SEQ ID NO: 17            moltype = DNA  length = 987
FEATURE                  Location/Qualifiers
source                   1..987
                         mol_type = other DNA
                         organism = Fusarium sp.
SEQUENCE: 17
atgaagctgt cttctttcct ctacaccgcc tcgctggtcg cggccattcc caccgccatc     60
gagccccgcc aggccgccga cagcatcaac aagctgatca gaacaagggg caagctctac    120
tacggaacca tcaccgaccc caacctgctc ggcgtcgcaa aggacaccgc cgtcatcaag    180
gccgactttg gcgccgtcac ccccgagaac tcgggcaagt gggacgccac cgagcccagc    240
cagggcaact tcaacttcgg tagcttcgac caggtcgtca ctttgctca gcagaatggc    300
ctcaaggtcc gaggtcacac tctggtctgg cactctcagc tccctcagtg ggttaagaac    360
```

```
                                                  -continued
atcaacgaca aggctactct gaccaaggtc attgagaacc acgtcaccca agtcgttgga   420
cgctacaagg gcaagatcta cgcctgggac gttgtcaacg agatcttcga ctgggacggt   480
accctccgaa aggattctca cttcaacaac gtcttcggca acgatgacta cgttggcatt   540
gccttccgcg ccgcccgcaa ggctgacccc aacgccaagc tgtacatcaa cgactacagc   600
ctcgactccg ccagccgctc caaggtcacc aagggcatgg tccctccgt caagaagtgg    660
ctcagccagg gcgttccgt cgacggcatt ggctcccagt ctcaccttga ccccggtgcc   720
gctggccaag tccagggtgc tctcactgcc ctcgccaact ctggtgtcaa ggaggttgcc   780
atcaccgagc tcgacatccg cactgccccc gccaacgact acgccaccgt caccaaggcc   840
tgcctaaacg tccccaagtg cattggtatc accgtctggg gtgtctctga caagaactct   900
tggcgcaagg agcacgacag ccttctgttc gactccaact acaaccccaa gcctgcttac   960
actgctgttg tcaacgctct ccgctaa                                      987

SEQ ID NO: 18         moltype = DNA  length = 942
FEATURE               Location/Qualifiers
source                1..942
                      mol_type = other DNA
                      organism = Fusarium sp.
SEQUENCE: 18
attcccaccg ccatcgagcc ccgccaggcc gccgacagca tcaacaagct gatcaagaac    60
aagggcaagc tctactacgg aaccatcacc gaccccaacc tgctcggcgt cgcaaaggac   120
accgccgtca tcaaggccga cttggcgcc gtcaccccg agaactcggg caagtgggac    180
gccaccgagc ccagccaggg caacttcaac ttcggtagct tcgaccaggt cgtcaacttt   240
gctcagcaga atggcctcaa ggtccgaggt cacactctgg tctggcactc tcagctccct   300
cagtgggtta agaacatcaa cgacaaggct actctgacca aggtcattga gaaccacgtc   360
acccaagtcg ttggacgcta caagggcaag atctacgcct gggacgttgt caacgagatc   420
ttcgactggg acggtaccct ccgaaaggat tctcacttca acaacgtctt cggcaacgat   480
gactacgttg gcattgcctt ccgcgccgcc cgcaaggctg accccaacgc caagctgtac   540
atcaacgact acagcctcga ctccgccagc gcctccaagg tcaccaaggg catggtcccc   600
tccgtcaaga agtggctcag ccagggcgtt cccgtcgacg gcattggctc ccagtctcac   660
cttgaccccg gtgccgctgg ccaagtccag ggtgctctca ctgccctcgc caactctggt   720
gtcaaggagg ttgccatcac cgagctcgac atccgcactg cccccgccaa cgactacgcc   780
accgtcacca aggcctgcct aaacgtcccc aagtgcattg gtatcaccgt ctgggtgtc   840
tctgacaaga actcttggcg caaggagcac gacagccttc tgttcgactc caactacaac   900
cccaagcctg cttacactgc tgttgtcaac gctctccgct aa                    942

SEQ ID NO: 19         moltype = DNA  length = 40
FEATURE               Location/Qualifiers
misc_feature          1..40
                      note = Primer 1
source                1..40
                      mol_type = other DNA
                      organism = synthetic construct
SEQUENCE: 19
ccgcggccgc accatgaagc tgtcttcctt cctctacacc                          40

SEQ ID NO: 20         moltype = DNA  length = 37
FEATURE               Location/Qualifiers
misc_feature          1..37
                      note = Primer 2
source                1..37
                      mol_type = other DNA
                      organism = synthetic construct
SEQUENCE: 20
ccggcgcgcc cttattagcg gagagcgttg acaacag                             37
```

XYLANASES FOR SOLUBILIZING ARABINOXYLAN-CONTAINING MATERIAL

CROSS-REFERENCE TO RELATED APPLICATIONS

This application is a divisional of U.S. patent application Ser. No. 16/839,897, filed Apr. 3, 2020, which is a divisional of U.S. patent application Ser. No. 15/843,023, filed Dec. 15, 2017, now U.S. Pat. No. 10,612,014, which is a continuation of U.S. patent application Ser. No. 14/418,900, filed Jan. 30, 2015, now abandoned, which is a U.S. National Stage Application under 35 U.S.C. § 371 of International Application No. PCT/EP2013/066255, filed Aug. 2, 2013, which claims priority to PCT Application No. Application No. PCT/CN2012/079650, filed Aug. 3, 2012, and Chinese Patent Application No. 201310311358.1, filed Jul. 23, 2013, the disclosures of each of which are incorporated by reference herein in their entireties.

FIELD OF THE INVENTION

The present invention relates to the use of xylanases having unusual properties in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry, and methods using these xylanases, as well as compositions (such as feed additive compositions) comprising said xylanases. The present invention also relates to a new xylanase with unusual properties that renders it useful in applications, including in feedstuffs, in brewing or malting, in the treatment of arabinoxylan containing raw materials like grain-based materials, e.g. in the production of biofuel or biochemicals (e.g. bio-based isoprene), and/or in the wheat gluten-starch separation industry.

INCORPORATION BY REFERENCE

The contents of the electronic submission of the text file Sequence Listing, named "NB40020-US-PCD1_SequenceListing.xml" was created on Sep. 1, 2022 and is 31 KB in size, which is hereby incorporated by reference in its entirety.

BACKGROUND OF THE INVENTION

For many years, endo-β-1,4-xylanases (EC 3.2.1.8) (referred to herein as xylanases) have been used for the modification of complex carbohydrates derived from plant cell wall material. It is well known in the art that the functionality of different xylanases (derived from different microorganisms or plants) differs enormously. Xylanase is the name given to a class of enzymes which degrade the linear polysaccharide beta-1,4-xylan into xylooligosaccharides or xylose, thus breaking down hemicellulose, one of the major components of plant cell walls.

Based on structural and genetic information, xylanases have been classified into different Glycoside Hydrolase (GH) families (Henrissat, (1991) *Biochem. J.* 280, 309-316).

Initially all known and characterized xylanases belonged to the families GH10 or GH11. Further work then identified numerous other types of xylanases belonging to the families GH5, GH7, GH8 and GH43 (Collins et al (2005) *FEMS Microbiol Rev.*, 29 (1), 3-23).

Until now the GH11 family differs from all other GH's, being the only family solely consisting of xylan specific xylanases. The structure of the GH11 xylanases can be described as a β-Jelly roll structure or an all β-strand sandwich fold structure (Himmel et al 1997 Appl. Biochem. Biotechnol. 63-65, 315-325). GH11 enzymes have a catalytic domain of around 20 kDa.

GH10 xylanases have a catalytic domain with molecular weights in the range of 32-39 kDa. The structure of the catalytic domain of GH10 xylanases consists of an eightfold β/α barrel (Harris et al 1996-Acta. Crystallog. Sec. D 52, 393-401).

Three-dimensional structures are available for a large number of Family GH10 enzymes, the first solved being those of the *Streptomyces lividans* xylanase A (Derewenda et al J Biol Chem 1994 Aug. 19; 269(33) 20811-4), the *C. fimi* endo-glycanase Cex (White et al Biochemistry 1994 Oct. 25; 33(42) 12546-52), and the *Cellvibrio japonicus* Xyn10A (previously Pseudomonasfluorescens subsp. xylanase A) (Harris et al Structure 1994 Nov. 15: 2(11) 1107-16). As members of Clan GHA they have a classical $(\alpha/\beta)_8$ TIM barrel fold with the two key active site glutamic acids located at the C-terminal ends of beta-strands 4 (acid/base) and 7 (nucleophile) (Henrissat et al Proc Natl Acad Sci USA 1995 Jul. 18; 92(15) 7090-4).

Comprehensive studies characterising the functionality of xylanases have been done on well characterised and pure substrates (Kormelink et al, 1992 Characterisation and mode of action of xylanases and some accessory enzymes. Ph.D. Thesis, Agricultural University Wageningen, Holland (175 pp., English and Dutch summaries)). These studies show that different xylanases have different specific requirements with respect to substitution of the xylose backbone of the arabinoxylan (AX). Some xylanases require three un-substituted xylose residues to hydrolyse the xylose backbone; others require only one or two. The reasons for these differences in specificity are thought to be due to the three dimensional structure within the catalytic domains, which in turn is dependent on the primary structure of the xylanase, i.e. the amino acid sequence. However, the translation of these differences in the amino acid sequences into differences in the functionality of the xylanases, has up until now not been documented when the xylanase acts in a complex environment, such as a plant material, e.g. in a feedstuff.

The xylanase substrates in plant material, e.g. in wheat, have traditionally been divided into two fractions: The water un-extractable AX (WU-AX) and the water extractable AX (WE-AX). There have been numerous explanations as to why there are two different fractions of AX. The older literature (D'Appolonia and MacArthur-(1976, Cereal Chem. 53. 711-718) and Montgomery and Smith (1955. J. Am. Chem. Soc. 77. 3325-332) describes quite high differences in the substitution degree between WE-AX and WU-AX. The highest degree of substitution was found in WE-AX. This was used to explain why some of the AX was extractable. The high degree of substitution made the polymer soluble, compared to a lower substitution degree, which would cause hydrogen bonding between polymers and consequently precipitation.

The difference between the functionality of different xylanases has been thought to be due to differences in xylanase specificity and thereby their preference for the WU-AX or the WE-AX substrates.

Xylanase enzymes have been reported from nearly 100 different organisms, including plants, fungi and bacteria. The xylanase enzymes are classified into several of the more than 40 families of glycosyl hydrolase enzymes. The glycosyl hydrolase enzymes, which include xylanases, mannanases, amylases, β-glucanases, cellulases, and other carbohydrases, are classified based on such properties as the sequence of amino acids, their three dimensional structure and the geometry of their catalytic site (Gilkes, et al., 1991, Microbiol. Reviews 55: 303-315).

BRIEF DESCRIPTION OF THE DRAWINGS

FIG. 1 shows a polypeptide sequence (SEQ ID No. 1) of a xylanase of the present invention (FveXyn4). This is the pre-pro-protein. Underlined (lower case) portion of the sequence reflects an N terminal signal peptide can be cleaved before the enzyme is matured. The amino acids shown in bold and italicized may also be cleaved by post-translational modification before the enzyme is fully matured.

FIG. 2 shows a polypeptide sequence (SEQ ID No. 2) of a xylanase of the present invention (FveXyn4). This is the pro-protein. The amino acids shown in bold and italicized may also be cleaved by post-translational modification before the enzyme is fully matured.

FIG. 3 shows a polypeptide sequence (SEQ ID No. 3) of a xylanase of the present invention (FveXyn4). This is the active form of the enzyme. This may be referred to herein as the mature form of the enzyme.

FIG. 4 shows a nucleotide sequence (SEQ ID No. 4) encoding a xylanase of the present invention (FveXyn4). The lower case nucleotides which are in bold show the intron sequence. The signal sequence is shown bold (upper case).

FIG. 5 shows a nucleotide sequence (SEQ ID No. 5) encoding a xylanase of the present invention (FveXyn4). The signal sequence is shown bold (upper case).

FIG. 6 shows a nucleotide sequence (SEQ ID No. 6) encoding a xylanase of the present invention (FveXyn4).

FIG. 15 shows a polypeptide sequence (SEQ ID No. 9) of a xylanase of the present invention (FoxXyn2). This is the pre-pro-protein. Underlined (lower case) portion of the sequence may reflect an N terminal signal peptide which can be cleaved before the enzyme is matured. The amino acids shown in bold and italicized may also be cleaved by post-translational modification before the enzyme is fully matured.

FIG. 16 shows a polypeptide sequence (SEQ ID No. 10) of a xylanase of the present invention (FoxXyn2). This is the pro-protein. The amino acids shown in bold and italicized may also be cleaved by post-translational modification before the enzyme is fully matured. This sequence may be an active form of the protein and may be one active form of the protein. This may be referred to herein as the mature form of the enzyme.

FIG. 17 shows a polypeptide sequence (SEQ ID No. 11) of a xylanase of the present invention (FoxXyn2). This is another active form of the enzyme. In some embodiments, this may be referred to herein as the mature form of the enzyme.

FIG. 19 shows a nucleotide sequence (SEQ ID No. 12) encoding a xylanase of the present invention (FoxXyn2). The lower case nucleotides which are in bold show the intron sequence. The signal sequence is shown bold (upper case).

FIG. 20 shows a nucleotide sequence (SEQ ID No. 13) encoding a xylanase of the present invention (FoxXyn2). The signal sequence is shown bold (upper case).

FIG. 21 shows a nucleotide sequence (SEQ ID No. 14) encoding a xylanase of the present invention (FoxXyn2).

FIG. 25 shows a polypeptide sequence (SEQ ID No. 15) of a xylanase of the present invention (from *Fusarium*)—*Fusarium* Comparative Sequencing Project, Broad Institute of Harvard and MIT (broadinstitute.org). In some embodiments, this may be referred to herein as the mature form of the enzyme.

FIG. 26 shows an alignment of the mature proteins for FveXyn4 (SEQ ID No. 3), FoxXyn2 (SEQ ID No. 11) and the xylanase shown herein as SEQ ID No. 15.

FIG. 30 shows a nucleotide sequence (SEQ ID No. 16) encoding a xylanase for use in the present invention from *Fusarium*—obtained from *Fusarium* Comparative Sequencing Project, Broad Institute of Harvard and MIT (broadinstitute.org). The lower case nucleotides which are in bold show the intron sequence. The signal sequence is shown bold (upper case). Changes compared with SEQ ID No. 4 are underlined.

FIG. 31 shows a nucleotide sequence (SEQ ID No. 17) encoding a xylanase for use in the present invention from *Fusarium*—obtained from *Fusarium* Comparative Sequencing Project, Broad Institute of Harvard and MIT (broadinstitute.org). The signal sequence is shown bold (upper case). Changes compared with SEQ ID No. 5 are underlined.

FIG. 32 shows a nucleotide sequence (SEQ No, 18) encoding a xylanase for use in the present invention from *Fusarium*—obtained from *Fusarium* Comparative Sequencing Project, Broad Institute of Harvard and MIT (broadinstitute.org). Changes compared with SEQ ID No. 6 are underlined.

SUMMARY OF THE INVENTION

Figure 7:
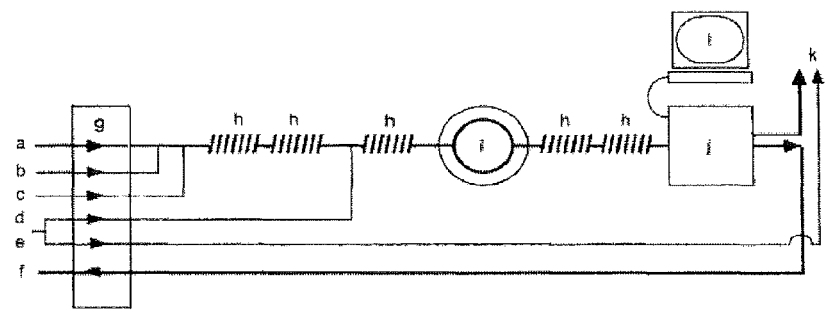
FIG. 7 shows a scheme of an auto-analyzer for the determination of pentosan by an automated phloroglucinol method: (a) Acetic acid mixed with HCl; (b) air bubbling; (c) phloroglucinol in ethanol; (d) sample; (e) sample accelerator; (f) flow cell way-out; (g) peristaltic pump; (h) glass 25 coil; (i) thermostat (96° C.); (j) multiple wavelength spectrophotometer (410, 510, 550, and 620 nm); (k) waste; (l) computer (Rouau & Surget, 1994 Carbohydrate Polymers, 24, 123-32).

A seminal finding of the present invention is a novel xylanase isolated from *Fusarium verticilloides*, which enzyme has surprising and unexpected properties. In particular it is unexpectedly good at breaking down (solubilising) insoluble arabinoxylans (AXinsol). Surprisingly the enzyme has been found to efficiently breakdown (solubilise) AXinsol from a wide range of substrates, including corn, wheat, DDGS, etc, in particular corn and corn based substrates, in particular both wheat (including wheat-based) products and corn (including corn-based products). This contrasts with prior-known enzymes, which are often inferior at solubilising AXinsol in corn or corn-based substrates or which are not efficient in both wheat- and corn-based substrates.

In addition, the enzyme of the present invention is particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol), a (fast) reduction in viscosity is obtained or the solubilized polymers (obtained from dissolving AXinsol) cannot contribute to increasing viscosity. This latter effect is essential in some of the claimed applications.

Without wishing to be bound by theory, the enzyme of the present invention mainly releases polymers, which do not contribute to viscosity, because the released polymers are short.

For the first time, the present inventors have isolated and sequenced this novel xylanase. Typically, conventional xylanases may breakdown AXinsol, but will often lead to an increase in viscosity of the mixture. This increased viscosity is disadvantageous in many applications. Without wishing to be bound by theory, although some conventional xylanases breakdown AXinsol, they lead to an increase in soluble degradation products of high molecular weight, which leads to an increase in viscosity in the mixture.

Furthermore or alternatively and again without wishing to be bound by theory, conventional xylanase enzymes may breakdown AXinsol, but because they do not degrade the solubilised products of high molecular weight fast enough the viscosity in the mixture is not ideal. In contrast, with the methods and uses of the present invention, the xylanases breakdown AXinsol without increasing viscosity and/or whilst reducing viscosity quickly compared with conventional enzymes. Without wishing to be being bound by theory, it is believed that high molecular weight products are not formed by the enzymes of the present invention.

The enzymes of the present invention and as described herein have been found to not only breakdown (solubilise) insoluble arabinoxylans (AXinsol) from a wide range of substrates, including corn, wheat, DDGS, etc, in particular corn and corn-based substrates, in particular both wheat (including wheat-based) products and corn (including corn-based products), but also efficiently ensuring that viscosity is not raised and/or reducing viscosity. Without wishing to be being bound by theory, it is believed that high molecular weight products are not formed by the enzymes of the present invention.

Thus the present invention relates to enzymes capable of solubilising pentosans, in particular xylan-containing materials, such as arabinoxylans, in particular insoluble arabinoxylans. In particular the enzyme is particularly good at solubilising pentosans in particular xylan-containing materials, such as arabinoxylans, in particular insoluble arabinoxylans, in a broad spectrum of substrates, including corn based substrates.

The present invention further relates to enzymes capable of degrading AXsol or the breakdown products of AXinsol to ensure viscosity is not increased and/or is reduced in the reaction mixture.

Many of the xylanases commercialized for use in feedstuffs for solubilizing pentosans are GH11 enzymes. It had been considered by those skilled in the art that GH10 xylanases were not as strong at solubilizing pentosans, particularly AXinsol, compared with GH11 xylanases. Surprisingly it has been found that the novel xylanase disclosed herein which is a GH10 xylanase is particularly good at degrading AXinsol in a broad spectrum of substrates, including corn based substrates. Surprisingly, the present inventors have found that the GH10 xylanases of the present invention outperform commercial GH11 xylanases in their ability to solubilize pentosans.

The fact that the present enzymes efficiently degrade AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-based diet, such as corn-soy diet for example.

It was completely unexpected for a GH10 xylanase to be so good on degrading AXinsol in cereals, particularly in corn or corn-based substrates.

The enzymes of the present invention are able to efficiently (and quickly) degrade the polymers and oligomers that are produced from degradation of AXinsol or that are present in grain-based material. This leads to an unexpected advantage for the GH10 xylanases taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g. bio-based isoprene); or in the wheat gluten-starch separation industry for the production of starch for example.

Notably it has been found that the degradation product on average is shorter for the GH10 enzymes tested herein compared with GH11 enzymes. This means that the degradation products do not contribute to or cause an increase in viscosity.

Based on these findings, the xylanases according to the present invention can be used to degrade a xylan-containing material, particularly arabinoxylans, particularly AXinsol. In addition or alternatively, the xylanases according to the present invention can be used to degrade soluble polymers (e.g. oligomers) that are produced from degradation of AXinsol or that are (naturally) present in grain-based materials. Surprisingly it has been found that the xylanases according the present invention can be used to both degrade a xylan-containing material, particularly arabinoxylans, particularly AXinsol, and to degrade soluble polymers (e.g. oligomers) that are produced from degradation of AXinsol.

Such enzymes finds useful application in many industries, including feedstuffs, malting and brewing, in the treatment of arabinoxylan containing raw materials like grain-based materials, in the wheat gluten-starch separation industry, in the production of starch derived syrups, in biofuel production, and the like.

Only through the isolation and testing of FveXyn 4 (SEQ ID No. 3) were these surprising and unexpected technical effects found. Thereafter it was possible to identify other similar acting enzymes (e.g. SEQ ID No. 11 and/or SEQ ID No. 15).

STATEMENTS OF THE INVENTION

According to a first aspect the present invention provides a xylanase comprising (or consisting of) a polypeptide sequence shown herein as SEQ ID No. 1, SEQ ID No. 2 or SEQ ID No. 3, or a variant, homologue, fragment or derivative thereof having at least 98.5% (e.g. at least 98.8 or 99 or 99.1 or 99.5%) identity with SEQ ID No. 1 or SEQ ID No. 2 or SEQ ID No. 3; or a xylanase which is encoded by a nucleotide sequence shown herein as SEQ ID No. 4, SEQ ID No. 5 or SEQ ID No. 6, or a nucleotide sequence which has at least 97.7% (e.g. at least 98%, 98.5% or 99%) identity with SEQ ID No. 4. SEQ ID No. 5 or SEQ ID No. 6.

In a further aspect the present invention provides an isolated or recombinant nucleic acid molecule comprising (or consisting of) a polynucleotide sequence selected from the group consisting of:
a. a polynucleotide sequence which encodes a polypeptide sequence selected from the group consisting of SEQ ID No. 1, SEQ ID No. 2 or SEQ ID No. 3, or a variant, homologue, fragment or derivative thereof having at least 98.5% (e.g. at least 98.8 or 99 or 99.1 or 99.5%) identity with SEQ ID No. 1 or SEQ ID No. 2 or SEQ ID No. 3; or
b. a polynucleotide sequence shown herein as SEQ ID No. 4. SEQ ID No. 5 or SEQ ID No. 6; or a nucleotide sequence which has at least 97.7% (e.g. at least 98%, 98.5% or 99%) identity with SEQ ID No. 4, SEQ ID No. 5 or SEQ ID No. 6.

In one aspect of the present invention there is provided a vector (e.g. a plasmid) comprising a polynucleotide sequence selected from the group consisting of:
a. a polynucleotide sequence which encodes a polypeptide sequence selected from the group consisting of SEQ ID No. 1, SEQ ID No. 2 or SEQ ID No. 3, or a variant, homologue, fragment or derivative thereof having at least 98.4% (e.g. at least 98.5% or 98.8 or 99 or 99.1 or 99.5%) identity with SEQ ID No. 1 or SEQ ID No. 2 or SEQ ID No. 3; or
b. a polynucleotide sequence shown herein as SEQ ID No. 4, SEQ ID No. 5 or SEQ ID No. 6; or a nucleotide sequence which has at least 97.7% (e.g. at least 98%, 98.5% or 99%) identity with SEQ ID No. 4. SEQ ID No. 5 or SEQ ID No. 6.

A further aspect of the present invention provides a host cell comprising a vector of the present invention or a nucleic acid comprising (or consisting of) a nucleotide sequence shown herein as SEQ ID No. 4, SEQ ID No. 5 or SEQ ID No. 6; or a nucleotide sequence which has at least 97.7% (e.g. at least 98%, 98.5% or 99%) identity with SEQ ID No. 4, SEQ ID No. 5 or SEQ ID No. 6.

The present invention further relates to a method for degrading arabinoxylan-containing material comprising admixing an arabinoxylan-containing material with a xylanase, which xylanase is a GH10, fungal xylanase and degrades insoluble arabinoxylan (AXinsol) as well as degrading the polymers, oligomers or combinations thereof produced from the degradation of the AXinsol, and wherein the xylanase degrades the polymers, oligomers or combinations thereof produced from the degradation of the AXinsol immediately or substantially immediately upon their production.

The present invention further relates to a method of degrading insoluble arabinoxylan-containing material comprising admixing the material with a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2, SEQ ID No. 3, SEQ ID No. 9, SEQ ID No. 10, SEQ ID No. 11 or SEQ ID No. 15; or a polypeptide sequence which comprises SEQ ID No. 1, SEQ ID No. 2, SEQ ID No. 3. SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4. SEQ ID No. 5, SEQ ID No. 6, SEQ ID No. 12, SEQ ID No. 13, SEQ ID No. 14, SEQ ID No. 16, SEQ ID No. 17 or SEQ ID No. 18; or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

The present invention further relates to a method for producing glucose or starch (e.g. starch from wheat or glucose from starch), comprising admixing a xylan-containing material (preferably an arabinoxylan-containing material, such as an insoluble arabinoxylan-containing material) with a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11, or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2. SEQ ID No. 3. SEQ ID No. 9, SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11, or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13. SEQ ID No. 14. SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

In one embodiment the xylan-containing material further comprises starch.

Use of a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1, SEQ ID No. 2, SEQ ID No. 3, SEQ ID No. 9, SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4. SEQ ID No. 5, SEQ ID No. 6, SEQ ID No. 12. SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code for degrading a xylan-containing material (preferably an arabinoxylan-containing material, preferably an insoluble arabinoxylan-containing material), optionally without increasing the viscosity or also decreasing the viscosity of the reaction mixture.

According to another aspect of the present invention, there is provided a method for improving the performance of a subject or for improving digestibility of a raw material in a feed (e.g. nutrient digestibility) or for improving feed efficiency in a subject or for reducing the viscosity of the intestinal content, the method comprising administering a subject with a xylanase comprising (or consisting of) a polypeptide sequence shown herein as SEQ ID No. 1, SEQ ID No. 2. SEQ ID No. 3. SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1, SEQ ID No. 2, SEQ ID No. 3, SEQ ID No. 9. SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14. SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code or administering a subject with a xylanase obtainable (or obtained) from *Fusarium verticilloides*.

A yet further aspect of the present invention is use of a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16. SEQ ID No. 17 or SEQ ID No. 18, or a nucleotide sequence which can hybridize to SEQ ID No. 4. SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code or use of a xylanase obtainable (or obtained) from *Fusarium verticilloides* for improving the performance of a subject or for improving digestibility of a raw material in a feed (e.g. nutrient digestibility) or for improving feed efficiency in a subject or for reducing the viscosity of the intestinal content.

In another aspect the present invention provides a feed additive composition comprising (or consisting essentially of or consisting of) a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11, or SEQ ID No. 15 or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No.

5, SEQ ID No. 6, SEQ ID No. 12. SEQ ID No. 13, SEQ ID No. 14. SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code; or a xylanase obtainable (or obtained) from *Fusarium verticilloides*.

In a further aspect the present invention provides a kit comprising xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13. SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13. SEQ ID No. 14. SEQ ID No. 16. SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code and instructions for administration.

In a yet further aspect the present invention provides a feedstuff comprising a feed additive composition comprising (or consisting essentially of or consisting of) a xylanase comprising (or consisting of) a polypeptide sequence shown herein as SEQ ID No. 1, SEQ ID No. 2, SEQ ID No. 3, SEQ ID No. 9, SEQ ID No. 10. SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1. SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14. SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16. SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16. SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides*.

A premix comprising a feed additive composition comprising (or consisting essentially of or consisting of) a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code; or a xylanase obtainable (or obtained) from *Fusarium verticilloides*, and at least one mineral and/or at least one vitamin.

In another aspect, the present invention provides a method of preparing a feedstuff comprising admixing a feed component with a feed additive composition comprising (or consisting essentially of or consisting of) a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4. SEQ ID No. 5, SEQ ID No. 6. SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4. SEQ ID No. 5, SEQ ID No. 6, SEQ ID No. 12. SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides*.

According to another aspect of the present invention, there is provided a method for degrading grain-based material (including whole grains or partial grains or malted grains, e.g. malted barley) and reducing viscosity in the reaction medium (e.g. grain mash), the method comprising admixing said grain-based material with a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides*.

A yet further aspect of the present invention is use of a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or use of a xylanase obtainable (or obtained) from *Fusarium verticilloides* for degrading grain-based material (including whole grains or partial grains or malted grains, e.g. malted barley) whilst reducing viscosity in the reaction medium (e.g. grain mash).

According to another aspect of the present invention, there is provided a method for producing biofuel (e.g. bioethanol) or a biochemical (e.g. bio-based isoprene) comprising admixing a grain-based material with a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4. SEQ ID No. 5. SEQ ID No. 6, SEQ ID No. 12, SEQ ID No. 13, SEQ ID No. 14. SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13. SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides*.

A yet further aspect of the present invention is use of a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or use of a xylanase obtainable (or obtained)

from *Fusarium verticilloides* for producing biofuel (e.g. bioethanol) or a biochemical (e.g. bio-based isoprene).

According to another aspect of the present invention, there is provided a method for separating a cereal flour (e.g. wheat flour) into starch and gluten fractions the method comprising admixing a cereal flour (e.g. wheat flour), water and a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides*.

A yet further aspect of the present invention provides the use of a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4. SEQ ID No. 5, SEQ ID No. 6, SEQ ID No. 12, SEQ ID No. 13. SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, or use of a xylanase obtainable (or obtained) from *Fusarium verticilloides* for separating a cereal flour (e.g. wheat flour) into starch and gluten fractions whilst reducing viscosity in the reaction medium (e.g. grain mash).

In a further aspect there is provided the use of the xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2, SEQ ID No. 3, SEQ ID No. 9, SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18; or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, in the production of a fermented beverage, such as a beer.

In a yet further aspect, the present invention provides a method of producing a fermented beverage (e.g. beer) comprising the step of contacting a mash and/or a wort with a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2, SEQ ID No. 3, SEQ ID No. 9, SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13. SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14. SEQ ID No. 16. SEQ ID No. 17 or SEQ ID No. 18; or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

A further aspect of the present invention provides a method of producing a fermented beverage (e.g. beer) comprising the steps of. (a) preparing a mash, (b) filtering the mash to obtain a wort, and (c) fermenting the wort to obtain a fermented beverage, such as a beer, wherein xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2, SEQ ID No. 3, SEQ ID No. 9, SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14. SEQ ID No. 16. SEQ ID No. 17 or SEQ ID No. 18; or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code, is added to: (i) the mash of step (a) and/or (ii) the wort of step (b) and/or (iii) the wort of step (c).

The present invention yet further provides a fermented beverage, such as a beer, produced by a method of present invention.

For the avoidance of doubt, SEQ ID No. 3 is the mature form of SEQ ID No. 1 or SEQ ID No. 2.

Likewise, SEQ ID No. 11 is the mature form of SEQ ID No. 9 or SEQ ID No. 10.

DETAILED DISCLOSURE OF THE PREFERRED EMBODIMENTS OF THE INVENTION

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial. NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Increasing prices of raw material traditionally used as energy source in animal feed, as a feedstock in biofuel production, as an ingredient in brewing or malting, or as a feedstock in wheat gluten-starch separation processes for instance have resulted in inclusion of low-cost fibrous materials in the starting substrates for these industries, particularly the use of low-cost fibrous by-products in animal feed.

Fibre addition may cause several disadvantageous effects. For example in animal feed fibre addition may cause anti-nutritional effects. The presence of un-degraded polymers present in the animal's intestine causes a highly viscous content and impeded diffusion with reduced nutrient absorption as a result. Also, the polymers possess a high water holding capacity hindering an effective re-absorption of water, and the water retention increases the volume of the gut content, which leads to a decrease intestinal transit time (Englyst & Kingman (1993) in Human Nutrition and Dietetics, 9th edition (Garrow J. S., James W. P. T., eds.) p. 53).

In feedstuffs, hemicellulose and cellulose (including insoluble arabinoxylan) also form physical barriers encapsulating (or entrapping) nutrients like starch and protein and thereby retaining access to these nutrients for the animal.

Hemicellulose and cellulose (including insoluble arabinoxylans (AXinsol)) by themselves are also potential energy sources, as they consist of C5- and C6-saccharides. Mono C6-saccharides can be used as energy source by the animal, while oligo C5-saccharides can be transformed into short chain fatty acids by the micro flora present in the animal gut (van den Broek et al., 2008 Molecular Nutrition & Food Research, 52, 146-63), which short chain fatty acids can be taken up and digested by the animal's gut.

Release of nutrients and water from feedstuffs as a consequence of physical barrier degradation is dependent on the ability of the xylanase to degrade insoluble fibre components (e.g. insoluble arabanoxylans (AXinsol)).

In one aspect, the present invention relates to a novel xylanase.

In one embodiment the present invention provides a xylanase enzyme comprising (or consisting of) a polypeptide sequence shown herein as SEQ ID No. 1. SEQ ID No. 2 or SEQ ID No. 3 or a variant, homologue, fragment or derivative thereof having at least 98.4% (e.g. at least 98.5 or 98.8 or 99 or 99.1 or 99.5%) identity with SEQ ID No. 1 or SEQ ID No. 2 or SEQ ID No. 3. The present invention also relates to a xylanase which is encoded by a nucleotide sequence shown herein as SEQ ID No. 4, SEQ ID No. 5 or SEQ ID No. 6, or a nucleotide sequence which can hybridize to SEQ ID No. 4, SEQ ID No. 5 or SEQ ID No. 6 under high stringency conditions, or a nucleotide sequence which has at least 97.7% (e.g. at least 98%, 98.5% or 99%) identity with SEQ ID No. 4, SEQ ID No. 5 or SEQ ID No. 6.

In one aspect, the xylanase enzyme of the present invention may be obtainable from (or obtained from) a fungus, namely *Fusarium verticilloides*.

In another aspect, the present invention provides a xylanase obtainable from (or obtained from) *Fusarium verticilloides* for use in feed or a feed additive composition.

In one embodiment the xylanase enzyme of the present invention may be referred to herein as FveXyn4 or Hifi 168.

The present invention yet further provides a nucleic acid comprising (or consisting of) a nucleotide sequence shown herein as SEQ ID No. 4, SEQ ID No. 5 or SEQ ID No. 6; or a nucleotide sequence which has at least 97.7% (e.g. at least 98%, 98.5% or 99%) identity with SEQ ID No. 4, SEQ ID No. 5 or SEQ ID No. 6.

Both the polypeptide sequences and the nucleic acid sequences taught herein are preferably isolated.

The xylanase of the present invention is preferably a GH10 xylanase. In other words the xylanase may have a molecular weight in the range of 32-39 kDa and/or the catalytic domain of the xylanase consists of an eightfold β/α barrel structure (as taught in Harris et al 1996-Acta. Crystallog. Sec. D 52, 393-401).

In one aspect, the present invention provides a composition comprising a xylanase enzyme comprising (or consisting of) a polypeptide sequence shown herein as SEQ ID No. 1, SEQ ID No. 2 or SEQ ID No. 3 or a variant, homologue, fragment or derivative thereof having at least 98.5% (e.g. at least 98.8 or 99 or 99.1 or 99.5%) identity with SEQ ID No. 1 or SEQ ID No. 2 or SEQ ID No. 3 or a xylanase which is encoded by a nucleotide sequence shown herein as SEQ ID No. 4, SEQ ID No. 5 or SEQ ID No. 6, or a nucleotide sequence which has at least 97.7% (e.g. at least 98%, 98.5% or 99%) identity with SEQ ID No. 4, SEQ ID No. 5 or SEQ ID No. 6.

In one aspect, the xylanase enzyme for use in the methods and uses of the present invention comprises (or consists of) a polypeptide sequence shown herein as SEQ ID No. 1, SEQ ID No. 2, SEQ ID No. 3, SEQ ID No. 9, SEQ ID No. 10, SEQ ID No. 11, or SEQ ID No. 15 or a variant, homologue, fragment or derivative thereof having at least 75% (suitably at least 85% or at least 90% or at least 99%) identity with SEQ ID No. 1 or SEQ ID No. 2 or SEQ ID No. 3 or SEQ ID No. 9 or SEQ ID No. 10 or SEQ ID No. 11 or SEQ ID No. 15, or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14. SEQ ID No. 16, SEQ ID No. 17 or SEQ ID No. 18, or a nucleotide sequence which has at least 75% (suitably at least 85%, or at least 90% or at least 98%) identity with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

In one aspect, the xylanase enzyme for use in the methods and uses of the present invention comprises (or consists of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15 or a variant, homologue, fragment or derivative thereof having at least 85% identity with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 or a nucleotide sequence which has at least 85% identity with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

In one aspect, the xylanase enzyme for use in the methods and uses of the present invention comprises (or consists of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15 or a variant, homologue, fragment or derivative thereof having at least 90% identity with SEQ ID No. 1 or SEQ ID No. 2 or SEQ ID No. 3 or SEQ ID No. 9 or SEQ ID No. 10 or SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6. SEQ ID No. 12, SEQ ID No. 13, SEQ ID No. 14, SEQ ID No. 16, SEQ ID No. 17 or SEQ ID No. 18 or a nucleotide sequence which has at least 90% identity with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

In one aspect, the xylanase enzyme for use in the methods and uses of the present invention comprises (or consists of) a polypeptide sequence shown herein as SEQ ID No. 1, SEQ ID No. 2, SEQ ID No. 3, SEQ ID No. 9, SEQ ID No. 10. SEQ ID No. 11 or SEQ ID No. 15 or a variant, homologue, fragment or derivative thereof having at least 99% identity with SEQ ID No. 1 or SEQ ID No. 2 or SEQ ID No. 3 or SEQ ID No. 9 or SEQ ID No. 10 or SEQ ID No. 11 or SEQ ID No. 15, or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which has at least 98% identity with SEQ ID No. 4, SEQ ID No. 5, SEQ ID No. 6. SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

In one embodiment the xylanase enzyme of the present invention may be referred to herein as FveXyn4 (this term refers to the active protein. e.g. the mature protein).

In one embodiment the xylanase enzyme of the present invention may be referred to herein as FoxXyn2 (this term refers to the active protein, e.g. the mature protein).

In one embodiment preferably the xylanase is a fungal xylanase.

In one embodiment preferably the xylanase is a GH10 xylanase.

In one embodiment preferably the xylanase is a fungal GH10 xylanase.

In one embodiment preferably the xylanase in an endoxylanase, e.g. an endo-1,4-β-d-xylanase. The classification for an endo-1,4-β-d-xylanase is E.C. 3.2.1.8.

Preferably the xylanase of the present invention has an optimum pH at about 6.

Preferably the xylanase of the present invention retains greater than 70% of maximum activity between pH 4.6 and 7, preferably between 5.1 and 7.

Without wishing to be bound by theory, pH may also have an important effect on enzyme efficacy and efficiency. For feed applications in particular the pH profile of the xylanases of the present invention favour activity in the small intestine, under neutral conditions.

Preferably the xylanase of the present invention has an optimum temperature of about 60° C.

Preferably the xylanase of the present invention retains greater than 70% of maximum activity between 45° C. and 64° C.

In one embodiment, the xylanases according to the present invention is capable of degrading (or degrades) a xylan-containing material, particularly arabinoxylans, particularly isoluble arabinoxylans (AXinsol).

In another embodiment the xylanases according to the present invention is capable of degrading (or degrades) soluble polymers (e.g. oligomers) that are produced from degradation of AXinsol or that are (naturally) present in grain-based material.

In a further embodiment the xylanases according the present invention is capable of degrading (or degrades) both a xylan-containing material, particularly arabinoxylans, particularly AXinsol, and soluble polymers (e.g. oligomers) that are produced from degradation of AXinsol.

In one embodiment the xylanases of the present invention are unaffected by wheat xylanases inhibitors, e.g. proteinaceous inhibitors, e.g TAXI-like proteinaceous inhibitors in wheat. Prior art fungal xylanases can be inhibited by as much as 70-95% by wheat proteinaceous inhibitors. Preferably the xylanases of the present invention are only inhibited by 20-30% at most in wheat applications.

TAXI are *Triticum aestivum* xylanases inhibitors, present in cereals.

The term "consisting essentially of as used herein means that unspecified components may be present if the characteristics of the claimed composition are thereby not materially affected.

The term "consisting of means that the proportions of the specific ingredients must total 100%.

The term "comprising" used herein may be amended in some embodiments to refer to consisting essentially of or consisting of (both having a more limited meaning that "comprising").

In one embodiment the insoluble arabinoxylan containing material is not wheat straw.

Uses

The xylanase of the present invention can be suitably used in any one of the following applications:
a) An additive in animal feedstuffs; and/or
b) A feed supplement for an animal; and/or
c) Breakdown of grain-based material (e.g. this can be whole grain or part of grain). The breakdown products (e.g. glucose) can be used as a feedstock for any fermentation process, such as in biofuel (e.g. bioethanol) production or in the production of other products such as biochemicals (e.g., bio-based isoprene). Therefore in one embodiment the present invention relates to the production of biofuel (e.g. bioethanol) and to the enhanced utilisation of grain-based material in the biofuel industry; and/or
d) Cereal (e.g. wheat) gluten-starch separation industry. The resultant product(s) may be starch (e.g. purified starch) and/or gluten and/or fibres and/or water solubles (such as soluble pentosans). In one embodiment the present invention relates to the production of starch and/or gluten; and/or
e) Improving malting and brewing, e.g. by breaking down grain-based material (e.g. malted barley).

In one embodiment the xylanase of the present invention is used in a feedstuff. Preferably a feedstuff comprising corn or is a corn-based feedstuff.

In one embodiment the xylanase of the present invention is used in malting or brewing.

In a further embodiment the xylanase of the present invention is used in wheat gluten-starch separation.

In a yet further embodiment the xylanase of the present invention is used in the breakdown of grain-based material and may be part of the biofuel (e.g. bioethanol) production process.

For the avoidance of doubt, SEQ ID No. 3 is the mature form of SEQ ID No. 1 or SEQ ID No. 2.

Likewise, SEQ ID No. 11 is the mature form of SEQ ID No. 9 or SEQ ID No. 10.

Advantages

The novel xylanase taught herein has many advantages compared with known xylanases.

The xylanases as taught herein and of the present invention are unexpectedly good at solubilising pentosans.

The xylanases as taught herein and of the present invention are unexpectedly good at solubilising AXinsol.

Surprisingly it has been found that the xylanase of the present invention is particularly good at degrading xylan-containing materials, such as arabinoxyians, e.g. AXinsol, in a broad spectrum of substrates, corn, wheat, DDGS, etc, in particular corn and corn based substrates, in particular both wheat (including wheat-based) products and corn (including corn-based products). Compared with the benchmark xylanases which are all commercially produced and marketed xylanases, the novel xylanase taught herein was capable of much more efficient degradation and pentosan release from more plant based materials (in particular corn-based substrates) compared with the marketed xylanases. This was completely unexpected. This contrasts with prior-known enzymes, which are often inferior at solubilising AXinsol in corn or corn-based substrates or which are not as efficient in both wheat- and corn-based substrates.

In addition, the enzyme of the present invention is particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol) a reduction in viscosity is obtained. This latter effect is essential in some of the claimed applications.

Typically, conventional xylanases may breakdown AXinsol, but will lead to an increase is the polymer production products which will lead to an increase in viscosity of the mixture. This increased viscosity is disadvantageous in many applications.

The enzymes of the present invention and as described herein have been found to not only breakdown (solubilise) insoluble arabinoxylans (AXinsol) from a wide range of substrates, including corn, wheat, DDGS, etc, in particular corn and corn-based substrates, in particular both wheat (including wheat-based) products and corn (including corn-based products), but also efficiently breakdown the thus solubilised polymers to ensure viscosity is not raised and/or to reduce viscosity.

The xylanases of the present invention and as described herein are capable of degrading AXsol or the breakdown products of AXinsol to ensure viscosity is not increased and/or viscosity is reduced in the reaction mixture.

Many of the xylanases commercialized for use in feedstuffs for solubilizing pentosans are GH11 enzymes. It had been considered by those skilled in the art that GH10 xylanases were not as strong at solubilizing pentosans, particularly AXinsol, compared with GH11 xylanases. Surprisingly it has been found that the novel xylanase disclosed herein which is a GH10 xylanase is particularly good at solubilizing AXinsol in a broad spectrum of substrates, including corn based substrates. Surprisingly, the present inventors have found that the GH10 xylanases of the present invention (and taught herein) outperform commercial GH11 xylanases in their ability to solubilize pentosans.

The fact that the present enzymes efficiently solubilize AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-soy diet for example.

It was completely unexpected for a GH10 xylanase to be so good on solubilizing AXinsol in cereals, particularly in corn or corn-based substrates.

The enzymes of the present invention are able to efficiently (and quickly) degrade the polymers and/or oligomers that are produced from solubilisation of AXinsol or that are present in grain-based materials. This leads to an unexpected advantage for the GH10 xylanases taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g., bio-based isoprene); or in the wheat gluten-starch separation industry for the production of starch for example.

Notably it has been found that the degradation product on average is shorter for the GH10 enzymes tested herein compared with GH11 enzymes. This enhances the lowering of viscosity effect.

In addition, a further advantage of the GH10 xylanases of the present invention (unlike many GH11 xylanases) are unaffected by wheat xylanase inhibitors, e.g. TAXI like proteinaceous inhibitors, which occur in wheat.

One advantage of the present invention is that it improves wheat gluten-starch separation.

The enzyme of the present invention is particularly effective at enhancing the performance of a subject or improving the digestibility of a raw material in a feed and/or for improving feed efficiency in a subject.

Xylan-Containing Material

The xylanase of the present invention (or composition comprising the xylanase of the present invention) may be used to degrade any xylan-containing material.

In one embodiment the xylan-containing material is any plant material comprising arabinoxylan.

In one embodiment the xylan-containing material is any plant material comprising insoluble arabinoxylan (AXinsol).

In one embodiment the xylan-containing material is a feedstuff or feed component.

In one embodiment the xylan-containing material is a grain-based material (including whole grains or partial grains or malted grains, e.g. malted barley). When the method relates to biofuel production (e.g. bioethanol production) then preferably the xylan-containing material is a grain-based material.

In another embodiment the xylan-containing material may be a barley malt or mash, or malted barley or combinations thereof.

In a yet further embodiment the xylan-containing material may be a cereal flour (e.g. wheat, oat, rye or barley flour). When the method relates to a gluten-starch separation process preferably the xylan-containing material is a cereal flour (e.g. wheat oat, rye or barley flour).

Breakdown or Degradation

The enzyme (or composition comprising the enzyme) of the present invention or as disclosed herein may be used to breakdown (degrade) AXinsol or AXsol or degradation products of AXinsol.

The term "breakdown" or "degrade" in synonymous with hydrolyses.

Solubilisation/Degradation

The present invention relates to a method of degrading a xylan-containing material (preferably an arabinoxylan-containing material, preferably an insoluble arabinoxylan (AXinsol)-containing material) to produce soluble pentosans (which can be polymeric, oligomeric or monomeric).

This method may be described herein as pentosan solubilisation or arabinoxylan solubilisation or AXinsol solubilisation or degradation of AXinsol.

In one embodiment, the present invention relates to a method of degrading (or breaking down) insoluble arabinoxylan (AXinsol). This can also be referred to as solubilisation of insoluble arabinoxylan and/or solubilisation of pentosans.

In a further embodiment of the present invention the method relates to degrading (e.g. breaking down) polymers derived from the degradation of insoluble arabinoxylans.

Arabinoxylan (AX)

The term "arabinoxylans" (AX) as used herein means a polysaccharide consisting of a xylan backbone (1,4-linked xylose units) with L-arabinofuranose (L-arabinose in its 5-atom ring form) attached randomly by $1\alpha\rightarrow2$ and/or $1\alpha\rightarrow3$ linkages to the xylose units throughout the chain. Arabinoxylan is a hemicellulose found in both the primary and secondary cell walls of plants. Arabinoxylan can be found in the bran of grains such as wheat, maize (corn), rye, and barley. Arabinoxylan (AX) is found in close association with the plant cell wall, where it acts as a glue linking various building blocks of the plant cell wall and tissue, give it both structural strength and rigidity.

The term "pentosan" as used herein is any of a group of carbohydrates which yield pentoses on complete hydrolysis.

Since xylose and arabinose (the constituents of arabinoxylans) are both pentoses, arabinoxylans are usually classified as pentosans.

AX is the principal Non Starch Polysaccharide (NSP)-fraction in several of the most important feed raw material, including wheat and corn.

Its abundance, location within vegetable material and molecular structure cause AX to have a severe, negative impact on feed digestibility, effectively reducing the nutritional value of the raw materials in which it is present. This makes AX an important anti-nutritional factor, reducing animal production efficiency.

In addition AX can have a severe, negative impact when trying to breakdown plant material for example in processes such as brewing, malting, biofuel manufacture, effectively reducing the amount of substrate accessible in the raw plant material.

AXs can also hold substantial amounts of water (which can be referred to as their water holding capacity)—this can cause soluble arabinoxylans to result in (high) viscosity—which is a disadvantage in many applications.

The term "Hemicellulose"—as used herein means the polysaccharide components of plant cell walls other than cellulose. The term "hemicellulose" as used herein may mean polysaccharides in plant cell walls which are extractable by dilute alkaline solutions. Hemicelluloses comprise almost one-third of the carbohydrates in woody plant tissue. The chemical structure of hemicelluloses consists of long chains of a variety of pentoses, hexoses, and their corresponding uronic acids. Hemicelluloses may be found in fruit, plant stems, and grain hulls. Xylan is an example of a pentosan consisting of D-xylose units with $1\beta\rightarrow4$ linkages.

Water Insoluble Arabinoxylan (AXinsol)

Water-insoluble arabinoxylan (AXinsol) also known as water-unextractable arabinoxylan (WU-AX) constitutes a significant proportion of the dry matter of plant material.

In wheat AXinsol can account for 6.3% of the dry matter. In wheat bran and wheat DDGS AXinso6 can account for about 20.8% or 13.4% of the dry matter (w/w).

In rye AXinsol can account for 5.5% of the dry matter.

In corn AXinsol can account for 3.5-6% (e.g. 5.1%) of the dry matter. In corn DDGS AXinsol can account for 10-20% (e.g. 12.6%) of the dry matter.

AXinsol causes nutrient entrapment in feed. Large quantities of well digestible nutrients such as starch and proteins remain either enclosed in clusters of cell wall material or bound to side chains of the AX. These entrapped nutrients will not be available for digestion and subsequent absorption in the small intestine.

Water-Soluble Arabinoxylan (AXsol)

Water-soluble arabinoxylan (AXsol) also known as water extractable arabinoxylan (WE-AX) can cause problems in biofuel production and/or malting and/or brewing and/or in feed as they can cause increased viscosity due to the water-binding capacity of AXsol.

In feed AXsol can have an anti-nutritional effect particularly in monogastrics as they cause a considerable increase of the viscosity of the intestinal content, caused by the extraordinary water-binding capacity of AXsol. The increase viscosity can affect feed digestion and nutrient use as it can prevent proper mixing of feed with digestive enzymes and bile salts and/or it slows down nutrient availability and absorption and/or it stimulates fermentation in the hindgut.

In wheat AXsol can account for 1.8% of the dry matter. In wheat bran and wheat DDOS AXsol can account for about 1.1% or 4.9% of the dry matter (w/w).

In rye AXsol can account for 3.4% of the dry matter.

In barley AXsol can account for 0.4-0.8% of the dry matter.

In corn AXsol can account for 0.1-0.4% (e.g. 0.1%) of the dry matter. In corn DDGS AXinsol can account for 0.3-2.5% (e.g. 0.4%) of the dry matter.

In addition, however, to the amount of AXsol present in plant material, when a xylanase solubilises AXinsol in the plant material this can release pentosans and/or oligomers which contribute to AXsol content of the plant material.

One significant advantage of the xylanases disclosed herein is that they have the ability to solubilise AXinsol without increasing viscosity. It is presently believed that high molecular weight products are not formed A breakdown of AXsol can decrease viscosity.

A breakdown of AXsol can release nutrients.

Viscosity

The present invention can be used to ensure that the viscosity is not increased and/or to reduce viscosity in any process where the water-binding capacity of AXsol causes an undesirable increase in viscosity.

The present invention relates to ensuring that viscosity is not increased and/or to reducing viscosity by breaking down (degrading) AXsol or by breaking down (degrading) the polymers and/or oligomers produced by solubilising AXinsol.

Without wishing to be bound by theory, by being able to efficiently (quickly) breakdown (degrade) the solubilized polymers (e.g. oligomers) obtained from dissolving AXinsol an undesirable increase in viscosity can be avoided and/or a reduction in viscosity can be obtained. The term "efficiently" as used herein means that the enzyme is capable of degrading the polymers (e.g. oligomers) being formed by solubilisation of the AXinsol faster than the speed with which the AXinsol is degraded (or solubilized).

Reducing viscosity has advantages in many applications as taught herein.

An in vitro assay which attempts to mimic the environment in the small intestine of a chicken was originally described by Bedford & Classen (1993 Poultry Sci., 72, 137-143). The assay consists of a two steps incubation of the feed first at low pH with pepsin followed by incubation with pancreatin at neutral pH. It is generally accepted that the viscosity of the supernatant after end incubation correlates with the viscosity created in vivo in broilers.

Without increasing viscosity and/or a reduction in viscosity as taught herein for feed applications means that addition of the xylanase will result in an unchanged or lower viscosity measured by the method described in Example 7. By unchanged it is meant that the measured value, being the average of three repetitions, falls within two standard deviation of the measured value for a wheat sample without xylanase addition.

Viscosity can be measured using the following devices: Rapid ViscoAnalyzer (RVA) (e.g in bioethanol processing) and Haake VT550 viscometer (Thermofisher) (e.g. is wheat-gluten starch processing). Both devices can monitor viscosity profiles of fuel ethanol processes and wheat starch separation processes, of which the experimental conditions are taught in Example 8 and 9, respectively.

In the present invention a reduction in viscosity can be calculated by comparing one sample comprising the xylanase of the present invention (or taught herein) compared with another comparable sample without the xylanase of the present invention (or taught herein).

Comparing the viscosity reduction profiles of the xylanase of the present invention with those of the market benchmark xylanase(s) demonstrates the enzyme performance. The aim is to improve enzyme performance compared to the market benchmark. The benchmark enzyme(s) for the individual applications are provided in the examples below.

The benchmark enzyme for feed applications is Econase® XT.

The benchmark enzyme for bioethanol processing is Xylathin™.

The benchmark enzyme for wheat-gluten starch separation is Shearzyme Plus™ In one embodiment of the present invention the xylanases taught herein are viscosity reducers.

Generally, wheat (or other cereal) is first dry-milled to separate the bran and germ from the endosperm, which is ground into flour. This endosperm flour is then further fractionated through a wheat starch separation process into several product streams of varying commercial value. The major aim is to produce a refined grade of A-starch, consisting of large, lenticular granules of 15-40 μm. The second stream B-starch consists of less purified starch granules, which are spherical and small (1-10 μm). (C. C. Maningat, P. A. Seib, S. D. Bassi, K. S. Woo, G. D. Lasater, Chapter 10 from the book "*Starch*" (2009) 441-451, *Wheat starch: production, properties, modification and uses*). Isolated wheat starch forms the starting material for modified starch production with applications in both food- and nonfood-applications. Vital gluten is the third product of added-value in wheat separation processes. The vitality of the isolated wheat gluten is determined by the ability to form viscoelastic networks, required for breadmaking. Vital gluten encapsulate the carbon dioxide formed in dough preparation during baking, and consequently increase the bread volume. (Anne van der Borght, Hans Goesaert, Wim S. Veraverbeke, Jan A. Delcour, *Journal of Cereal Science* 41 (2005) 221-237, *Fractionation of wheat and wheat flour into starch and gluten: overview of the main processes and the factors involved*.) It is therefore often used to enrich flours for bread making, to achieve improved bread products. Other markets for gluten include as an additive in vegetarian, meat, fish or poultry products, including those in pet-food industry; in cereal breakfast; or in soy sauce. Due to its thermoplasticity and good film-forming properties, gluten is also used in non-food markets as adhesives. (L Day, M. A. Augustin, L. L Batey, C. W. Wrigley, *Trends in Food Science & Technology* 17 (2006) 82-90, *Wheat-gluten uses and industry needs*).

The xylanases taught herein can be used to reduce the viscosity (or not increase viscosity) in processes for separating cereal flour (e.g. wheat, oat, rye or barley flour) into starch and gluten fractions and to improve the separation by degrading oligosaccharides that hinder gluten agglomeration.

Wort viscosity, and the viscosity of barley mash and barley malt in brewing and malting can cause significant disadvantages during brewing and/or malting. The present invention relates to reducing the viscosity (or not increase the viscosity) of wort, barley mash, barley malt or a combination thereof.

Feed or Feedstuff

The enzyme or feed additive composition of the present invention may be used as—or in the preparation of—a feed.

The term "feed" is used synonymously herein with "feedstuff".

Preferably the arabinoxylan-containing material of the present invention is a feedstuff, or a constituent of a feedstuff, or a feed component.

The feed may be in the form of a solution or as a solid or as a semi-solid—depending on the use and/or the mode of application and/or the mode of administration.

When used as—or in the preparation of—a feed—such as functional feed—the enzyme or composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the enzyme or feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term "fodder" as used herein means any food which is provided to an animal (rather than the animal having to forage for it themselves). Fodder encompasses plants that have been cut.

The term fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grain (DDG) (particularly corn based Distillers Dried Grain (cDDG)), Distillers Dried Grain Solubles (DDGS) (particularly corn based Distillers Dried Grain Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

In one embodiment the feedstuff comprises or consists of corn, DDGS (such as cDDGS), wheat, wheat bran or a combination thereof.

In one embodiment the feed component may be corn, DDGS (e.g. cDDGS), wheat, wheat bran or a combination thereof.

In one embodiment the feedstuff comprises or consists of corn, DDGS (such as cDDGS) or a combination thereof.

In one embodiment a feed component may be corn, DDGS (such as cDDGS) or a combination thereof.

A feedstuff of the present invention may contain at least 30%, at least 40%, at least 50% or at least 60% by weight corn and soybean meal or corn and full fat soy, or wheat meal or sunflower meal.

A feedstuff of the present invention may contain between about 5 to about 40% corn DDGS. For poultry—the feedstuff on average may contain between about 7 to 15% corn DDGS. For swine (pigs)—the feedstuff may contain on average 5 to 40% corn DDGS.

A feedstuff of the present invention may contain corn as a single grain, in which case the feedstuff may comprise between about 35% to about 80% corn.

In feedstuffs comprising mixed grains, e.g. comprising corn and wheat for example, the feedstuff may comprise at least 10% corn.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, corn gluten feed, wet-cake, Distillers Dried Grain (DDG), Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wet-cake, Distillers Dried Grain (DDG)—particularly cDDG, wheat bran, and wheat for example.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wheat bran, and wheat for example.

In the present invention the feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" in the present invention encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term "feed" in the present invention encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

The term "feed" in the present invention encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the enzyme (or composition comprising the enzyme) of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The enzyme (or composition comprising the enzyme) of the present invention may be applied to intersperse, coat and/or impregnate a product (e.g. feedstuff or raw ingredients of a feedstuff) with a controlled amount of said enzyme.

Preferably, the enzyme (or composition comprising the enzyme) of the present invention will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme that was present/active in the additive before heating to the specified temperature is still present/active after it cools to room temperature. Preferably, at least about 80% of the enzyme that is present and active in the additive before heating to the specified temperature is still present and active after it cools to room temperature.

In a particularly preferred embodiment the enzyme (or composition comprising the enzyme) of the present invention is homogenized to produce a powder.

In an alternative preferred embodiment, the enzyme (or composition comprising the enzyme) of the present invention is formulated to granules as described in WO2007/044968 (referred to as TPT granules) or WO1997/016076 or WO1992/012645 incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme.

Preferably, the salt used for the salt coating has a water activity greater than 0.25 or constant humidity greater than 60% at 20° C.

Preferably, the salt coating comprises a $Na_2SO_4$.

The method of preparing an enzyme (or composition comprising the enzyme) of the present invention may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

It will be understood that the enzyme (or composition comprising the enzyme) of the present invention is suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), and swine (all age categories), a ruminant such as cattle (e.g. cows or bulls (including calves)), horses, sheep, a pet (for example dogs, cats) or fish (for example agastric fish, gastric fish, freshwater fish such as salmon, cod, trout and carp, e.g. koi carp, marine fish such as sea bass, and crustaceans such as shrimps, mussels and scallops). Preferably the feedstuff is for poultry.

Corn Based Feedstuff

In a preferred embodiment the feedstuff may be a corn based feedstuff. The term "corn based feedstuff" as used herein means a feedstuff which comprises or consists of corn (maize) or a by-product of corn.

Preferably the corn based feedstuff comprises corn or a by-product of corn as the major constituent. For example the corn based feedstuff may comprise at least 35% corn or a by-product of corn, such as at least 40% corn or a by-product of corn, such as at least 50% corn or a by-product of corn, such as at least 60% corn or a by-product of corn, such as at least 70% corn or a by-product of corn, such as at least 80% or a by-product of corn, such as at least 90% corn or a by-product of corn, for example 100% corn or a by-product of corn.

In some embodiments the corn based feedstuff may comprise corn or a by-product of corn as a minor constituent; in which case the feedstuff may be supplemented with corn or a byproduct of corn. By way of example only the feedstuff may comprise for example wheat supplemented with corn or a by-product of corn.

When corn or the by-product of corn is a minor constituent of the feedstuff, the corn or by-product of corn is at least 5%, preferably at least 10%, preferably at least 20%, preferably at least 30% of the feedstuff.

For the avoidance of doubt the term "corn" as used herein is synonymous with maize, e.g. *Zea mays*.

In one embodiment the by-product of corn may be corn Distillers Dried Grain Solubles (cDDGS) or corn wet-cake or corn Distillers Dried Grain (DDG) or corn gluten meal or corn gluten feed or combinations thereof.

In one embodiment preferably the arabinoxylan-containing material of the present invention comprises a by-product of corn, such as corn Distillers Dried Grain Solubles (cDDGS) or corn wet-cake or corn Distillers Dried Grain (DDG) or corn gluten meal or corn gluten feed or combinations thereof.

Wheat Based Feedstuff

In a preferred embodiment the feedstuff may be a wheat based feedstuff. The term "wheat based feedstuff" as used herein means a feedstuff which comprises or consists of wheat or a by-product of wheat.

Preferably the wheat based feedstuff comprises wheat or a by-product of wheat as the major constituent. For example the wheat based feedstuff may comprise at least 40% wheat or a by-product of wheat, such as at least 60% wheat or a by-product of wheat, such as at least 80% or a by-product of wheat, such as at least 90% wheat or a by-product of wheat, for example 100% wheat or a by-product of wheat.

In some embodiments the wheat based feedstuff may comprise wheat or a by-product of wheat as a minor constituent; in which case the feedstuff may be supplemented with wheat or a by-product of wheat. By way of example only the feedstuff may comprise for example wheat supplemented with wheat or a by-product of wheat.

When wheat or the by-product of wheat is a minor constituent of the feedstuff, the wheat or by-product of wheat is at least 5%, preferably at least 10%, preferably at least 20%, preferably at least 30% of the feedstuff.

In one embodiment the by-product of wheat may be wheat bran, wheat middlings, wheat fibres for example.

Bran is the hard outer layer of grain and consists of combined aleurone and pericarp. Along with germ, it is an integral part of whole grains, and is often produced as a by-product of milling in the production of refined grains. When bran is removed from grains, the grains lose a portion of their nutritional value. Bran is present in and may be milled from any cereal grain, including rice, corn (maize), wheat, oats, barley and millet. Bran is particularly rich in dietary fiber and essential fatty acids and contains significant quantities of starch, protein, vitamins and dietary minerals.

Wheat middlings is coarse and fine particles of wheat bran and fine particles of wheat shorts, wheat germ, wheat flour and offal from the "tail of the mill".

Wheat middlings is an inexpensive by-product intermediate of human food and animal feed. In one embodiment preferably the arabinoxylan-containing material of the present invention comprises wheat bran and/or wheat middlings.

Wet-Cake, Distillers Dried Grains (DDG) and Distillers Dried Grain Solubles (DDGS)

Wet-cake, Distillers Dried Grains and Distillers Dried Grains with Solubles are products obtained after the removal of ethyl alcohol by distillation from yeast fermentation of a grain or a grain mixture by methods employed in the grain distilling industry.

Stillage coming from the distillation (e.g. comprising water, remainings of the grain, yeast cells etc.) is separated into a "solid" part and a liquid part.

The solid part is called "wet-cake" and can be used as animal feed as such.

The liquid part is (partially) evaporated into a syrup (solubles).

When the wet-cake is dried it is Distillers Dried Grains (DDG).

When the wet-cake is dried together with the syrup (solubles) it is Distillers Dried Grans with Solubles (DDGS).

Wet-cake may be used in dairy operations and beef cattle feedlots.

The dried DDGS may be used in livestock, e.g. dairy, beef and swine) feeds and poultry feeds.

Corn DDGS is a very good protein source for dairy cows.

Corn Gluten Meal

In one aspect, the by-product of corn may be corn gluten meal (CGM).

CGM is a powdery by-product of the corn milling industry. CGM has utility in, for example, animal feed. It can be used as an inexpensive protein source for feed such as pet food, livestock feed and poultry feed. It is an especially good source of the amino acid cysteine, but must be balanced with other proteins for lysine.

Feed Additive Composition

The feed additive composition of the present invention and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions of the present invention may be mixed with feed or administered in the drinking water.

In one aspect the present invention relates to a method of preparing a feed additive composition, comprising admixing a xylanase as taught herein with a feed acceptable carrier, diluent or excipient, and (optionally) packaging.

Premix

The feedstuff and/or feed additive composition may be combined with at least one mineral and/or at least one vitamin. The compositions thus derived may be referred to herein as a premix.

Malting and Brewing

The enzyme (or composition comprising the enzyme) of the present invention may be used in malting and brewing.

Barley grains contain 1.7 to 4.1% (w/w) water-extractable and 3.6 to 6.4% (w/w) total beta-glucan (Anderson, M. A., Cook, J. A., & Stone, B. A., Journal of the Institute of Brewing, 1978, 84, 233-239; Henry, J., Journal of the Science of Food and Agriculture, 1985, 36, 1243).

Wheat grains contain 0.1 to 0.8% (w/w) water-extractable and 0.6 to 1.4% (w/w) total beta-glucan (Anderson, M. A. et al (1978) supra).

Efficient hydrolysis of arabinoxylans (AXsol) and beta-glucan is important because such compounds can be involved in production problems such as wort viscosity (Ducroo, P. & Frelon, P. G., Proceedings of the European Brewery Convention Congress, Zurich, 1989, 445; Vietor, R. J. & Voragen, A. G. J., Journal of the Institute of Brewing, 1993, 99, 243) and filterability and haze formation (Coote, N. & Kirsop. B. H. 1976. Journal of the Institute of Brewing, 1976, 82, 34; Izawa, M., Kano, Y. & Kanimura, M. 1991. Proceedings Aviemore Conference on Malting, brewing and Distillling, 1990, 427).

The present invention provides a method of hydrolysing arabinoxylans (e.g. AXinsol and AXsol) during malting and brewing wherein wheat grains, barley grains or a combination thereof, or portions of the wheat and/or barley grains, are admixed with the enzyme of the present invention.

In one aspect of the present invention may relate to a food composition that is a beverage, including, but not limited to, a fermented beverage such as beer and wine, comprising a xylanase comprising (or consisting of) a polypeptide sequence shown herein as SEQ ID No. 1, SEQ ID No. 2, SEQ ID No. 3, SEQ ID No. 9, SEQ ID No. 10, SEQ ID No. 11 or SEQ ID No. 15, or a variant, homologue, fragment or derivative thereof having at least 75% identity (such as at least 80%, 85%, 90%, 95%, 98% or 99% identity) with SEQ ID No. 1 or SEQ ID No. 2, SEQ ID No. 3, SEQ ID No. 9, SEQ ID No. 10, SEQ ID No. 11 or SEQ ID No. 15; or a polypeptide sequence which comprises SEQ ID No. 1, SEQ ID No. 2, SEQ ID No. 3, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity (such as at least 80%, 85%, 90%, 95% or 98% identity) with SEQ ID No. 4, SEQ ID No. 5, SEQ ID No. 6, SEQ ID No. 12, SEQ ID No. 13, SEQ ID No. 14, SEQ ID No. 16, SEQ ID No. 17 or SEQ ID No. 18; or a nucleotide sequence which differs from SEQ ID No. 4 or SEQ ID No. 5 or SEQ ID No. 6 or SEQ ID No. 12 or SEQ ID No. 13 or SEQ ID No. 14 or SEQ ID No. 16 or SEQ ID No. 17 or SEQ ID No. 18 due to the degeneracy of the genetic code.

In another aspect of the present invention may relate to a food composition that is a beverage, including, but not limited to, a fermented beverage such as beer and wine, comprising a xylanase enzyme comprising (or consisting of) a polypeptide sequence shown herein as SEQ ID No. 1, SEQ ID No. 2 or SEQ ID No. 3 or a variant, homologue, fragment or derivative thereof having at least 98.5% (e.g. at least 98.8 or 99 or 99.1 or 99.5%) identity with SEQ ID No. 1 or SEQ ID No. 2 or SEQ ID No. 3 or a xylanase which is encoded by a nucleotide sequence shown herein as SEQ ID No. 4, SEQ ID No. 5 or SEQ ID No. 6, or a nucleotide sequence which has at least 97.7% (e.g. at least 98%, 98.5% or 99%) identity with SEQ ID No. 4, SEQ ID No. 5 or SEQ ID No. 6.

In the context of the present invention, the term "fermented beverage" is meant to comprise any beverage produced by a method comprising a fermentation process, such as a microbial fermentation, such as a bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, corn (maize), potato, tapioca, cassava and syrups, such as corn syrup, sugar cane syrup, inverted sugar syrup, barley and/or wheat syrups, and the like may be used as a source of starch.

As used herein, the term "mash" refers to an aqueous slurry of any starch and/or sugar containing plant material such as grist, e. g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

In another aspect the invention relates to a method of preparing a fermented beverage such as beer comprising mixing the xylanase of the present invention with malt or adjunct.

Examples of beers comprise: full malted beer, beer brewed under the "Reinheitsgebot", ale, IPA, lager, bitter. Happoshu (second beer), third beer, dry beer, near beer, light beer, low alcohol beer, low calorie beer, porter, bock beer, stout, malt liquor, non-alcoholic beer, nonalcoholic malt liquor and the like, but also alternative cereal and malt beverages such as fruit flavoured malt beverages, e. g. citrus flavoured, such as lemon-, orange-, lime-, or berry-flavoured malt beverages, liquor flavoured malt beverages, e. g., vodka-, rum-, or tequila-flavoured malt liquor, or coffee flavoured malt beverages, such as caffeine-flavoured malt liquor, and the like.

Breakdown of Grain-Based Material e.g. for Biofuel Production

The enzyme (or composition comprising the enzyme) of the present invention or as disclosed herein may be used to breakdown (degrade) AXinsol and AXsol during grain processing from e.g. grain-based material. The grain-based material may be whole grains (e.g. whole wheat, barley, rye, triticale or corn grains or mixtures thereof) or portions of the whole grains, or mixtures thereof.

In one embodiment the enzyme (or composition comprising the enzyme) of the present invention or as disclosed herein may be used to breakdown (degrade) AXinsol and AXsol in grain-based materials or whole grains.

For the avoidance of doubt the whole grains can be mechanically broken.

The grain-based material may be broken down or degraded to glucose. The glucose may subsequently be used as a feedstock for any fermentation process, e.g. for biofuel (e.g. bioethanol) production and/or biochemicals (e.g., bio-based isoprene) production.

The grain-based material may be feedstock for a biofuel (e.g. bioethanol) production process.

Today most fuel ethanol is produced from corn (maize) grain, which is milled, treated with amylase enzymes to hydrolyse starch to sugars, fermented, and distilled. While substantial progress has been made in reducing costs of ethanol production, substantial challenges remain. Improved techniques are still needed to reduce the cost of biofuel feedstocks for ethanol production. For example, in grain-based ethanol production degradation of arabinoxylans may increase accessibility of starch.

The present invention provides a xylanase for use in the breakdown of hemicelluloses, e.g. arabinoxylan—particularly AXinsol and AXsol.

By way of example only, in the European fuel alcohol industry, small grains like wheat, barley and rye are common raw materials, in the US corn is mainly used. Wheat, barley and rye contain, next to starch, high levels of non-starch polysaccharide polymers (NSP), like cellulose, beta-glucan and hemicellulose.

The ratio in which the different NSPs are represented differ for each feedstock. The table below shows the different amounts of NSPs in wheat, barley and rye compared to some other feedstocks.

TABLE 1

Non-starch Polysaccharides present in different feedstocks (g kg$^{-1}$ dry matter)

|  | Corn | Wheat | Rye | Barley Hulled | Barley Hulless | Oats Hulled | Oats Hulless |
|---|---|---|---|---|---|---|---|
| Beta-Glucan | 1 | 8 | 16 | 42 | 42 | 28 | 41 |
| Cellulose | 22 | 17-20 | 15-16 | 43 | 10 | 82 | 14 |
| Soluble and Non-soluble NCP[1] | 75 | 89-99 | 116-136 | 144 | 114 | 150 | 113 |
| Total NSP | 97 | 107-119 | 132-152 | 186 | 124 | 232 | 116 |

[1]Non Cellulosic polysaccharides: pentosans, (arabino)xylans and other hemicelluloses NSPs can give high viscosity to grain mashes due to their large water-binding capacity. High viscosity has a negative impact on ethanol production since it will limit the solid concentration that can be used in mashing and it will reduce the energy efficiency of the process. In addition, residual hemicelluloses present throughout the process may contribute to fouling in heat exchangers and distillation equipment. The largest impact of a high viscosity is seen when a mash is cooled to fermentation temperature (32° C.). This explains that the viscosity needs to be reduced in the process anywhere before the cooling step.

In one embodiment of the present invention the method for degrading grain-based material comprises admixing the xylanase as disclosed herein as early as possible in the biofuel (e.g. bioethanol) production process, e.g. preferably during mixing of the grain-based material at the start of the process. One advantage of adding the xylanases as disclosed herein at an early stage in the process is that the enzymes breakdown initial viscosity.

In one embodiment of the present invention the method for degrading grain-based material comprises admixing the xylanase as disclosed herein prior to or during saccharification, fermentation, or a combination thereof.

In one embodiment of the present invention the method for degrading grain-based material comprises admixing the xylanase as disclosed herein during liquefaction (e.g. a high temperature step that follows mixing).

Therefore in one embodiment the present invention relates to reducing viscosity when degrading grain-based materials, e.g. in biofuel (e.g. bioethanol) production processes.

The benefits of using the xylanases taught herein to reduce viscosity when degrading grain-based materials, e.g. in biofuel (e.g. bioethanol) production processes are multiple:
Higher dry substance mash can be used in the process
Higher solids content of final syrup can be obtained
Better heat transfer, lower energy requirement
Reduced evaporator fouling leading to reduced cleaning costs
Increased final ethanol yields
Improved quality of DDGS (by-product)
Better separation between the solid and liquid part during stillage separation (after distillation). The lower viscosity increases separation efficiency.

A further significant advantage of the present invention is that use of the xylanase described herein in biofuel production can also result in improved (by)products from that process such as wet-cake, Distillers Dried Grains (DDG) or Distillers Dried Grains with Solubles (DDGS). Therefore one advantage of the present invention is since the wet-cake, DDG and DDGS are (by)products of biofuel (e.g. bioethanol) production the use of the present invention can result is improved quality of these (by)products. For example the arabinoxylans in the (by)products can be already dissolved during the biofuel production process.

Cereal (e.g. Wheat) Gluten-Starch Separation

The enzyme (or composition comprising the enzyme) of the present invention or as disclosed herein may be used to breakdown (degrade) AXinsol and AXsol during wheat starch and gluten separation.

After initial separation of the wheat bran and germ from the endosperm, fractionation of wheat endosperm flour into starch and gluten fractions is industrially applied on large scale to obtain high quality A-starch and byproducts B-starch and vital gluten.

The product of the degradation of the cereal flour (e.g. wheat flour) in the present invention is starch (high quality A-starch).

In addition, by-products B-starch and vital gluten are also produced. Each individual product is then further processed to supplement or modify food product characteristics to the market needs.

There are several wheat separation processes used by industry described in literature. These industrial processes differ mainly in the forms of the flour-water mixtures presented to the fractionation equipment (centrifuge, hydrocyclone, or screen) or in the initial reaction conditions as temperature and applying of shear (Abdulvahit Sayaslan, Lebensm.-Wiss. *U-Technol* 37 (2004) 499-515, *Wetmilling of wheat flour: industrial processes and small-scale test methods*).

In the method for separating a cereal flour (e.g. wheat flour) into starch and gluten fractions the method comprises admixing a cereal flour (e.g. wheat flour), water and a xylanase. The cereal flour, water and xylanase may be mixed simultaneously or sequentially. In some embodiments the cereal flour (e.g. wheat flour) and water may be admixed before admixing with the xylanase.

In general, cereal flour (e.g. wheat flour) is either mixed to a dough or batter, varying between 35 to 63% Dry solids, at temperatures of ~20-45° C. The mixture is then further processed either by:
1) letting the mixture rest for some time (~30 minutes) and sequentially washing out the starch from the mixture using a screen, centrifuge or hydrocyclone to separate the starch milk from the gluten, or
2) applying shear to the mixture, optionally diluting the mixture further and then separating the wheat flour by a hydrocyclone, or a 2- or 3-phase decanter centrifuge.

The term "dry solids" as used herein means total solids (dissolved and undissolved) of a slurry (in %) on a dry weight basis.

In one embodiment of the present invention the method or use as claimed may include the steps of mixing wheat flour to form a dough or batter between 35-63% dry solids, at a temperature of about 20 to about 45° C. and separating the starch from the gluten.

The method of the present invention may further comprise:
a) resting the mixture for about 30 minutes and sequentially washing out the starch from the mixture using either a screen, a centrifuge or a hydrocyclone to separate the starch milk from the gluten; or
b) applying shear to the mixture and optionally diluting the mixture further, separating the starch from the gluten using a hydrocyclone or a 2- or 3-phase decanter centrifuge.

The present invention provides for improving the separation of the starch and the gluten by adding xylanases as taught herein suitably during the initial mixing step of flour and water in the various processes described above used for wheat starch separation. Separation is improved by adding xylanases during the initial mixing step due to viscosity reduction and the hydrolysis of AXsol and/or AXinsol interfering with the gluten particles. By degrading these poly- and oligosaccharides, gluten agglomeration is enhanced, improving the gluten yield. (S. A. Frederix, C M. Courtin, J. A. Delcour, J. Cereal Sci. 40 (2004) 41-49. *Substrate selectivity and inhibitor sensitivity affect xylanase functionality in wheat flour gluten-starch separation*).

One advantage of the present invention is that it results in higher A-starch yields and/or better quality gluten (e.g. better quality vital gluten).

One advantage of the present invention is that it improves wheat gluten-starch separation.

One of the ways to evaluate gluten quality is by monitoring gluten agglomeration. When a certain amount of friction through kneading of the dough or mixing of the batter is applied, gluten particles tend to agglomerate into larger particles that form a polymeric network, called "vital gluten". "Vital gluten" can be added to food products to improve properties of baked goods such as dough strength, shelf-life and bread volume (L Day, M. A. Augustin, I. L. Batey and C. W. Wrigley: *Wheat-gluten uses and industry needs; Trends in Food Science & Technology* 17 (2006) 82-90).

In the bakery industry, the quality and quantity of the gluten in a wheat flour is determined by the ICC standard assay No. 155 (AACC 38-12) using a Glutomatic. In this device, a dough is formed from wheat flour (10.0 gr) mixed with a small amount of 2% NaCl solution (4.2-4.8 ml). After 20 seconds of mixing step, the dough is continuously kneaded while being washed for 5 minutes with a 2% NaCl solution at room temperature (~22° C.) pumped through the mixing cup at a flow rate of ~70 ml/minute. During this washing step, the wash water containing starch is collected and the gluten particles form a gluten ball within the Glutomatic sieve holder.

The quality of the gluten is measured by evaluating the gluten agglomeration. This is done by centrifuging the gluten ball in a special centrifuge containing a small sieve. The gluten particles that pass this sieve are weighed (small gluten) and the total amount of gluten is weighed. The gluten index is calculated by (total wet gluten—small wet gluten)/ total wet gluten. The more gluten agglomeration is improved, the smaller the small gluten fraction will be and the higher the gluten index value is. A high gluten index, with a theoretical maximum of 100%, indicates a high quality gluten ball.

Another value to quantify the amount of gluten is the dried gluten yield (%). This value is calculated by dividing the grams of total dried gluten by the total amount of dry flour which was used in the experiment. The more dried gluten is recovered, the better the separation is. This industrial assay is currently under adaptation to simulate a dough separation process used in industry.

Dosages

Preferably, the xylanase is present in the xylan-containing material (e.g. feedstuff) in the range of about 500XU/kg to about 16,000XU/kg xylan-containing material (e.g. feed), more preferably about 750XU/kg feed to about 8000XU/kg xylan-containing material (e.g. feed), preferably about 1500XU/kg feed to about 3000XU/kg xylan-containing material (e.g. feed), preferably about 2000XU/kg feed to about 2500XU/kg xylan-containing material (e.g. feed), and even more preferably about 1000XU/kg xylan-containing material (e.g. feed) to about 4000XU/kg xylan-containing material (e.g. feed).

In one embodiment the xylanase is present in the xylan-containing material (e.g. feedstuff) at more than about 500XU/kg xylan-containing material (e.g. feed), suitably more than about 600XU/kg xylan-containing material (e.g. feed), suitably more than about 700XU/kg xylan-containing material (e.g. feed), suitably more than about 800XU/kg xylan-containing material (e.g. feed), suitably more than about 900XU/kg xylan-containing material (e.g. feed), suitably more than about 1000XU/kg xylan-containing material (e.g. feed), suitably more than about 2000XU/kg, suitably more than about 2500XU/kg, suitably more than about 3000XU/kg xylan-containing material (e.g. feed), In one embodiment the xylanase is present in the xylan-containing material (e.g. feedstuff) at a concentration of between about 2000XU/kg to about 2500XU/kg.

In one embodiment the xylanase is present in the xylan-containing material (e.g. feedstuff) at less than about 16,000XU/kg xylan-containing material (e.g. feed), suitably less than about 8000XU/kg xylan-containing material (e.g. feed), suitably less than about 7000XU/kg xylan-containing material (e.g. feed), suitably less than about 6000XU/kg xylan-containing material (e.g. feed), suitably less than about 5000XU/kg xylan-containing material (e.g. feed), suitably less than about 4000XU/kg xylan-containing material (e.g. feed).

Preferably, the xylanase may be present in a feed additive composition in range of about 100XU/g to about 320,000XU/g composition, more preferably about 300XU/g composition to about 160,000XU/g composition, and even more preferably about 500XU/g composition to about 50,000 XU/g composition, and even more preferably about 500XU/g composition to about 40,000 XU/g composition.

In one embodiment the xylanase is present in the feed additive composition at more than about 100XU/g composition, suitably more than about 200XU/g composition, suitably more than about 300XU/g composition, suitably more than about 400XU/g composition, suitably more than about 500XU/g composition.

In one embodiment the xylanase is present in the feed additive composition at less than about 320,000XU/g composition, suitably less than about 160,000XU/g composition, suitably less than about 50,000XU/g composition, suitably less than about 40,000XU/g composition, suitably less than about 30000XU/g composition.

The xylanase activity can be expressed in xylanase units (XU) measured at pH 5.0 with AZCL-arabinoxylan (azurine-crosslinked wheat arabinoxylan, Xylazyme tablets, Megazyme) as substrate. Hydrolysis by encfo-(1-4)-β-D-xylanase (xylanase) produces water soluble dyed fragments, and the rate of release of these (increase in absorbance at 590 nm) can be related directly to enzyme activity. The xylanase units (XU) are determined relatively to an enzyme standard (Danisco Xylanase, available from Danisco Animal Nutrition) at standard reaction conditions, which are 40° C., 5 min reaction time in McIlvaine buffer, pH 5.0.

The xylanase activity of the standard enzyme is determined as amount of released reducing sugar end groups from an oat-spelt-xylan substrate per min at pH 5.3 and 50° C. The reducing sugar end groups react with 3,5-Dinitrosalicylic acid and formation of the reaction product can be measured as increase in absorbance at 540 nm. The enzyme activity is quantified relative to a xylose standard curve (reducing sugar equivalents). One xylanase unit (XU) is the amount of standard enzyme that releases 0.5 µmol of reducing sugar equivalents per min at pH 5.3 and 50° C.

In one embodiment suitably the enzyme is classified using the E.C. classification above, and the E.C. classification designates an enzyme having that activity when tested in the assay taught herein for determining 1×XU.

Preferably, the xylanase is present in the mixing step of a wheat starch separation process in the dough or batter in the range of about 0.01 kg/MT DS dough or batter to about 0.60 kg/MT DS, more preferably about 0.05 kg/MT DS to about 0.45 kg/MT DS dough or batter, and even more preferably about 0.10 kg/MT DS to about 0.25 kg/MT DS dough or batter.

In some embodiments (particularly in the wheat starch separation embodiment) the xylanase may be dosed in the range of about 0.019 g protein/MT DS wheat flour (which is equivalent to 0.019 mg/kg DS) to about 119 g protein/MT DS wheat flour (which is equivalent to 119 mg/kg DS—where DS means dry solids content and MT means metric ton.

In some embodiments (particularly in the wheat starch separation embodiment) the xylanase may be dosed at about 1.19 g protein/MT DS wheat flour (which is equivalent to about 1.19 mg/kg DS)—where DS means dry solids content and MT means metric ton.

In some embodiments (particularly in the wheat starch separation embodiment) the xylanase may be dosed in the range of about 9 to about 120000 units/kg wheat flour, suitably between about 500-2400 units/kg wheat flour, suitably between about 900-1200 units/kg wheat flour (wherein 1 unit is defined as the amount of enzyme required to generate 1 micromole of xoylose reducing sugar equivalents per minute under the conditions of the birch wood assay of Example 3).

In some embodiments (particularly in degrading grain-based material) the xylanase may be dosed in the range of about 0.29 g/protein/MT DS wheat (which is equivalent to 0.29 mg/kg DS) to about 0290 g/protein/MT DS wheat (which is equivalent to 290 mg/kg DS).

In some embodiments (particularly in degrading grain-based material) the xylanase may be dosed at 2.9 g/protein/MT DS wheat (which is equivalent to 2.9 mg/kg DS).

In some embodiments (particularly in degrading grain-based material) the xylanase may be dosed in the range of about 22 to about 285000 units/kg, suitably about 1100 to about 5700 units/kg, suitably about 2200 to about 2850 units/kg (wherein 1 unit is defined as the amount of enzyme required to generate 1 micromole of xoylose reducing sugar equivalents per minute under the conditions of the birch wood assay of Example 3).

The enzyme and/or composition comprising the enzyme according to the present invention may be designed for one-time dosing or may be designed for use (e.g. feeding) on a daily basis.

The optimum amount of the enzyme and/or composition comprising the enzyme to be used in the present invention will depend on the product to be treated and/or the method of contacting the product with the composition and/or the intended use for the same.

The amount of enzyme used in the compositions should be a sufficient amount to be effective. The amount of enzyme used in the compositions should be a sufficient amount to be effective and to remain sufficiently effective in for example improving the performance of an animal fed feed products containing said composition. This length of time for effectiveness should extend up to at least the time of utilisation of the product (e.g. feed additive composition or feed containing same).

Formulation

In one embodiment the enzyme may be formulated as a liquid, a dry powder or a granule.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

For some embodiments the enzyme may be coated, for example encapsulated.

In one embodiment the coating protects the enzyme from heat and may be considered a thermoprotectant.

In one embodiment the feed additive composition is formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 700 activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

In one embodiment the feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

The granule may be produced using a steam-heated pelleting process which may be conducted between 85° C. and 95° C. for up to several minutes.

In some embodiments the enzyme may be diluted using a diluent, such as starch powder, lime stone or the like.

In one embodiment, the enzyme or composition comprising the enzyme is in a liquid formulation suitable for consumption preferably such liquid consumption contains one or more of the following: a buffer, salt, sorbitol and/or glycerol.

In another embodiment the enzyme or composition comprising the enzyme may be formulated by applying, e.g. spraying, the enzyme(s) onto a carrier substrate, such as ground wheat for example.

In one embodiment the enzyme or composition comprising the enzyme according to the present invention may be formulated as a premix. By way of example only the premix may comprise one or more feed components, such as one or more minerals and/or one or more vitamins.

In one embodiment the enzyme for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Packaging

In one embodiment the enzyme and/or composition comprising same (e.g. feed additive composition) and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

Forms

The enzyme or composition comprising the enzyme (e.g. the feed additive composition) of the present invention and other components and/or the feedstuff comprising same may be used in any suitable form.

The enzyme or composition comprising same (e.g. feed additive composition) of the present invention may be used in the form of solid or liquid preparations or alternatives thereof. Examples of solid preparations include powders, pastes, boluses, capsules, pellets, tablets, pills, capsules, ovules, solutions or suspensions, dusts, and granules which may be wettable, spray-dried or freeze-dried. Examples of liquid preparations include, but are not limited to, aqueous, organic or aqueous-organic solutions, suspensions and emulsions.

The composition comprising the enzyme may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Subject

The term "subject", as used herein, means an animal that is to be or has been administered with a feed additive composition according to the present invention or a feedstuff comprising said feed additive composition according to the present invention.

The term "subject", as used herein, means an animal.

In one embodiment, the subject is a mammal, bird, fish or crustacean including for example livestock or a domesticated animal (e.g. a pet).

In one embodiment the "subject" is livestock.

The term "livestock", as used herein refers to any farmed animal. Preferably, livestock is one or more of ruminants such as cattle (e.g. cows or bulls (including calves)), monogastric animals such as poultry (including broilers, chickens and turkeys), pigs (including piglets), birds, aquatic animals such as fish, agastric fish, gastric fish, freshwater fish such as salmon, cod, trout and carp, e.g. koi carp, marine fish such as sea bass, and crustaceans such as shrimps, mussels and scallops), horses (including race horses), sheep (including lambs).

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain per unit of feed when the animal is fed ad-libitum or a specified amount of feed during a period of time.

By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastrointestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Combination with Other Components

The enzyme of the present invention (or the xylanase as taught herein) may be used in combination with other components.

In one embodiment the enzyme of the present invention (or the xylanase as taught herein) may be used in combination with a probiotic or a direct fed microbial (DFM), e.g. a direct fed bacteria.

The combination of the present invention comprises the enzyme of the present invention (or the xylanase as taught herein or a composition comprising the enzyme, e.g. a feed additive composition) and another component which is suitable for human or animal consumption and is capable of providing a medical or physiological benefit to the consumer.

In one embodiment the "another component" may be one or more further enzymes (e.g. further feed enzymes or brewing or malting enzymes, or grain processing enzymes or wheat gluten-starch separation enzymes).

Suitable additional enzymes for use in the present invention may be one or more of the enzymes selected from the group consisting of: endoglucanases (E.C. 3.2.1.4); cellio-biohydrolases (E.C. 3.2.1.91), β-glucosidases (E.C. 3.2.1.21), cellulases (E.C. 3.2.1.74), lichenases (E.C. 3.1.1.73), lipases (E.C. 3.1.1.3), lipid acyltransferases (generally classified as E.C. 2.3.1.x), phospholipases (E.C. 3.1.1.4, E.C. 3.1.1.32 or E.C. 3.1.1.5), phytases (e.g. 6-phytase (E.C. 3.1.3.26) or a 3-phytase (E.C. 3.1.3.8), alpha-amylases (E.C. 3.2.1.1), other xylanases (E.C. 3.2.1.8, E.C. 3.2.1.32, E.C. 3.2.1.37, E.C. 3.1.1.72, E.C. 3.1.1.73), glucoamylases (E.C. 3.2.1.3), proteases (e.g. subtilisin (E.C. 3.4.21.62) or a bacillolysin (E.C. 3.4.24.28) or an alkaline serine protease (E.C. 3.4.21.x) or a keratinase (E.C. 3.4.X.X)) and/or mannanases (e.g. a β-mannanase (E.C. 3.2.1.78)).

In one embodiment (particularly for feed applications) the other component may be one or more of the enzymes selected from the group consisting of an amylase (including α-amylases (E.C. 3.2.1.1), G4-forming amylases (E.C. 3.2.1.60), β-amylases (E.C. 3.2.1.2) and γ-amylases (E.C. 3.2.1.3); and/or a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)).

In one embodiment (particularly for feed applications) the other component may be a combination of an amylase (e.g. a-amylases (E.C. 3.2.1.1)) and a protease (e.g. subtilisin (E.C. 3.4.21.62)).

In one embodiment (particularly for feed applications) the other component may be a β-glucanase, e.g. an endo-1,3 (4)-β-glucanases (E.C. 3.2.1.6).

In one embodiment (particularly for feed applications) the other component may be a mannanases (e.g. a β-mannanase (E.C. 3.2.1.78)).

In one embodiment (particularly for feed applications) the other component may be a lipase lipase (E.C. 3.1.1.3), a lipid acyltransferase (generally classified as E.C. 2.3.1.x), or a phospholipase (E.C. 3.1.1.4, E.C. 3.1.1.32 or E.C. 3.1.1.5), suitably a lipase (E.C. 3.1.1.3).

In one embodiment (particularly for feed applications) the other component may be a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)).

In one embodiment the additional component may be a stabiliser or an emulsifier or a binder or carrier or an excipient or a diluent or a disintegrant.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others. Examples of granulation binders include one or more of: polyvinylpyrrolidone, hydroxypropylmethylcellulose (HPMC), hydroxypropylcellulose (HPC), sucrose, maltose, gelatin and acacia.

"Carriers" mean materials suitable for administration of the enzyme and include any such material known in the art such as, for example, any liquid, gel, solvent, liquid diluent, solubilizer, or the like, which is non-toxic and which does not interact with any components of the composition in a deleterious manner.

The present invention provides a method for preparing a composition (e.g. a feed additive composition) comprising admixing an enzyme of the present invention with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of "excipients" include one or more of: microcrystalline cellulose and other celluloses, lactose, sodium citrate, calcium carbonate, dibasic calcium phosphate, glycine, starch, milk sugar and high molecular weight polyethylene glycols.

Examples of "disintegrants" include one or more of: starch (preferably corn, potato or tapioca starch), sodium starch glycollate, croscarmellose sodium and certain complex silicates.

Examples of "diluents" include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes) to the xylanase of the present invention.

Preferably, when the feed additive composition of the present invention is admixed with another component(s), the DFM remains viable.

In one embodiment preferably the feed additive composition according to the present invention does not comprise chromium or organic chromium In one embodiment preferably the feed additive according to the present invention does not contain glucanase.

In one embodiment preferably the feed additive according to the present invention does not contain sorbic acid.

Isolated

In one aspect, preferably the amino acid sequence, or nucleic acid, or enzyme according to the present invention is in an isolated form. The term "isolated" means that the sequence or enzyme or nucleic acid is at least substantially free from at least one other component with which the sequence, enzyme or nucleic acid is naturally associated in nature and as found in nature. The sequence, enzyme or nucleic acid of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the sequence, enzyme or nucleic acid according to the present invention is in a purified form. The term "purified" means that the given component is present at a high level. The component is desirably the predominant component present in a composition. Preferably, it is present at a level of at least about 90%, or at least about 95% or at least about 98%, said level being determined on a dry weight/dry weight basis with respect to the total composition under consideration.

Nucleotide Sequence

The scope of the present invention encompasses nucleotide sequences encoding proteins having the specific properties as defined herein.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H ef al., (1980) Nuc Acids Res Symp Ser 215-23 and Horn T et al., (1980) Nuc Acids Res Symp Ser 225-232).

Preparation of the Nucleotide Sequence

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L et al., (1981) Tetrahedron Letters 22, p 1859-1869, or the method described by Matthes et al., (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (Science (1988) 239, pp 487-491).

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme. In the present context, in some embodiments a homologous sequence is taken to include an amino acid or a nucleotide sequence which may be at least 97.7% identical, preferably at least 98 or 99% identical to the subject sequence.

In some embodiments a homologous sequence is taken to include an amino acid or a nucleotide sequence which may be at least 85% identical, preferably at least 90 or 95% identical to the subject sequence.

Typically, the homologues will comprise the same active sites etc. as the subject amino acid sequence for instance. Although homology can also be considered in terms of similarity (i.e. amino acid residues having similar chemical properties/functions), in the context of the present invention it is preferred to express homology in terms of sequence identity.

In one embodiment, a homologous sequence is taken to include an amino acid sequence or nucleotide sequence which has one or several additions, deletions and/or substitutions compared with the subject sequence.

In the present context, "the subject sequence" relates to the nucleotide sequence or polypeptide/amino acid sequence according to the invention.

Preferably, the % sequence identity with regard to a polypeptide sequence is determined using SEQ ID No. 3 as the subject sequence in a sequence alignment. In one embodiment, the polypeptide subject sequence is selected from the group consisting of SEQ ID No. 3, SEQ ID No. 1, SEQ ID No. 2, SEQ ID No. 9, SEQ ID No. 10, SEQ ID No. 11 or SEQ ID No. 15. In a preferred embodiment the polypeptide subject sequence is selected from the mature sequences SEQ ID No. 3, SEQ ID No. 11 or SEQ ID No. 15.

Preferably, the % sequence identity with regard to a nucleotide sequence is determined using SEQ ID No. 6 as the subject sequence in the sequence alignment. In one embodiment, the subject sequence for nucleotide sequences may be selected from the group consisting of SEQ ID No. 4, SEQ ID No. 5. SEQ ID No. 6, SEQ ID No. 12, SEQ ID No. 13, SEQ ID No. 14, SEQ ID No. 16, SEQ ID No. 17 and SEQ ID No. 18. In a preferred embodiment the subject sequence is sequence SEQ ID No. 6.

A "parent nucleic acid" or "parent amino acid" means a nucleic acid sequence or amino acid sequence, encoding or coding for the parent polypeptide, respectively.

In one embodiment the present invention relates to a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids, preferably over at least 100 contiguous amino acids, preferably over at least 200 contiguous amino acids.

In one embodiment the present invention relates to a nucleic acid sequence (or gene) encoding a protein whose amino acid sequence is represented herein or encoding a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In the present context, in one embodiment a homologous sequence or foreign sequence is taken to include a nucleotide sequence which may be at least 97.7% identical, preferably at least 98 or 99% identical to a nucleotide sequence encoding a polypeptide of the present invention (the subject sequence).

In another embodiment, a homologous sequence is taken to include a nucleotide sequence which may be at least 85% identical, preferably at least 90 or 95% identical to a nucleotide sequence encoding a polypeptide of the present invention (the subject sequence).

Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology or % identity between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology or % identity when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology or % identity therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed Chapter 18), BLAST 2 (see FEMS Microbiol Lett 1999 174(2): 247-50; FEMS Microbiol Lett 1999 177(1): 187-8 and (tatiana@ncbi.nlm.nih.gov), PASTA (Altschul et al 1990 J. Mol. Biol. 403-410) and AlignX for example. At least BLAST, BLAST 2 and PASTA are available for offline and online searching (see Ausubel et al 1999. panes 7-58 to 7-60), such as for example in the GenomeQuest search tool (genomequest.com).

Although the final % homology or % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
| --- | --- |
| GAP OPEN | 9 |
| GAP EXTENSION | 2 |

| FOR CLUSTAL | DNA | PROTEIN |
| --- | --- | --- |
| Weight Matrix | IUB | Gonnet 250 |
| GAP OPENING | 15 | 10 |
| GAP EXTEND | 6.66 | 0.1 |

In one embodiment, CLUSTAL may be used with the gap penalty and gap extension set as defined above.

Suitably, the degree of identity with regard to a nucleotide sequence or protein sequence is determined over at least 20 contiguous nucleotides/amino acids, preferably over at least 30 contiguous nucleotides/amino acids, preferably over at least 40 contiguous nucleotides/amino acids, preferably over at least 50 contiguous nucleotides/amino acids, preferably over at least 60 contiguous nucleotides/amino acids, preferably over at least 100 contiguous nucleotides/amino acids.

Suitably, the degree of identity with regard to a nucleotide sequence is determined over at least 100 contiguous nucleotides, preferably over at least 200 contiguous nucleotides, preferably over at least 300 contiguous nucleotides, preferably over at least 400 contiguous nucleotides, preferably over at least 500 contiguous nucleotides, preferably over at least 600 contiguous nucleotides, preferably over at least 700 contiguous nucleotides, preferably over at least 800 contiguous nucleotides.

Suitably, the degree of identity with regard to a nucleotide sequence may be determined over the whole sequence taught herein.

Suitably, the degree of identity with regard to a nucleotide sequence may be determined over the whole sequence taught herein as the mature sequence, e.g. SEQ ID No. 6 or SEQ ID No. 14 or SEQ ID No. 18. Suitably, the degree of identity with regard to a nucleotide sequence may be determined over the whole sequence as taught herein as SEQ ID No. 6.

Suitably, the degree of identity with regard to a protein (amino acid) sequence is determined over at least 100 contiguous amino acids, preferably over at least 200 contiguous amino acids, preferably over at least 300 contiguous amino acids.

Suitably, the degree of identity with regard to an amino acid or protein sequence may be determined over the whole sequence taught herein.

Suitably, the degree of identity with regard to an amino acid or protein sequence may be determined over the whole sequence taught herein as the mature sequence, e.g. SEQ ID No. 3, SEQ ID No. 11 or SEQ ID No. 15. Suitably, the degree of identity with regard to an amino acid or protein sequence may be determined over the whole sequence taught herein as SEQ ID No. 3.

In the present context, the term "query sequence" means a homologous sequence or a foreign sequence, which is aligned with a subject sequence in order to see if it falls within the scope of the present invention. Accordingly, such query sequence can for example be a prior art sequence or a third party sequence.

In one preferred embodiment, the sequences are aligned by a global alignment program and the sequence identity is calculated by identifying the number of exact matches identified by the program divided by the length of the subject sequence.

In one embodiment, the degree of sequence identity between a query sequence and a subject sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the subject sequence.

In yet a further preferred embodiment, the global alignment program is selected from the group consisting of CLUSTAL and BLAST (preferably BLAST) and the sequence identity is calculated by identifying the number of exact matches identified by the program divided by the length of the subject sequence.

The sequences may also have deletions, insertions or substitutions of amino acid residues result in a functionally equivalent substance. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline* L-thioproline*, methyl derivatives of phenylalanine (Phe) such as 4-methyl-Phe*, pentamethyl-Phe*, L-Phe (4-aminof, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or O-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

In one embodiment the xylanase for use in the present invention may comprise a polypeptide sequence shown as SEQ ID No. 1, SEQ ID No. 2 or SEQ ID No. 3. SEQ ID No. 9, SEQ ID No. 10 SEQ ID No. 11 or SEQ ID No. 15 with a conservative substitution of at least one of the amino acids.

Suitably there may be at least 2 conservative substitutions, such as at least 3 or at least 4 or at least 5.

Suitably there may be less than 15 conservative substitutions, such as less than 12, less than 10, or less than 8 or less than 5.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides, may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Amino Acid Numbering

In the present invention, a specific numbering of amino acid residue positions in the xylanases used in the present invention may be employed. By alignment of the amino acid sequence of a sample xylanases with the xylanase of the present invention (particularly SEQ ID No. 3) it is possible to allot a number to an amino acid residue position in said sample xylanase which corresponds with the amino acid residue position or numbering of the amino acid sequence shown in SEQ ID NO:3 of the present invention.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringency conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Preferably hybridisation is analysed over the whole of the sequences taught herein.

Expression of Enzymes

The nucleotide sequence for use in the present invention may be incorporated into a recombinant replicable vector. The vector may be used to replicate and express the nucleotide sequence, in protein/enzyme form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism.

The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes-such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and plJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of a protein having the specific properties as defined herein.

In one embodiment the organism is an expression host.

Thus, a further embodiment of the present invention provides host cells transformed or transfected with a nucleotide sequence that expresses the protein of the present invention. The cells will be chosen to be compatible with the said vector and may for example be prokaryotic (for example bacterial), fungal or yeast cells.

Examples of suitable bacterial host organisms are gram positive or gram negative bacterial species.

In one embodiment the xylanases taught herein are expressed in the expression host *Trichoderma reesei*.

In some embodiments the expression host for the xylanases taught herein may be one or more of the following fungal expression hosts: *Fusarium* spp. (such as *Fusarium oxysporum*); *Aspergillus* spp. (such as *Aspergillus niger, A. oryzae. A. nidulans*, or *A. awamori*) or *Trichoderma* spp. (such as *T. reesei*).

In some embodiments the expression host may be one or more of the following bacterial expression hosts: *Streptomyces* spp. or *Bacillus* spp. (e.g. *Bacillus subtilis* or B. lichenmformis).

The use of suitable host cells—such as yeast and fungal host cells—may provide for post-translational modifications (e.g. myristoylation, glycosylation, truncation, lipidation and tyrosine, serine or threonine phosphorylation) as may be needed to confer optimal biological activity on recombinant expression products of the present invention.

Organism

The term "organism" in relation to the present invention includes any organism that could comprise the nucleotide sequence coding for the polypeptide according to the present invention and/or products obtained therefrom, and/or wherein a promoter can allow expression of the nucleotide sequence according to the present invention when present in the organism.

In one embodiment the organism is an expression host.

Suitable organisms may include a prokaryote, fungus, yeast or a plant.

The term "transgenic organism" in relation to the present invention includes any organism that comprises the nucleotide sequence coding for the polypeptide according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the polypeptide according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the polypeptide of the present invention under the control of a heterologous promoter.

Transformation of Host Cells/Organism

As indicated earlier, the host organism can be a prokaryotic or a eukaryotic organism. Examples of suitable prokaryotic hosts include *E. coli, Streptomyces* spp. and *Bacillus* spp., e.g. *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Transformation of prokaryotes, fungi and yeasts are generally well known to one skilled in the art.

A host organism may be a fungus—such as a mould. Examples of suitable such hosts include any member belonging to the genera *Trichoderma* (e.g. *T. reesei*), *Thermomyces, Acremonium, Fusarium, Aspergillus, Penicillium, Mucor, Neurospora* and the like.

In one embodiment, the host organism may be a fungus. In one preferred embodiment the host organism belongs to the genus *Trichoderma*, e.g. *T. reesei*).

Culturing and Production

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Large Scale Application

In one preferred embodiment of the present invention, the amino acid sequence is used for large scale applications.

Preferably the amino acid sequence is produced in a quantity of from 1 g per litre to about 2 g per litre of the total cell culture volume after cultivation of the host organism.

Preferably the amino acid sequence is produced in a quantity of from 100 mg per litre to about 900 mg per litre of the total cell culture volume after cultivation of the host organism.

Preferably the amino acid sequence is produced in a quantity of from 250 mg per litre to about 500 mg per litre of the total cell culture volume after cultivation of the host organism.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

The invention also relates to the following aspects as defined in the following numbered paragraphs:

1. A method for degrading arabinoxylan-containing material comprising admixing an arabinoxylan-containing material with a xylanase, which xylanase is a GH10, fungal xylanase and degrades insoluble arabinoxylan (AXinsol) as well as degrading the polymers, oligomers or combinations thereof produced from the degradation of the AXinsol. and wherein the xylanase degrades the polymers, oligomers or combinations thereof produced from the degradation of the AXinsol immediately or substantially immediately upon their production.

2. A method for degrading arabinoxylan-containing material in a xylan-containing material, comprising admixing said xylan-containing material with a xylanase comprising a polypeptide sequence shown herein as SEQ ID No. 3, SEQ ID No. 2, SEQ ID No. 1, SEQ ID No. 9, SEQ ID No. 10, SEQ ID No. 11 or SEQ ID No. 15; or a variant, homologue, fragment or derivative thereof having at least 75% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 6, SEQ ID No. 5. SEQ ID No. 4, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity with SEQ ID No. 6, SEQ ID No. 5, SEQ ID No. 4, SEQ ID No. 12, SEQ ID No. 13, SEQ ID No. 14. SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides*.

3. Use of a xylanase comprising a polypeptide sequence shown herein as SEQ ID No. 3, SEQ ID No. 2, SEQ ID No. 1. SEQ ID No. 9, SEQ ID No. 10, SEQ ID No. 11, or SEQ ID No. 15; or a variant, homologue, fragment or derivative thereof having at least 75% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2. SEQ ID No. 1, SEQ ID No. 9. SEQ ID No. 10, SEQ ID No. 11 or SEQ ID No. 15 with a conservative substitution of at least one of the amino acids; or a xylanase which is encoded by a nucleotide sequence shown herein as SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14. SEQ ID No. 16, SEQ ID No. 17 or SEQ ID No. 18 under high stringency conditions, or a nucleotide sequence which has at least 75% identity with SEQ ID No. 6, SEQ ID No. 5, SEQ ID No. 4. SEQ ID No. 12, SEQ ID No. 13, SEQ ID No. 14. SEQ ID No. 16. SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides* for solubilizing arabinoxylan in a xylan-containing material.

4. The method or use according to any one of paragraphs 2 or 3 wherein the arabinoxylan is insoluble arabinoxylan (AXinsol).

5. The method or use according to any one of paragraphs 1-4 wherein the xylan-containing material is selected from one or more of the group consisting of: a feed or feedstuff; a feed component; a grain-based material; a mash; a wort; a malt; malted barely; an adjunct, a barley mash; and a cereal flour.

6. The method or use according to any one of the preceding paragraphs wherein the arabinoxylans are solubilized without increasing viscosity in the reaction medium.

7. The method or use according to any one of the preceding paragraphs wherein the method or use is (or is part of) a wheat gluten-starch separation process.

8. The method or use according to any one of paragraphs 1-6 wherein the method or use is (or is part of) a biofuel (e.g. bioethanol) or biochemical (e.g. bio-based isoprene) production process.

9. The method or use according to any one of paragraphs 1-6 wherein the method or use is (or is part of) a malting or brewing process.

10. The method or use according to any one of paragraphs 1-6 wherein the method or use is for improving the performance of a subject or for improving digestibility of a raw material in a feed (e.g. nutrient digestibility) or for improving feed efficiency in a subject or for reducing the viscosity of the intestinal content of a subject.

11. The method or use according to any one of the preceding paragraphs wherein the xylanase comprises a polypeptide sequence shown herein as SEQ ID No. 3, SEQ ID No. 2, SEQ ID No. 1, SEQ ID No. 9, SEQ ID No. 10, SEQ ID No. 11 or SEQ ID No. 15; or a variant, homologue, fragment or derivative thereof having at least 85% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1. SEQ ID No. 9, SEQ ID No. 10, SEQ ID No. 11, or SEQ ID No. 15 with a conservative substitution of at least one of the amino acids; or a xylanase which is encoded by a nucleotide sequence shown herein as SEQ ID No. 6, SEQ ID No. 5, SEQ ID No. 4, SEQ ID No. 12, SEQ ID No. 13, SEQ ID No. 14, SEQ ID No. 16. SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 85% identity with SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code.

12. The method or use according to any one of the preceding paragraphs wherein the xylanase comprises a polypeptide sequence shown herein as SEQ ID No. 3, SEQ ID No. 2, SEQ ID No. 1, SEQ ID No. 9, SEQ ID No. 10, SEQ ID No. 11 or SEQ ID No. 15; or a variant, homologue, fragment or derivative thereof having at least 95% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 6, SEQ ID No. 5. SEQ ID No. 4, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 95% identity with SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code.

13. The method or use according to any one of the preceding paragraphs wherein the xylanase comprises a polypeptide sequence shown herein as SEQ ID No. 3, SEQ ID No. 2, SEQ ID No. 1, SEQ ID No. 9, SEQ ID No. 10, SEQ ID No. 11 or SEQ ID No. 15; or a variant, homologue, fragment or derivative thereof having at least 99% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 97% (e.g. at least 97.7% or at least 98%) identity with SEQ ID No. 6. SEQ ID No. 5. SEQ ID No. 4, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code.

14. The method or use according to paragraph 5 wherein the feed or feedstuff comprises or consists of corn, DDGS (such as cDDGS), wheat, wheat bran or a combination thereof.

15. The method or use according to paragraph 14 wherein the feed or feedstuff is a corn-based feedstuff.

16. The method or use according to any one of the preceding paragraphs wherein the xylanase is used in combination with one or more of the enzymes selected from the group consisting of a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or an amylase (including ct-amylases (E.C. 3.2.1.1), G4-forming amylases (E.C. 3.2.1.60), β-amylases (E.C. 3.2.1.2) and γ-amylases (E.C. 3.2.1.3); and/or a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)).

17. The method or use according to any one of the preceding paragraphs wherein the xylanase is used in combination with an amylase (e.g α-amylases (E.C. 3.2.1.1)) and a protease (e.g. subtilisin (E.C. 3.4.21.62)).

18. The method or use according to any one of paragraphs 1-15 wherein the enzyme is used in combination with a β-glucanase, e.g. an endo-1,3(4)-β-glucanases (E.C. 3.2.1.6).

19. The method or use according to any one of the preceding paragraphs wherein the xylanase is contacted with a mash and/or a wort.

20. The method or use according to any one of the preceding paragraphs wherein the method comprises the steps of: (a) preparing a mash, (b) filtering the mash to obtain a wort and (c) fermenting the wort to obtain a fermented beverage, wherein said xylanase is added to: (i) the mash of step (a) and/or (ii) the wort of step (b) and/or (iii) the wort of step (c).

21. The method or use according to any one of the preceding paragraphs wherein the xylanase comprises (or consists of) a polypeptide sequence shown herein as SEQ ID No. 3, SEQ ID No. 2 or SEQ ID No. 1, or a variant, homologue, fragment or derivative thereof having at least 99% identity with SEQ ID No. 3 or SEQ ID No. 2 or SEQ ID No. 1; or a polypeptide which is encoded by a nucleotide sequence shown herein as SEQ ID No. 6, SEQ ID No. 5 or SEQ ID No. 4, or a nucleotide sequence which has at least 97% (e.g. at least 97.7% or at least 98%) identity with SEQ ID No. 6, SEQ ID No. 5 or SEQ ID No. 4.

22. A fermented beverage, e.g. beer, produced by a method according to any one of the preceding paragraphs.

23. A polypeptide having xylanase activity comprising (or consisting of) a polypeptide sequence shown herein as SEQ ID No. 3, SEQ ID No. 2 or SEQ ID No. 1, or a variant, homologue, fragment or derivative thereof having at least 99% identity with SEQ ID No. 3 or SEQ ID No. 2 or SEQ ID No. 1; or a polypeptide which is encoded by a nucleotide sequence shown herein as SEQ ID No. 6, SEQ ID No. 5 or SEQ ID No. 4, or a nucleotide sequence which has at least 97% (e.g. at least 97.7% or at least 98%) identity with SEQ ID No. 6, SEQ ID No. 5 or SEQ ID No. 4.

24. The polypeptide according to paragraph 23 wherein the xylanase in an endo-1,4-p-d-xylanase.

25. The polypeptide according to paragraph 23 or paragraph 24 wherein the enzyme has an optimum temperature in the range of 50-70° C., preferably about 60° C.

26. A polypeptide according to any one of paragraphs 23 to 25 wherein the enzyme has a pH optimum in the range of 4.6 to 7, preferably about 6.

27. A polypeptide according to any one of paragraphs 23-26 wherein the enzyme is formulated with a coating or is encapsulated.

28. An isolated or recombinant nucleic acid molecule comprising (or consisting of) a polynucleotide sequence selected from the group consisting of:
  a. a polynucleotide sequence which encodes a polypeptide sequence selected from the group consisting of SEQ ID No. 3. SEQ ID No. 2 or SEQ ID No. 1, or a variant, homologue, fragment or derivative thereof having at least 99% identity with SEQ ID No. 3 or SEQ ID No. 2 or SEQ ID No. 1; or
  b. a polynucleotide sequence shown herein as SEQ ID No. 6, SEQ ID No. 5 or SEQ ID No. 4; or a nucleotide sequence which has at least 97% (e.g. at least 97.7% or at least 98%) identity with SEQ ID No. 6, SEQ ID No. 5 or SEQ ID No. 4.

29. A vector (e.g. a plasmid) comprising a polynucleotide sequence selected from the group consisting of:
  a. a polynucleotide sequence which encodes a polypeptide sequence selected from the group consisting of SEQ ID No. 3, SEQ ID No. 2 or SEQ ID No. 1, or a variant, homologue, fragment or derivative thereof having at least 99% identity with SEQ ID No. 3 or SEQ ID No. 2 or SEQ ID No. 1; or
  b. a polynucleotide sequence shown herein as SEQ ID No. 6, SEQ ID No. 5 or SEQ ID No. 4; or a nucleotide sequence which has at least 97% (e.g. at least 97.7% or at least 98%) identity with SEQ ID No. 6, SEQ ID No. 5 or SEQ ID No. 4.

30. A host cell comprising the nucleic acid of paragraph 28 or a vector of paragraph 29.

31. A method of degrading a xylan-containing material (preferably an insoluble arabinoxylan-containing material) comprising admixing the material with a polypeptide according to any one of paragraphs 23-27.

32. A feed additive composition comprising (or consisting essentially of or consisting of) a xylanase comprising a polypeptide sequence shown herein as SEQ ID No. 3, SEQ ID No. 2, SEQ ID No. 1, SEQ ID No. 9, SEQ ID No. 10, SEQ ID No. 11 or SEQ ID No. 15; or a variant, homologue, fragment or derivative thereof having at least 75% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9. SEQ ID No. 10, SEQ ID No. 11 or SEQ ID No. 15 with a conservative substitution of at least one of the amino acids; or a xylanase which is encoded by a nucleotide sequence shown herein as SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity with SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code, or a xylanase obtainable (or obtained) from *Fusarium verticilloides* or a polypeptide according to any one of paragraphs 23 to 27.

33. The feed additive composition according to paragraph 32 which further comprises one or more of the enzymes selected from the group, consisting of an amylase (including α-amylases (E.C. 3.2.1.1), G4-forming amylases (E.C. 3.2.1.60), β-amylases (E.C. 3.2.1.2) and 7-amylases (E.C. 3.2.1.3); and/or a protease (e.g. subtilisin (E.C. 3.4.21.62) or a bacillolysin (E.C. 3.4.24.28) or an alkaline serine protease (E.C. 3.4.21.x)) or a keratinase (E.C. 3.4.x.x)).

34. The feed additive composition according to paragraph 32 or paragraph 33 which further comprises an amylase (e.g α-amylases (E.C. 3.2.1.1)) and a protease (e.g. subtilisin (E.C. 3.4.21.62)).

35. The feed additive composition according to paragraph 32 which further comprises a D-glucanase, e.g. an endo-1,3(4)-β-glucanases (E.C. 3.2.1.6).

36. A premix comprising a xylanase comprising a polypeptide sequence shown herein as SEQ ID No. 3, SEQ ID No. 2, SEQ ID No. 1, SEQ ID No. 9, SEQ ID No. 10, SEQ ID No. 11 or SEQ ID No. 15; or a variant, homologue, fragment or derivative thereof having at least 75% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18 under high stringency conditions, or a nucleotide sequence which has at least 75% identity with SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code; a polypeptide according to any one of paragraphs 23 to 27; or a feed additive composition comprising according to any one of paragraphs 32 to 35; or a xylanase obtainable (or obtained) from *Fusarium verticilloides*, and at least one mineral and/or at least one vitamin.

37. The method or use according to any one of paragraphs 1-21 comprising administering a subject with a polypeptide according to any one of paragraphs 23-27 or a feed additive composition according to any one of paragraphs 32 to 35 or a premix according to paragraph 36 or a xylanase obtainable (or obtained) from *Fusarium verticilloides*.

38. A kit comprising a polypeptide according to any one of paragraphs 23-27 or a feed additive composition according to any one of paragraphs 32-35 or a premix according to paragraph 36 and instructions for administration.

39. A feedstuff comprising a feed additive composition according to any one of paragraphs 32-35 or a feed additive composition comprising (or consisting essentially of or consisting of) a xylanase comprising a polypeptide sequence shown herein as SEQ ID No. 3, SEQ ID No. 2, SEQ ID No. 1. SEQ ID No. 9, SEQ ID No. 10, SEQ ID No. 11 or SEQ ID No. 15; or a variant, homologue, fragment or derivative thereof having at least 75% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16. SEQ ID No. 17 or SEQ ID No. 18 under high stringency conditions, or a nucleotide sequence which has at least 75% identity with SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code; a polypeptide according to paragraphs 23-27, or a xylanase obtainable (or obtained) from *Fusarium verticilloides* or a feed additive composition according to any one of paragraphs 32-35.

40. A method of preparing a feedstuff comprising admixing a feed component with a xylanase comprising a polypeptide sequence shown herein as SEQ ID No. 3, SEQ ID No. 2. SEQ ID No. 1, SEQ ID No. 9, SEQ ID No. 10, SEQ ID No. 11 or SEQ ID No. 15; or a variant, homologue, fragment or derivative thereof having at least 75% identity with SEQ ID No. 3 or SEQ ID No. 2 or SEQ ID No. 1 or SEQ ID No. 9 or SEQ ID No. 10 or SEQ ID No. 11 or SEQ ID No. 15; or a polypeptide sequence which comprises SEQ ID No. 3, SEQ ID No. 2, SEQ ID No. 1, SEQ ID No. 9, SEQ ID No. 10, SEQ ID No. 11 or SEQ ID No. 15 with a conservative substitution of at least one of the amino acids; or a xylanase which is encoded by a nucleotide sequence shown herein as SEQ ID No. 6. SEQ ID No. 5, SEQ ID No. 4, SEQ ID No. 12, SEQ ID No. 13. SEQ ID No. 14, SEQ ID No. 16, SEQ ID No. 17 or SEQ ID No. 18, or a nucleotide sequence which can hybridize to SEQ ID No. 6, SEQ ID No. 5, SEQ ID No. 4, SEQ ID No. 12, SEQ ID No. 13, SEQ ID No. 14, SEQ ID No. 16. SEQ ID No. 17 or SEQ ID No. 18 under high stringency conditions, or a nucleotide sequence which has at least 75% identity with SEQ ID No. 6, SEQ ID No. 5, SEQ ID No. 4, SEQ ID No. 12, SEQ ID No. 13, SEQ ID No. 14, SEQ ID No. 16, SEQ ID No. 17 or SEQ ID No. 18, or a nucleotide sequence which differs from SEQ ID No. 6 or SEQ ID No. 5 or SEQ ID No. 4 or SEQ ID No. 12 or SEQ ID No. 13 or SEQ ID No. 14 or SEQ ID No. 16 or SEQ ID No. 17 or SEQ ID No. 18 due to the degeneracy of the genetic code; a polypeptide according to paragraphs 23-27, or a xylanase obtainable (or obtained) from *Fusarium verticilloides* or a feed additive composition according to any one of paragraphs 32-35.

41. A polypeptide, nucleic acid, vector, host cells, methods, uses and kits as generally described herein with reference to the Figures and Examples.

The invention will now be described, by way of example only, with reference to the following Figures and Examples.

EXAMPLES

Example 1

Cloning of *Fusarium verticillioides* Xylanase (FveXyn4)

Figure 10:
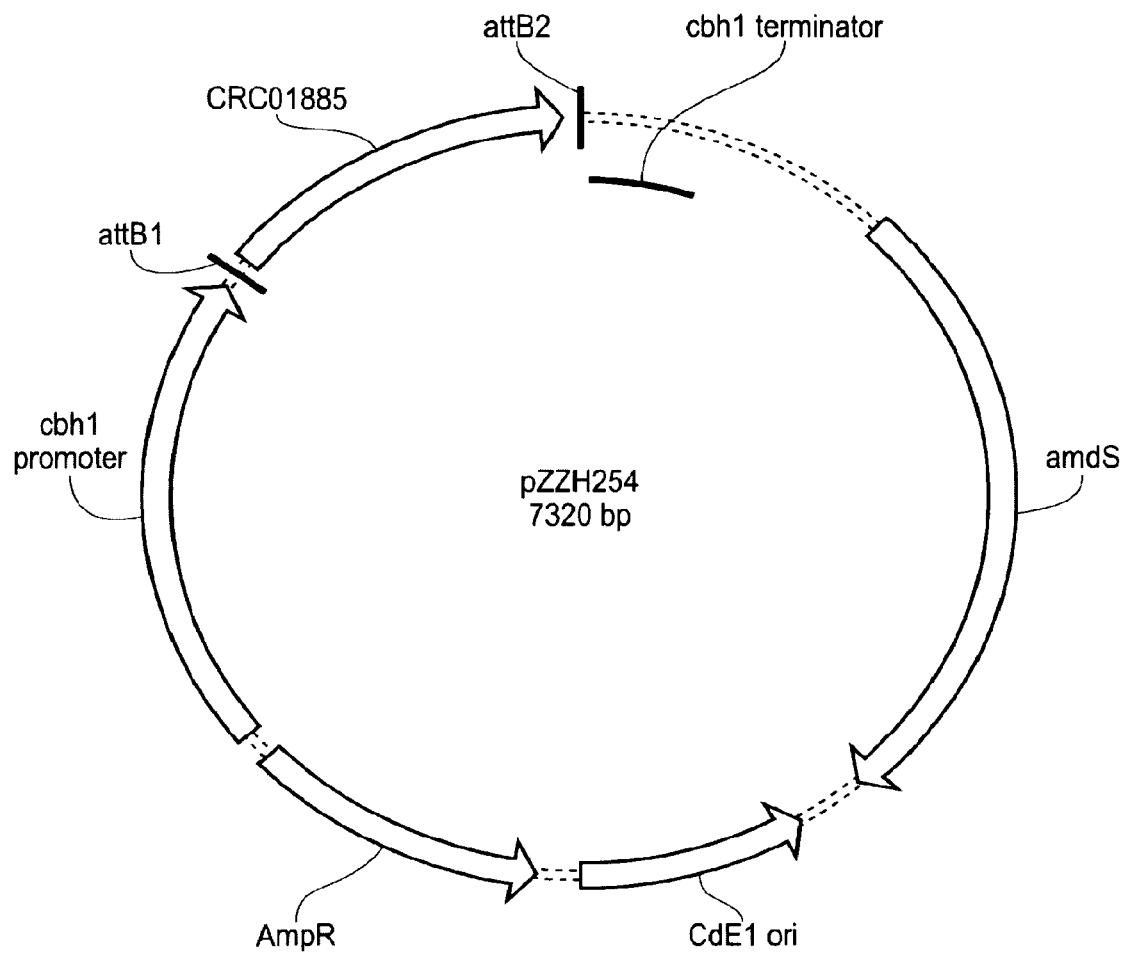
FIG. 10 shows a plasmid map of pZZH254.

Genomic DNA isolated from a strain of *Fusarium verticillioides* was used for amplifying a xylanase gene. The sequence of the cloned gene, called the FveXvn4 gene, is depicted in SEQ ID No. 4. The protein encoded by the FveXyn4 gene is depicted in SEQ ID No. 1. The protein product of gene FveXyn4 belongs to glycosyl hydrolase family 10 (OHIO) based on the PFAM search (pfam.sanger-.ac.uk). At the N-terminus, FveXyn4 protein has a 15 amino acid signal peptide predicted by SignalP-NN (Emanuelsson et al., Nature Protocols, 2:953-971, 2007). This indicates that FveXvn4 is a secreted glycosyl hydrolase.

Example 2

Expression of FveXyn4 Protein

The FveXyn4 gene was amplified from genomic DNA of *Fusarium verticillioides* using the following primers: Primer 1 5'-caccATGAAGCTGTCTTCTTCCTCTA-3' (SEQ ID No. 7), and Primer 2 5'-TITTAGCG-GAGAGCGTTGACAACAGC-3' (SEQ ID No. 8). The PCR product was cloned into pENTR/D-TOPO vector (Invitrogen K2400) to generate the FveXyn4 pEntry plasmid. The expression plasmid pZZH254 was obtained by Gateway cloning reaction between the FveXyn4 pEntry plasmid and pTrex3gM expression vector (described in US 2011/0136197 A1) using Gateway® LR Clonase® TI enzyme kit (Invitrogen 11791). A map of plasmid pZZH254 is provided as FIG. 10. The sequence of the FveXyn4 gene was confirmed by DNA sequencing (SEQ ID No. 4). The plasmid pZZH254 was transformed into a quad deleted *Trichoderma reesei* strain (described in WO 05/001036) using biolistic method (Te'o V S et al., J Microbiol Methods, 51:393-9, 2002).

Following sequence confirmation, protoplasts of a quad deleted *T. reesei* strain (described in WO 05/001036) were transformed with the expression plasmid pTTF-Ate CA1 using the PEG protoplast method (Penttila et al, Gene, 61:155-164, 1987). For protoplast preparation, spores were grown for about 10 hours at 24° C. in *Trichoderma* Minimal Medium MM (20 g/L glucose, 15 g/L $KH_2PO_4$, pH 4.5, 5 g/L $(NH_4)_2SO_4$, 0.6 g/L $MgSO_4 x 7H_2O$, 0.6 g/L $CaCl_2 x 2H_2O$, 1 ml of 1000× *T. reesei* Trace elements solution (175 g/L Citric Acid anhydrous, 200 g/L $FeSO_4 x 7H_2O$, 16 g/L $ZnSO_4 x 7H_2O$, 3.2 g/L $CuSO_4$, 1.4 g/L $MnSO_4 x H_2O$, and 0.8 g/L Boric Acid). Germinating spores were harvested by centrifugation and treated with 30 mg/mL Vinoflow FCE (Novozymes, AG Switzerland) solution for from 7 hours to overnight at 30° C. at 100 rpm to lyse the fungal cell walls. Protoplasts were washed in 0.1 M Tris HCl buffer (pH 7) containing 0.6 M sorbitol and resuspended in 10 mM Tris HCl buffer (pH 7.5) containing 1.2 M sorbitol and 10 mM calcium chloride. For PEG transformation, approximately 1 μg of DNA and $1-5 \times 10^7$ protoplasts in a total volume of 200 μl were treated with 2 ml of 25% PEG solution, diluted with 2 volumes of 1.2 M sorbitol/10 mM Tris, pH 7.5/10 mM $CaCl_2$ solution. Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (UI) sulfate 5 mg/L: zinc sulfate 1.4 mg/L; cobalt (H) chloride 1 mg/L; manganese (II) sulfate 1.6 mg/L; agar 20 g/L; pH 4.25). Transformed colonies (about 50-100) appeared in about 1 week. After growth on acetamide plates, the spores were collected and reselected on acetamide plates. After 5 days, the spores were collected using 10% glycerol, and $1 \times 10^8$ spores were inoculated in a 250 ml shake flask with 30 ml Glucose/Sophorose defined medium for protein expression. Protein expression was confirmed by SDS-PAGE. The spore suspension was subsequently grown in a 7 L fermentor in a defined medium containing 60% glucose-sophorose feed. Glucose/Sophorose defined medium (per liter) consists of $(NH_4)_2SO_4$ 5 g. PIPPS buffer 33 g, Casamino Acids 9 g, $KH_2PO_4$ 4.5 g, $CaCl_2$ (anhydrous) 1 g, $MgSO_4.7H_2O$ 1 g, pH to 5.5 adjusted with 50% NaOH with Milli-Q $H_2O$ to bring to 966.5 mL After sterilization, the following were added: 26 mL 60% Glucose/Sophrose, and 400× *T. reesei* Trace Metals 2.5 mL.

FveXyn4 was purified from concentrated fermentation broth of a 7 L fermentor culture using two chromatography columns. Concentrated fermentation broth buffered in 20 mM sodium phosphate buffer pH 6.0 containing 1 M ammonium sulfate was loaded on a hydrophobic interaction chromatography column (Sepharose Phenyl FF, 26/10). The protein was eluted from the column using a linear gradient of equilibration/wash buffer to 20 mM sodium phosphate buffer pH 6.0. The fraction containing FveXyn4 protein was loaded onto a gel filtration column (HiLoad Superdex 75 μg 26/60), and the mobile phase used was 20 mM sodium phosphate, pH 7.0, containing 0.15 M NaCl. The purified protein was concentrated using a 3K Amicon Ultra-15 device and the concentrated protein fraction was used in further studies.

The nucleotide sequence of FveXyn4 gene from expression plasmid pZZH254 is set forth as SEQ ID No. 4. The signal sequence is shown in bold (upper case), and the predicted intron is shown in bold and lowercase.

The amino acid sequence of FveXyn4 protein expressed from plasmid pZZH254 is set forth as SEQ ID No. 1. The signal sequence predicted by SignalP-NN software is shown underlined. This is the pre-pro-protein.

The amino acid sequence of the predicted mature form of FveXyn4 protein is set forth as SEQ ID No. 3. This is the active form of the enzyme. SEQ ID No. 2 shows the pro-protein, i.e. before post-translational modification. Depending on the host the post-translation modification may vary and therefore the present invention also encompasses mature, active forms of SEQ ID No. 2.

Example 3

Xylanase Activity of FveXyn4

FveXyn4 belongs to the glycosyl hydrolase 10 family (GH10, CAZy number). The beta 1-4 xylanase activity of FveXyn4 was measured using 1% xylan from birch wood (Sigma 95588) or 1% arabinoxylan from wheat flour (Megazyme P-WAXYM) as substrates. The assay was performed in 50 mM sodium citrate pH 5.3, 0.005% Tween-80 buffer at 50° C. for 10 minutes.

The released reducing sugar was quantified by reaction with 3,5-Dinitrosalicylic acid and measurement of absorbance at 540 nm. The enzyme activity is quantified relative to a xylose standard curve. In this assay, one xylanase unit (U) is defined as the amount of enzyme required to generate 1 micromole of xylose reducing sugar equivalents per minute under the conditions of the assay.

Example 4 pH Profile of FveXyn4

Figure 11:
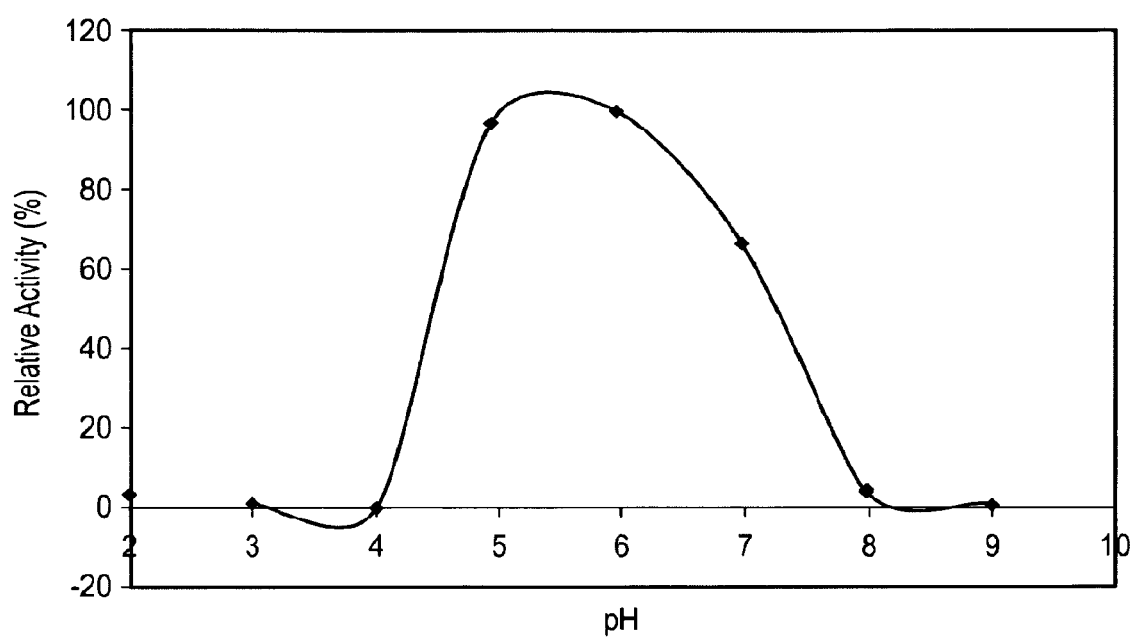
FIG. 11 shows the pH activity profile of FveXyn4.

The pH profile of FveXyn4 was determined using xylan from birch wood (Sigma 95588) as substrate. The assay was performed in Sodium Citrate/Sodium Phosphate buffer solution adjusted to pH values between 2 and 9. Birchwood xylan (2% solution) dissolved in water was mixed with same volume of 50 mM Citrate/Phosphate buffer solution in a 96-well plate, and the substrate was equilibrated at 50° C. before adding enzyme. After 10 minutes, the enzyme reaction was stopped by transferring 60 microliters of reaction mixture to a 96-well PCR plate containing 100 microliters of DNS solution. The PCR plate was heated at 95° C. for 5 minutes in a Bio-Rad DNA Engine. Then plate was cooled to room temperature and 100 microliters were transferred from each well to a new 96-well plate. Release of reducing sugars from the substrate was quantified by measuring the optical density at 540 nm in a spectrophotometer. Enzyme activity at each pH was reported as relative activity where the activity at the pH optimum was set to 100%. The pH profile of FveXyn4 is shown in FIG. 11. FveXyn4 was found to have an optimum pH at about 6, and was found to retain greater than 70% of maximum activity between pH 4.6 and 7.

Example 5

Temperature Profile of FveXyn4

Figure 12:
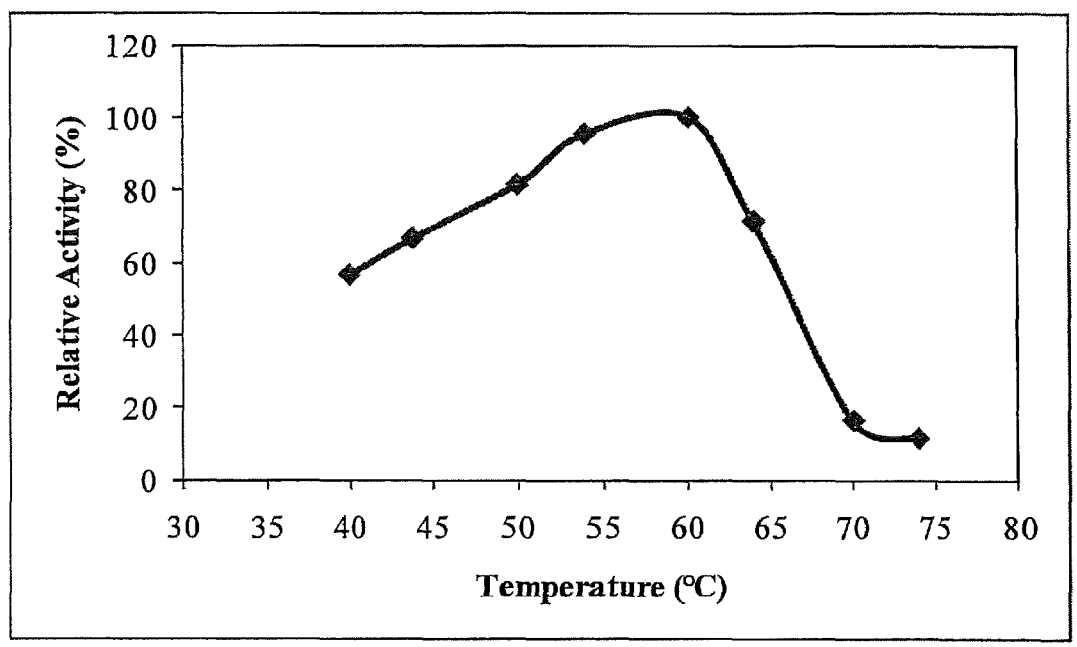
FIG. 12 shows the temperature profile of FveXyn4.

The temperature optimum of purified FveXyn4 was determined by assaying for xylanase activity at temperatures varying between 40° C. and 75° C. for 10 minutes in 50 mM sodium citrate buffer at pH 5.3. The activity was reported as relative activity where the activity at the temperature optimum was set to 100%. The temperature profile of FveXyn4 is shown in FIG. 12. FveXyn4 was found to have an optimum temperature of 60° C., and was found to retain greater than 70% of maximum activity between 45° C. and 64° C.

Example 6

Pentosan Solubilisation (Breakdown or Solubilisation of Insoluble Arabinoxylan (AXinsol))

The new xylanase (FveXyn4) was cloned, expressed, purified and characterized and tested against a benchmark xylanase product (Econase® XT).

The ability to solubilize insoluble arabinoxylan from 4 substrates, namely wheat, wheat bran, corn and corn DDGS was used as the key selection criteria.

The new xylanase showed strong performance on pentosan solubilisation from relevant feed raw materials (wheat, wheat bran, corn, corn DDGS). Surprisingly the new xylanase was far better than the benchmarks (e.g. the commercially available xylanase products) on a greater number of substrates.

In particular the enzyme was surprisingly far superior to the benchmark on the corn based materials.

The new xylanase also shows numerous advantageous properties for its industrial use including unexpectedly high pentosan solubilisation, particularly in feedstuffs comprising corn.

6.1 Materials and Methods

Enzyme Samples

The xylanases used in this study are:

A new GH10 xylanase from *Fusarium verticilloides* (designated FveXyn4) expressed in *Trichoderma reesei*, wherein the xylanase was used in purified form—this enzyme may be referred to herein as FveXyn4, and the following benchmark, commercially available xylanase: Econase® XT. This benchmark enzyme was extracted from commercial dry formulated samples. The xylanase component from Econase® XT commercial dry formulated samples was extracted in a 33% (w/w) slurry using McIlvain buffer, pH 5.0. The extract was cleared using centrifugation (3000 RCF for 10 min) and filtered using a PALL Acrodisc PF syringe filter (0.8/0.2 µm Supor membrane) and subsequently heated 20 min at 70° C. After removable of precipitation by centrifugation (38 724 RCF for 15 min) the buffer was replaced by passage through a Sephadex G25 column (PD10 from Pharmacia) equilibrated with 20 mM Na Citrate, 20 mM NaCl, pH 3.4. Purification of the xylanase component was performed using Source 15S resin, followed by elution with a linear increasing salt gradient (NaCl in 20 mM Na Citrate buffer pH 3.4).

Econase XT® is an endo-1,4-β-xylanase (EC 3.2.1.8) produced by the strain *Trichoderma reesei* RF5427 (CBS 114044), available from ABVista.

Protein concentration was determined by measuring absorption at 280 nm. The extinction coefficients were estimates from the amino acid sequences. For Econase XT the absorption at 280 nm of 1 mg/ml was calculated to be 2.84 AU.

Feed Raw Materials

The feed used in these experiments is raw material. The feeds are either corn, corn DDGS, wheat or wheat bran.

Pentosan Solubilisation (AXinsol Solubilisation)

The method used for pentosan solubilisation was: 100 mg of feed raw material was transferred to a 2 ml Eppendorf centrifuge tube and the precise weight recorded. 750 µL incubation buffer (200 mM HEPES, 100 mM NaCl, 2 mM CaCl, pH 6.0) and 900 µl chloramphenicol solution (40 µg/ml in incubation buffer) was added. Enzyme of choice was added to make a total volume of 1.8 mL.

Each sample was assayed in doublets and in parallel with a blank (incubation without exogenously added enzyme). The samples were incubated on an Eppendorf thermomixer at 40° C. with shaking. After 2 or 18 hours of incubation the supernatant was filtered using 96 wells filterplates (Pall Corporation, AcroPrep 96 Filter Plate, 1.0 µm Glass, NTRL, 1 mL well). After filtration the samples were stored at 4° C. until analysis for total amount of C5 sugars, arabinose and xylose.

Quantification of C5 Sugars (Pentosans)

The total amount of pentoses brought into solution was measured using the method of Rouau and Surget (1994, A rapid semi-automated method of the determination of total and water-extractable pentosan in wheat flours. Carbohydrate Polymers, 24, 123-32) with a continuous flow injection apparatus (FIG. 7). The supernatants were treated with acid to hydrolyse polysaccharides to monosugars. Phloroglucinol (1,3,5-trihydroxybenzen) was added for reaction with monopentoses and monohexoses, which forms a coloured complex. By measuring the difference in absorbance at 550 nm compared to 510 nm, the amount of pentoses in the solution was calculated using a standard curve. Unlike the pentose-phloroglucinol complex, the absorbance of the hexose-phloroglucinol complex is constant at these wavelengths. Glucose was added to the phloroglucinol solution to create a constant glucose signal and further ensure no interference from hexose sugars.

6.2 Results and Discussion

Pentosan solubilisation was monitored in a dose response setup using fibrous by-products of wheat (namely wheat bran) and a fibrous by-product of corn (namely cDDGS).

Figure 8:
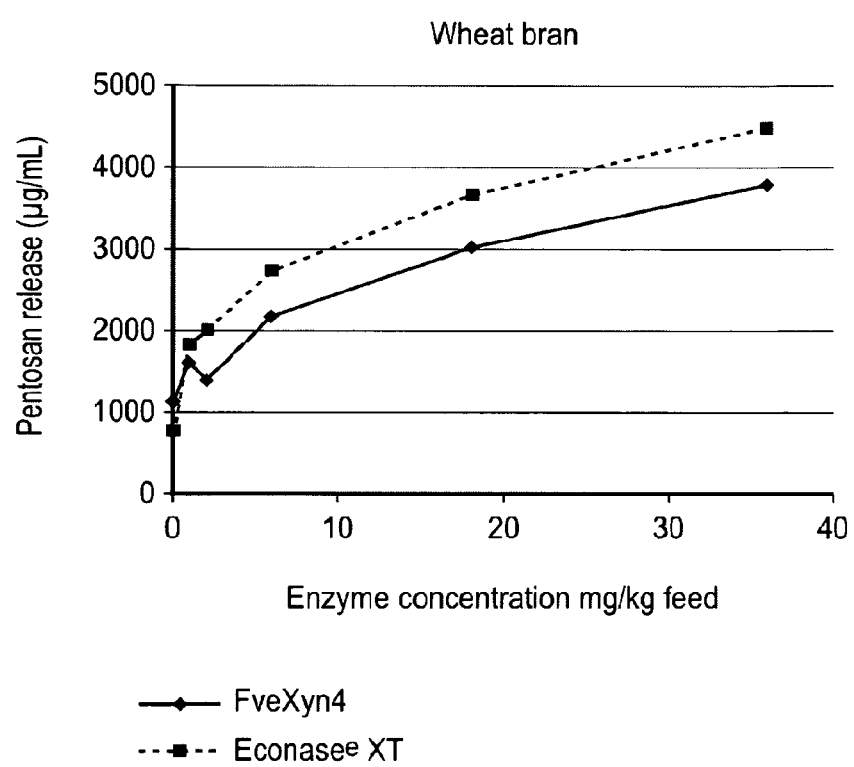
FIG. 8 shows pentosan (C-5 sugar) release (solubilisation of pentosans) from wheat bran as a function of xylanase dosage. The xylanases used were the xylanase of the present invention (FveXyn4) compared with a benchmark xylanase namely Econase® XT.
Figure 9:
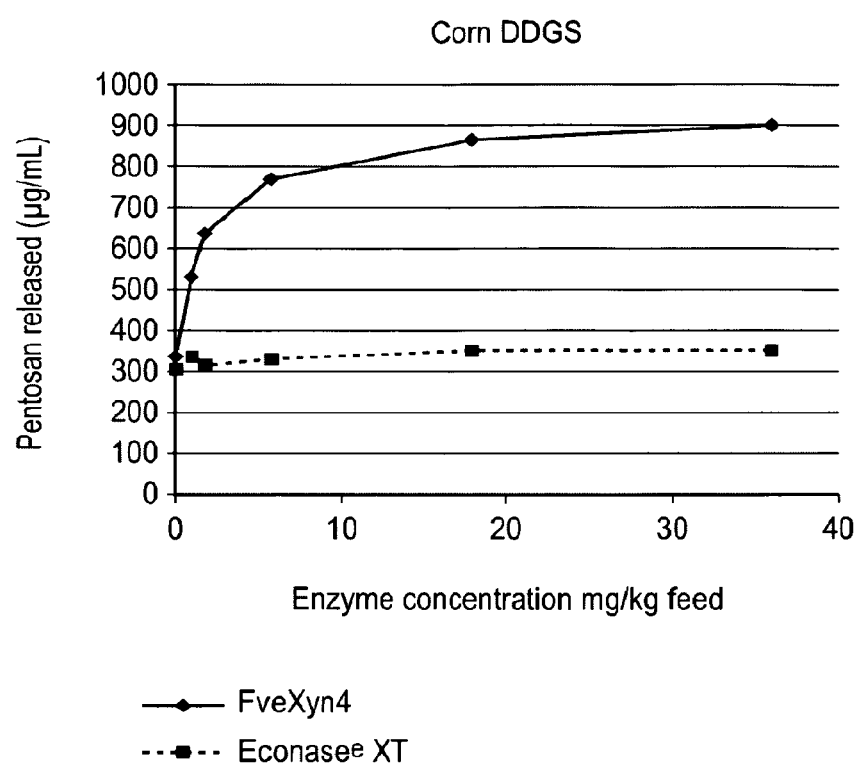
FIG. 9 shows solubilisation of pentosans from cDDGS as a function of xylanase dosage. The xylanases used were the xylanase of the present invention (FveXyn4) compared with a benchmark xylanase namely Econase® XT.

The results from benchmark Econase® XT and of the novel xylanase (FveXyn4) are shown in FIG. 8 (in wheat bran) and FIG. 9 (in corn DDGS).

FIG. 8 shows pentosan (C-5 sugar) release (solubilisation of pentosans) from wheat bran as a function of xylanase dosage. The xylanases used were the xylanase of the present invention (FveXyn4) compared with the benchmark xylanase namely Econase® XT.

FIG. 9 shows solubilisation of pentosans from cDDGS as a function of xylanase dosage. The xylanases used were the xylanase of the present invention (FveXyn4) compared with the benchmark xylanase namely Econase® XT.

Econase® XT performs well on wheat but shows no or limited effect on corn.

This indicates a clear difference in substrate specificity compared to for instance FveXyn4, surprisingly FveXyn4 is good at breaking down AXinsol (e.g. solubilising pentosans) in both wheat and corn based substrates. Typically xylanase enzymes are poor performers on corn based products. Surprisingly the present enzyme is capable of dissolving insoluble arabinoxylans (AXinsol) in both wheat and corn based substrates.

It is worth noting that the tested commercially available xylanase (Econase® XT) did not show significant solubilisation of corn. In fact, there are very few commercially available xylanases that show significant ability to dissolve AXinsol in corn (or solubilisation of corn). This is where the present enzyme differs significantly.

Example 7

Viscosity Reduction in In Vitro Animal Model Assay

Viscosity reduction on wheat was determined using a modified version of the procedure described by Bedford & Classen (1993 Poultry Sci., 72, 137-143). 3.6 ml. of pepsin solution (2000 U/mL in 0.1 N HCl) was mixed with 2.4 g wheat prior to addition of the indicated amount of xylanase (FveXyn4) followed by 45 min incubation at 40° C. 1.2 ml pancreatin solution (8 mg/mL in 1 M MES, pH 6.8) was then mixed into the slurry resulting in a final pH at 6.0. The sample was allowed to incubate for 60 min at 40° C. with mixing after 30 and 60 min. The sample was then placed on ice for 5 min to stop the reaction and centrifuged 10 min at 3320 RCF followed by filtration through a 0.45 μm filter to obtain a clear supernatant. Sample viscosity was then measured at 20° C. using a Brookfield digital viscometer (model DV-I+, Brookfield Engineering Laboratories, Stoughton, MA 02172, USA) fitted with a CPE-40 cone and plate. Each data point is the average of three repetitions.

Figure 13:
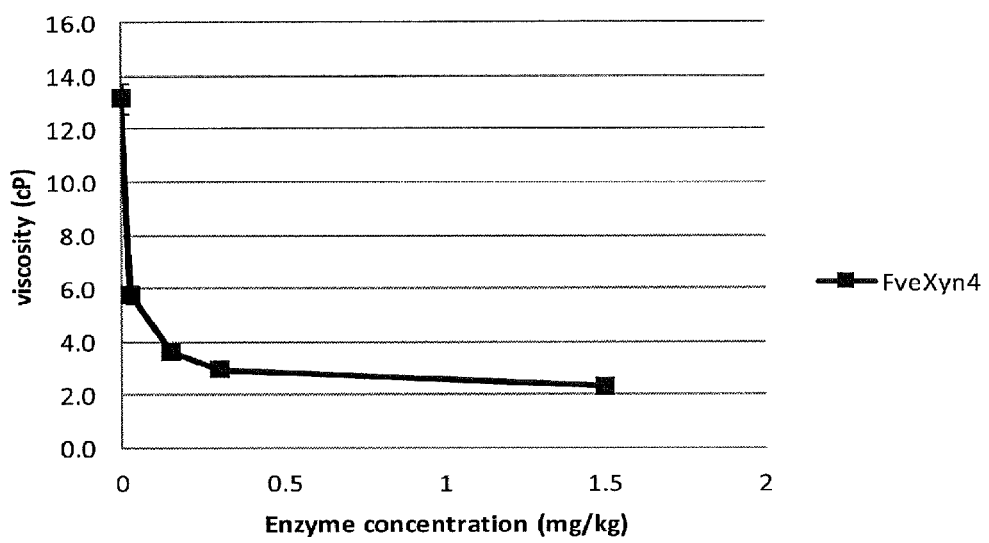
FIG. 13 shows viscosity reduction on high viscosity wheat by FveXyn4 in an in vitro animal model (where pH was maintained at 6.0).

The results are shown in FIG. 13. As can be seen even under these conditions (which conditions attempt to mimic the environment in the small intestine of an animal) FveXyn4 reduces the viscosity.

Example 8

Viscosity Reduction in Grain-Based Material (e.g. for Biofuel Production)

In the European fuel alcohol industry, small grains like wheat, barley and rye are common raw materials, in contrast to the US where mainly corn is used. These small grains contain, next to starch, high levels of non-starch polysaccharide polymers (NSP), like cellulose, beta-glucan and hemicellulose.

The ratio in which the different NSPs are represented differ for each feedstock.

NSPs give high viscosity to grain mashes due to their large water-binding capacity. High viscosity has a negative impact on ethanol production since it will limit the solid concentration that can be used in mashing and it will reduce the energy efficiency of the process. In addition, residual hemicelluloses present throughout the process may contribute to fouling in heat exchangers and distillation equipment. The largest impact of a high viscosity is seen when a mash is cooled to fermentation temperature (32° C.). This explains that the viscosity needs to be reduced in the process anywhere before the cooling step.

8.1 Materials and Methods

A Rapid Visco Analyzer (RVA 4500) from Perten Instruments was used to measure viscosity profiles of a wheat mash. The RVA 4500 is a cooking stirring viscometer with ramped temperature and variable shear that can be used to determine the quality and processing characteristics of starch in grains, tubers, flours and extruded and cooked foods and feeds. There are also applications for protein foods, ingredients such as modified starches and hydrocolloids and malting and brewing.

The wheat mash (50 grams of a 30% DS, 34.86% 'as is' slurry) was prepared according to the following protocol:
  Weigh 17.42 grams of wheat
  In a 50 ml beaker glass, weigh 32.58 grams of tap water and add 114 μl 4N $H_2SO_4$
  Add the wheat to the water and stir for 5 minutes at maximum speed (approx. 500 rpm) with an overhead stirrer
  Transfer 25.0 grams of this slurry (pH 5.2) to an RVA cup, add 50-fold diluted enzymes and start RVA run
  Divide all slurry over two 15-ml Greiner centrifuge tubes and centrifuge 10 minutes at 3500 rpm (2547×g)
  Determine layer separation (read volume scale on centrifuge tube)

The term "dry solids content (DS)" refers to the total solids (dissolved and undissolved) of a slurry (in %) on a dry weight basis. At the onset, "initial DS" refers to the dry solids in the slurry at time zero. As the hydrolysis reaction proceeds, the portion of DS that are dissolved can be referred to as "Syrup DS" as well as "Supernatant DS".

In each experiment (25 grams of slurry), xylanases FveXyn4 and FoxXyn2 were dosed at 25 μg protein (per 8.71 g wheat 'as is'), corresponding to 2.9 μg protein per g wheat 'as is'. XYLATHIN™ was dosed at 4 μg protein per g wheat 'as is'. SPEZYME® CL was dosed at 2.0 AAU/g DS (2.3 AAU/g 'as is').

Figure 14:
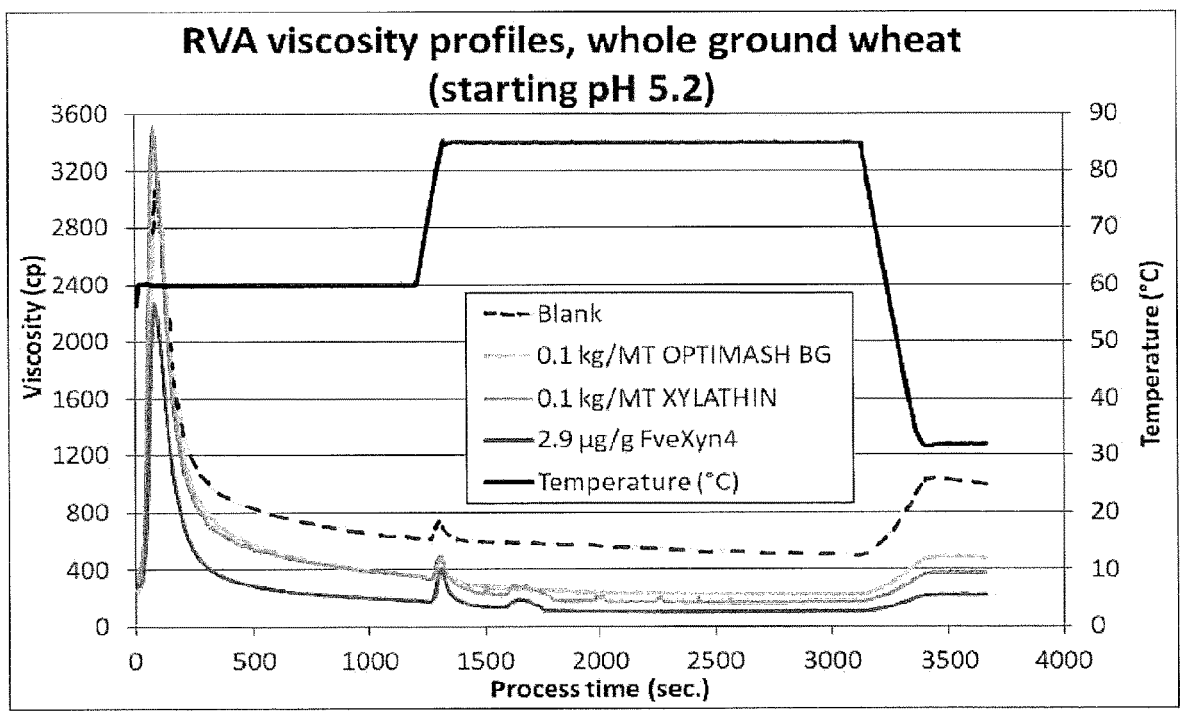
FIG. 14 shows RVA viscosity profiles in whole ground wheat starting at pH5.2 for the xylanase in accordance with the present invention namely FveXyn4 and the benchmark enzymes Xylathin™.
Figure 18:
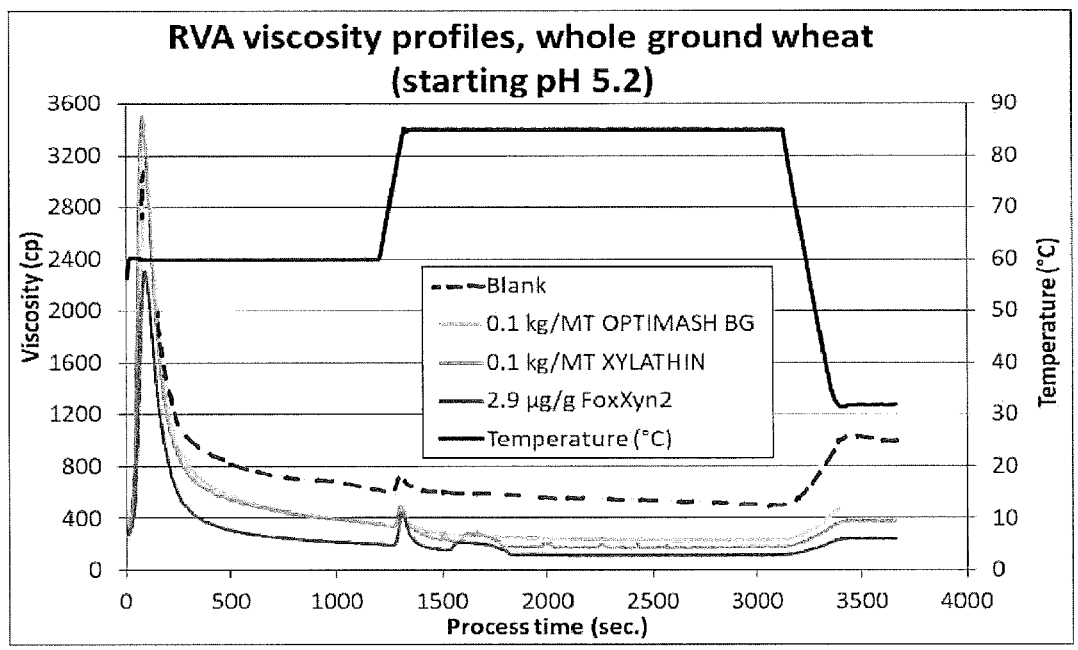
FIG. 18 shows RVA viscosity profiles in whole ground wheat starting at pH5.2 for the xylanase in accordance with the present invention namely FoxXyn2 and the benchmark enzymes Xylathin™.

A standard wheat liquefaction was mimicked in the RVA. Pretreatment was performed for 20 minutes at 60° C., followed by a liquefaction step for 30 minutes at 85° C. After pretreatment and liquefaction, slurry was cooled down to 32° C., to determine viscosity at fermentation conditions. Tables below contain the viscosities after each step, complete RVA profiles are shown in FIGS. 14 and 18.

In one experiment, the performance of FveXyn4, *Fusarium verticilloides* was compared to Verenium's Xylathin™ (benchmark). Enzyme in Xylathin™ is a glycosyl hydrolase family 11 from uncultured (metagenomic) bacterium (U.S. Pat. No. 7,504,120).

TABLE 8.1

| | Viscosity in time (mPa*s) | | |
|---|---|---|---|
| | Blank | Xylathin ™ benchmark | FveXyn4 |
| After pretreatment (1200 sec. process time) | 626 | 361 | 183 |
| After liquefaction (3120 sec. process time) | 495 | 177 | 106 |
| At fermentation temperature (3660 sec. process time) | 1005 | 379 | 222 |
| Brix after RVA run | 27.50 ± 0.27 | 27.89 | 28.18 |

The Brix value is a measure of the concentration of dissolved substance, for instance sugars, in a watery liquid, or syrup in case of grain processing. It is used to quantify the solubilization/degradation process of the sugars. The higher the values, the more sugars are dissolved. Reference values are needed for comparison. Brix values are expressed in degrees and are measured using a refractometer.

These data together with FIG. 14 show that FveXyn4 outperforms Xylathin™ on viscosity.

In another experiment, the performance of FoxXyn2, *Fusarium oxysporum*) was compared to Verenium's Xylathin™ (benchmark). The enzyme in Xylathin™ is a glycosyl hydrolase family 11 from uncultured (metagenomic) bacterium (U.S. Pat. No. 7,504,120).

TABLE 8.2

| | Viscosity in time (mPa*s) | | |
|---|---|---|---|
| | Blank | Xylathin ™ benchmark | FoxXyn2 |
| After pretreatment (1200 sec. process time) | 626 | 361 | 204 |
| After liquefaction (3120 sec. process time) | 495 | 177 | 115 |
| At fermentation temperature (3660 sec. process time) | 1005 | 379 | 237 |
| Brix after RVA run | 27.50 ± 0.27 | 27.89 | 30.20 |

These data together with FIG. 18 show that FoxXyn2 outperforms Xylathin™ on viscosity.

Example 9

Wheat Gluten-Starch Separation

Separation of wheat flour into starch and gluten fractions is industrially applied on large scale to obtain high quality A-starch and byproducts B-starch and vital gluten.

Separation is improved by addition of xylanases.

9.1 Materials and Methods

The following assay simulates the wheat starch separation of a batter process at 40° C. In this assay, industrial wheat flour (Cargill) was added to preheated tap water (50° C.) to create a 35% DS slurry by mixing 1 minute in a kitchen blender (Braun). pH of the slurry remained 'as is' at ~6.1. 100 gram of this slurry was transferred to the Haake VT550 viscometer, which was calibrated at 40° C. After 1 minute of incubation, the enzyme solution was added to the slurry. Meanwhile, the viscosity profile was monitored before and after enzyme addition for 15 minutes in total. After incubation, triplicate samples of the incubated slurry and one sample of to slurry were taken for a spin test. Each spin test sample has a total weight of 22.5 g, which contains 15.8-15.9 g slurry sample added to 6.6-6.7 g of disposable centrifuge tube (15 ml). All samples were centrifuged in a Hermle Z400 centrifuge for 15 minutes at 3500 rpm. Brix values were determined from the syrup of the centrifuged samples.

Example 9A

In one experiment, the performance of xylanase FveXyn4 in accordance with the present invention in a wheat gluten-starch separation process was compared to the commercial enzymes, Shearzyme Plus™ (Novozymes). The commercial enzyme Shearzyme Plus™ was dosed at 0.20 kg/MT DS. Xylanase FveXyn4 was tested at a dose of 1.19 g protein/MT DS.

A 35% dry solids batter (pH 'as is' at ~6.1) was prepared by adding Cargill wheat flour to demineralized water preheated to 50° C., while continuously mixing it in a Braun blender for 1 minute at 18900 r.p.m. From this batter, 100 g was transferred to the Haake VT550 viscometer, preheated to 40° C. and stirring at γ=50 l/s. The viscosity was measured for 1 minute, after which enzymes were added and the viscosity was monitored for in total 15 minutes, see results in Table 1. The underlined values are viscosity values lower, or in other words better in performance, than those of the benchmark, Shearzyme Plus™. It is clear that xylanase FveXyn4 is significantly performing better than the benchmark Shearzyme Plus™.

In succession, three samples of the batter were immediately after incubation put in 15 ml disposable centrifuge tubes, each with a total weight of 22.5 g. The tubes were centrifuged for 15 minutes at 3500 r.p.m. in a Hermle Z400 centrifuge, and the individual layers were measured and averaged for the triplicates. Table 2 shows the percentage of each layer for the blanc, a batter without enzyme addition incubated in the Haake VT550 viscometer under the same conditions, and for all the xylanases tested. The underlined values of supernatant layer (%) are considerably larger than those of the benchmark, Shearzyme Plus™.

TABLE 9.1

The effect of xylanases on wheat flour viscosity in time, during a 15 minute incubation at 40° C.

| | Viscosity in time (mPA*s) | | |
|---|---|---|---|
| Time (min) | Blanc | Shearzyme Plus ™ (Benchmark) | FveXyn4 |
| 0 | 481.13 | 513.00 | 494.1 |
| 5 | 393.50 | 295.90 | 204.1 |
| 10 | 375.83 | 238.70 | 155.5 |
| 15 | 354.97 | 210.60 | 130.7 |
| Brix at $t_{15}$ | 5.88 | 6.07 | 6.32 |

TABLE 9.2

The effect of xylanases on wheat starch separation after 15 minute incubation at 40° C.

| Average of Separated layers (%) | Blanc | Shearzyme Plus ™ (Benchmark) | FveXyn4 |
|---|---|---|---|
| Starch | 33.74 | 34.6 | 34.3 |
| Fiber | 16.84 | 14.0 | 13.2 |
| Sludge | 24.22 | 23.3 | 20.2 |
| Supernatant | 25.20 | 28.1 | 32.3 |

Example 9B

In a second experiment, the performance of xylanase FoxXyn2 in a wheat starch separation process was compared to the commercial enzyme, Shearzyme Plus™. The commercial enzyme Shearzyme Plus™ was dosed at 0.20 kg/MT DS. Xylanase FoxXyn2 was tested at a dose of 1.19 gr protein/MT DS.

A 35% dry solids batter (pH 'as is' at ~6.1) was prepared by adding Cargill wheat flour to demineralized water preheated to 50° C., while continuously mixing it in a Braun blender for 1 minute at 18900 r.p.m. From this batter, 100 gr. was transferred to the Haake VT550 viscometer, preheated to 40° C. and stirring at γ=50 l/s. The viscosity was measured for 1 minute, after which enzymes were added and the viscosity was monitored for in total 15 minutes, see results in Table 1. The underlined values are viscosity values lower, or in other words better in performance, than those of the benchmark, Shearzyme Plus™. It is clear that xylanase FoxXyn2 is significantly performing better than the benchmark Shearzyme Plus™.

In succession, three samples of the batter were immediately after incubation put in 15 ml disposable centrifuge tubes, each with a total weight of 22.5 gr. The tubes were centrifuged for 15 minutes at 3500 r.p.m. in a Hermle Z400 centrifuge, and the individual layers were measured and averaged for the triplicates. Table 2 shows the percentage of each layer for the blanc, a batter without enzyme addition incubated in the Haake VT550 viscometer under the same conditions, and for all the xylanases tested. The underlined values of supernatant layer (%) are considerably larger than those of the benchmark, Shearzyme Plus.

TABLE 9.3

The effect of xylanases on wheat flour viscosity in time, during a 15 minute incubation at 40° C.

| Time (min) | Viscosity in time (mPA*s) | | |
|---|---|---|---|
| | Blanc | Shearzyme Plus ™ (Benchmark) | FveXyn4 |
| 0 | 481.13 | 513.00 | 488.4 |
| 5 | 393.50 | 295.90 | 203.05 |
| 10 | 375.83 | 238.70 | 152.25 |
| 15 | 354.97 | 210.60 | 126.35 |
| Brix at $t_{15}$ | 5.88 | 6.07 | 6.35 |

TABLE 9.4

The effect of xylanases on wheat starch separation after 15 minute incubation at 40° C.

| Average of Separated layers (%) | Blanc | Shearzyme Plus ™ (Benchmark) | FoxXyn2 |
|---|---|---|---|
| Starch | 33.74 | 34.6 | 34.1 |
| Fiber | 16.84 | 14.0 | 13.5 |
| Sludge | 24.22 | 23.3 | 19.9 |
| Supernatant | 25.20 | 28.1 | 32.5 |

Example 10

Cloning of *Fusarium oxysporum* Xylanase FoxXyn2

The nucleotide sequence of the FoxXyn2 gene isolated from *Fusarium oxysporum* is set forth as SEQ ID Nos 12, 13 and 14. The predicted intron is shown in SEQ ID No. 12 (FIG. 19) in italics and lowercase.

The amino acid sequence of the FoxXyn2 precursor protein is set forth as SEQ ID No. 9 (FIG. 15). The predicted signal sequence is shown in italics and lowercase.

The amino acid sequence of the predicted mature forms of FoxXyn2 is set forth as SEQ ID Nos. 10 and 11 (shown in FIGS. 15 and 17). SEQ ID No. 10 shows a section of the polypeptide that may be cleaved before full maturation of the protein. The active form of the protein may be with or without this section, and thus the active protein may have SEQ ID No. 10 or SEQ ID No. 11.

The protein product of gene FoxXyn2 belongs to glycosyl hydrolase family 10. This suggests that FoxXyn2 is a secreted glycosyl hydrolase.

Example 11

Expression of FoxXyn2 Protein

Figure 22:
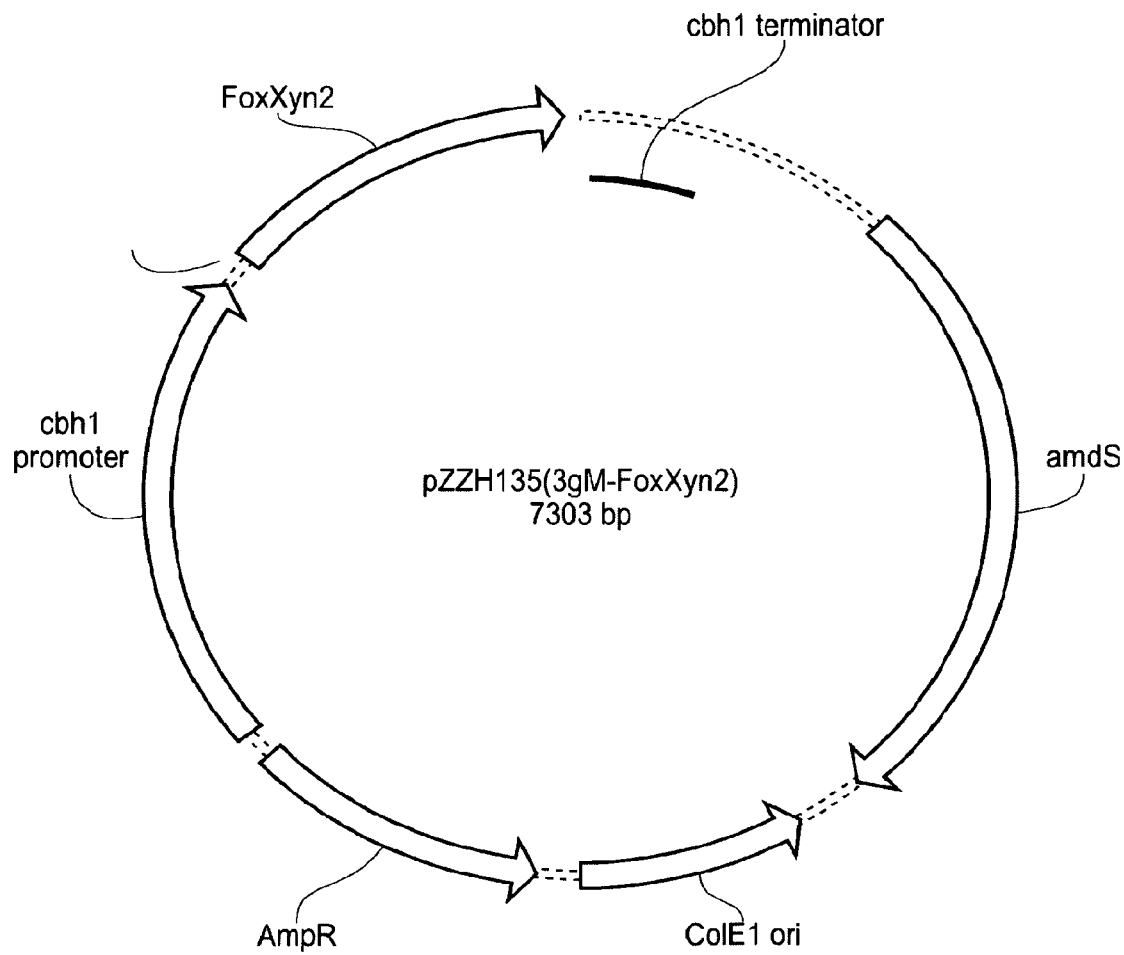
FIG. 22 shows a plasmid map of pZZH135.

The FoxXyn2 gene was amplified from genomic DNA of *Fusarium oxysporum* using the following primers: Primer 1 5'-ccgcggccgcaccATGAAGCTGTCTTCCTTCCTCTA-CACC-3' (SEQ ID NO:19), and Primer 2 5'-ccggcgcgccct-taTTAGCGGAGAGCGTTGACAACAG-3' (SEQ ID NO:20). After digested with Not I and Asc I, the PCR product was cloned into pTrex3gM expression vector (described in US 2011/0136197 A1) digested with the same restriction enzymes, and the resulting plasmid was labeled pZZH135. A plasmid map of pZZH135 is provided in FIG. 22. The sequence of the FoxXyn2 gene was confirmed by DNA sequencing.

The plasmid pZZH135 was transformed into a quad deleted *Trichoderma reesei* strain (described in WO 05/001036, incorporated herein by reference) using biolistic method (taught in Te'o V S et al., J Microbiol Methods, 51:393-9, 2002). The protein isolated from the culture supernatant after filtration was used to perform SDS-PAGE analysis and xylanase activity assay to confirm enzyme expression.

The nucleotide sequence of FoxXyn2 gene from expression plasmid pZZH135 is set forth as SEQ ID No. 12 (FIG. 19). The signal sequence is shown in bold, and the predicted intron is shown in italics and lowercase.

The amino acid sequence of FoxXyn2 protein expressed from plasmid pZZH135 is set forth as SEQ ID No. 9 (FIG. 15). The signal sequence is shown in italics.

The amino acid sequence of the mature form of FoxXyn2 protein is set forth as SEQ ID No. 10 (FIG. 16).

FoxXyn2 protein was purified from culture supernatant using affinity chromatography resin Blue Sepharose, 6FF, and samples were used for biochemical characterization as described in subsequent examples.

Example 12

Xylanase Activity of FoxXyn2

FoxXyn2 belongs to the glycosyl hydrolase 10 family (GH10, CAZy number). The beta 1-4 xylanase activity of FoxXyn2 was measured using 1% xylan from birch wood (Sigma 95588) or 1% arabinoxylan from wheat flour (Megazyme P-WAXYM) as substrates. The assay was performed in 50 mM sodium citrate pH 5.3, 0.005% Tween-80 buffer at 50° C. for 10 minutes. The released reducing sugar was quantified by reaction with 3,5-Dinitrosalicylic acid and measurement of absorbance at 540 nm. The enzyme activity is quantified relative to a xylose standard curve. In this assay, one xylanase unit (U) is defined as the amount of enzyme required to generate 1 micromole of xylose reducing sugar equivalents per minute under the conditions of the assay.

Example 13 pH Profile of FoxXyn2

Figure 23:
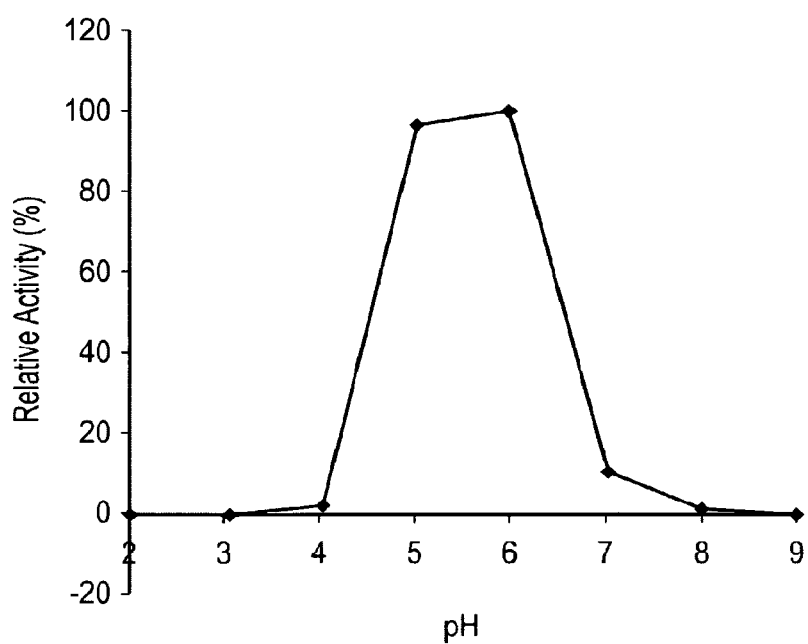
FIG. 23 shows the pH profile of FoxXyn2.

The pH profile of FoxXyn2 was determined using xylan from birch wood (Sigma 95588) as substrate. The assay was performed in Sodium Citrate/Sodium Phosphate buffer solution adjusted to pH values between 2 and 9. Birchwood xylan (2% solution) dissolved in water was mixed with equal volume of 50 mM Citrate/Phosphate buffer solution in a 96-well plate, and the substrate was equilibrated at 50° C. before adding enzyme. After 10 minutes, the enzyme reaction was stopped by transferring 60 microliters of reaction mixture to a 96-well PCR plate containing 100 microliters of DNS solution. The PCR plate was heated at 95° C. for 5 minutes in a Bio-Rad DNA Engine. Then plate was cooled to room temperature and 100 microliters were transferred from each well to a new 96-well plate. Release of reducing sugars from the substrate was quantified by measuring the optical density at 540 nm in a spectrophotometer. Enzyme activity at each pH was reported as relative activity where the activity at the pH optimum was set to 100%. The pH profile of FoxXyn2 is shown in FIG. 23. FoxXyn2 was found to have an optimum pH at about 6, and was found to retain greater than 50% of maximum activity between pH 4.5 and 6.5.

Example 14

Temperature Profile of FoxXyn2

Figure 24:
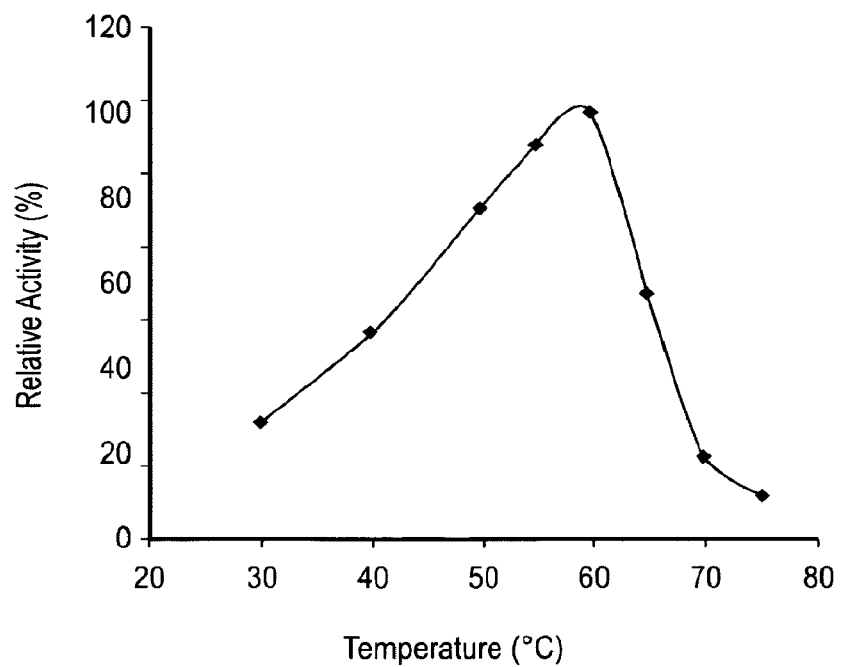
FIG. 24 shows the temperature profile of FoxXyn2.

The temperature optimum of purified FoxXyn2 was determined by assaying for xylanase activity at temperatures varying between 45° C. and 94° C. for 10 minutes in 50 mM sodium citrate buffer at pH 5.3. The activity was reported as relative activity where the activity at the temperature optimum was set to 100%. The temperature profile of FoxXyn2 is shown in FIG. 24. FoxXyn2 was found to have an optimum temperature of 60° C., and was found to retain greater than 50% of maximum activity between 40° C. and 65° C.

Example 15

FveXyn4 in Animal Feed—Pigs 15.1 Materials and Methods

Two experiments are conducted to evaluate the efficacy of FveXyn4 in corn/corn DDGS based diets (Experiment 1) and wheat/wheat bran based diets (Experiment 2). An Animal Care and Use Committee approves the use of the pigs and relevant welfare guidelines for the Country are used. Each experiment used a total of 48 pigs ([♀ Yorkshire× Landrace]×♂Duroc) housed in groups of two and each pen contained a gilt and a barrow. Each pen has a smooth transparent plastic sides and plastic-covered expanded metal sheet flooring in a temperature-controlled room (22±2° C.).

TABLE 15.1

Basal diets

| Item | Experiment 1 | Experiment 2 |
|---|---|---|
| Corn | 41.44 | |
| US corn DDGS | 40.00 | |
| Hard Wheat | | 56.57 |
| Wheat Bran | | 5.06 |
| Wheat middlings | | 19.94 |
| Soybean Meal | 15.00 | 13.50 |
| Tallow | | 0.99 |
| L-Lysine HCl | 0.75 | 0.73 |
| DL-Methionine | 0.10 | 0.17 |
| L-Threonine | 0.25 | 0.30 |
| L-Tryptophan | 0.06 | 0.01 |
| Digestibility marker (celite) | 0.30 | 0.30 |
| Salt | 0.30 | 0.47 |
| Limestone | 1.30 | 1.38 |
| Monocalcium Phosphate | 0.00 | 0.08 |
| Vitamins/Trace minerals premix[1] | 0.50 | 0.50 |
| Calculated provisions | | |
| Crude protein, % | 21.44 | 19.11 |
| Net energy, MJ/kg | 8.88 | 8.88 |
| SID Lysine g/NE MJ | 1.31 | 1.31 |
| SID Lysine, % | 1.16 | 1.16 |
| SID Methionine, % | 0.35 | 0.35 |
| Neutral detergent fibre, % | 20.63 | 17.93 |
| Calcium, % | 0.67 | 0.68 |
| Available phosphorous, % | 0.22 | 0.22 |

[1]The vitamin and trace mineral premix provided the following (per kg of diet): vitamin A, 11,000 IU; vitamin D3, 2,756 IU; vitamin E, 55 IU; vitamin B12, 55 μg; riboflavin, 16,000 mg; pantothenic acid, 44.1 mg; niacin, 82.7 mg; Zn, 150 mg; Fe, 175 mg; Mn, 60 mg; Cu, 17.5 mg; I, 2 mg; and Se, 0.3 mg Respective basal diets are formulated to meet the NRC nutrients recommendations for swine (NRC, 1998 Table 15.1). In each experiment, one batch of the basal diet is manufactured and split into four portions and each portion subsequently mixed with additives identified in Table 15.2. In experiment 1, pigs are offered the experimental diets for 42 days, whilst in experiment 2 pigs are offered the experimental diets of for 21 days. Feed and water is freely available at all times during experimentation. There are 4 replicate pens per treatment in each experiment; pen allocation to the treatments is randomized based on pig body weight at the start of the experiment. Body weight and Feed intake are recorded on a weekly basis and used to calculate feed conversion ratio. The growth performance data (BW, ADFI, ADO and FCR) are subjected to mixed-liner model using the GLM procedures of SAS.

TABLE 15.2

Treatments identification

| Diet | Treatment ID | Phytase[1] (FTU/kg of feed) | Xylanase |
|---|---|---|---|
| Control | 1 | 500 FTU | 0 |
| Control + FveXyn4 | 2 | 500 FTU | 2000 U/kg |
| Control + Commercial xylanase[2] | 3 | 500 FTU | 75 ppm |

[1]Phytase from Danisco Animal Nutrition
[2]Econase XT ® from AB Vista (sometimes referred to herein as AB Vista)

15.2 Results and Discussion

Compared with the control. FveXyn4 improves animal weight gain in both corn (Table 15.3) and wheat (Table 15.4) based diets. Furthermore, FveXyn4 has numerically superior effect % on growth performance relative to commercially available feed xylanase, particularly in corn based diets. This demonstrates the efficaciousness of FveXyn4 in mitigating the negative effects of the insoluble and soluble fibrous fractions in cereal ingredients on swine performance and shows better utilization of energy contained in the fibre component of cereal grains.

TABLE 15.3

Experiment 1: Effect of new xylanase on growth performance of growing pigs fed corn-corn DDGS based diets

| | Initial body weight, kg | Final body weight, kg | Average daily feed intake, grams/day | Average daily gain, grams/day | Feed conversion ratio, g/g |
|---|---|---|---|---|---|
| Control | 32.5 | 68.18b | 2285 | 849b | 2.69 |
| FveXyn4 | 32.9 | 74.09a | 2391 | 972a | 2.46 |

TABLE 15.3-continued

Experiment 1: Effect of new xylanase on growth performance of growing pigs fed corn-corn DDGS based diets

| | Initial body weight, kg | Final body weight, kg | Average daily feed intake, grams/day | Average daily gain, grams/day | Feed conversion ratio, g/g |
|---|---|---|---|---|---|
| Commercial xylanase (Econase ® XT) | 32.8 | 71.0ab | 2220 | 909ab | 2.43 |
| SEM | 0.69 | 2.18 | 154 | 43.5 | 0.11 |

TABLE 15.4

Experiment 2: Effect of new xylanase on growth performance of growing pigs fed wheat-wheat bran based diets

| | Initial body weight, kg | Final body weight, kg | Average daily feed intake, grams/day | Average daily gain, grams/day | Feed conversion ratio, g/g |
|---|---|---|---|---|---|
| Control | 50.5 | 66.3 | 2221 | 753b | 2.98a |
| FveXyn4 | 49.0 | 69.1 | 2332 | 955a | 2.46ab |
| Commercial xylanase (Econase ® XT) | 49.7 | 69.4 | 2464 | 935a | 2.66ab |
| SEM | 1.53 | 1.99 | 172 | 56.4 | 0.24 |

Example 16

FveXyn4 in Animal Feed—Pigs

16.1 Materials and Methods

An experiment is conducted to evaluate the efficacy of FveXyn4 in wheat/wheat bran based diets. Animal use and experimental procedures are approved by an Animal Care Committee and relevant welfare guidelines for the Country were used. Growing gilts ([Yorkshire×Landrace ♀]×Duroc ♂) are obtained from a Research Unit and upon arrival, pigs are weighed and based on body weight randomly assigned to pens to give 8 pens per treatment. The pens are equipped with a feeder, a nipple type drinker and plastic-covered expanded metal floors and a wall partitioning between pens that allowed visual contact with pigs in adjacent pens. The room temperature was maintained at 22+2° C. throughout the experiment.

TABLE 16.1

Composition of the basal diet

| Item | Level |
|---|---|
| Hard Wheat | 56.57 |
| Wheat Bran | 5.06 |
| Wheat middlings | 19.94 |
| Soybean Meal | 13.50 |
| Soybean oil | 0.99 |
| L-Lysine HCl | 0.73 |
| DL-Methionine | 0.17 |
| L-Threonine | 0.30 |
| L-Tryptophan | 0.01 |
| Digestibility marker (celite) | 0.30 |
| Salt | 0.47 |
| Limestone | 1.38 |
| Monocalcium Phosphate | 0.08 |
| Vitamins/Trace minerals premix[1] | 0.50 |
| Calculated provisions | |
| Crude protein, % | 19.11 |
| Net energy, MJ/kg | 8.88 |
| SID Lysine g/NE MJ | 1.31 |
| SID Lysine, % | 1.16 |
| SID Methionine, % | 0.35 |
| Neutral detergent fibre, % | 17.93 |
| Calcium, % | 0.68 |
| Available phosphorous, % | 0.22 |

[1]Provided per kg of complete diet: vitamin A, 8255 IU; vitamin D3, 1000 IU; vitamin E, 20 IU; vitamin K, 1.5 mg; riboflavin, 7.5 mg; niacin, 30 mg; vitamin B12, 25 µg; pyridoxine, 4.5 mg; biotin, 200 µg; folic acid, 1 mg; thiamin, 4 mg; choline, 781 mg; copper, 10 mg; iodine, 0.6 mg; iron, 130 mg; manganese, 40 mg; selenium, 0.3 mg; zinc, 130 mg.

A basal diet is formulated to meet the NRC nutrients recommendations for swine (NRC, 1998; Table 16.1). One batch of the basal diet is manufactured and split into four portions and each portion subsequently mixed with additives identified in Table 16.2. The 4 treatments are allotted in a completely randomized design to give 8 pens per treatment. Pigs are offered the experimental diets for 42 days during which feed and water are freely available at all times. Body weight and Feed intake are recorded on a weekly basis and used to calculate feed conversion ratio. The growth performance data (BW, ADFI, ADG and FCR) are subjected to mixed-liner model using the GLM procedures of SAS

TABLE 16.2

Treatments identification

| Diet | Treatment ID | Phytase[1] (FTU/kg of feed) | Xylanase |
|---|---|---|---|
| Control | 1 | 500 FTU | 0 |
| Control + FveXyn4 | 2 | 500 FTU | 2000 U/kg |
| Control + Commercial xylanase[2] | 3 | 500 FTU | 75 ppm |

[1]Phytase from Danisco Animal Nutrition
[2]Econase XT ® from AB Vista

16.2 Results and Discussion

FveXyn4 results in better body weight gain, specifically 9.9% higher average daily gain (over 42 days) than a commercial xylanase from AB Vista. Pigs exhibited a better FCR and heavier final body weight when receiving FveXyn4.

TABLE 16.3

Effect of new xylanase on growth performance of growing pigs fed wheat based diets

| | Initial body weight, kg | Final body weight, kg | Average daily feed intake, grams/day | Average daily gain, grams/day | Feed conversion ratio, g/g |
|---|---|---|---|---|---|
| Control | 23.9 | 61.8 | 2104 | 904ab | 2.33 |
| FveXyn4 | 23.0 | 63.1 | 2075 | 954a | 2.18 |

TABLE 16.3-continued

Effect of new xylanase on growth performance of growing pigs fed wheat based diets

| | Initial body weight, kg | Final body weight, kg | Average daily feed intake, grams/day | Average daily gain, grams/day | Feed conversion ratio, g/g |
|---|---|---|---|---|---|
| Commercial xylanase (Econase ® XT) | 23.2 | 59.6 | 2021 | 868b | 2.33 |
| SEM | 0.48 | 1.16 | 61.2 | 23.7 | 0.07 |

Example 17

FveXyn4 in Animal Feed—Pigs 17.1 Materials and Methods

The experiment is conducted to evaluate the efficacy of FveXyn4 on ileal nutrients and energy digestibility in growing pigs fed wheat/wheat bran based diets. The protocol for the experiment is reviewed and approved by an Institutional Animal Care and Use Committee and relevant welfare guidelines for the Country are used. Six growing barrows (initial body weight of 30 kg) are equipped with a T-cannula in the distal ileum for the purpose of the experiment. Pigs are of the off springs of G-Performer boars that were mated to Fertilium 25 females (Genetiporc, Alexandria, MN, USA) and are housed in individual pens (1.2×1.1 m) in an environmentally controlled room. Each pen is equipped with a feeder and a nipple drinker and has fully slatted concrete floors.

TABLE 17.1

Composition of the basal diet

| Item | Level |
|---|---|
| Hard Wheat | 56.57 |
| Wheat Bran | 5.06 |
| Wheat middlings | 19.94 |
| Soybean Meal | 13.50 |
| Soybean oil | 0.99 |
| L-Lysine HCl | 0.73 |
| DL-Methionine | 0.17 |
| L-Threonine | 0.30 |
| L-Tryptophan | 0.01 |
| Digestibility marker (celite) | 0.30 |
| Salt | 0.47 |
| Limestone | 1.38 |
| Monocalcium Phosphate | 0.08 |
| Vitamins/Trace minerals premix[1] | 0.50 |
| Calculated provisions | |
| Crude protein, % | 19.11 |
| Net energy, MJ/kg | 8.88 |
| SID Lysine g/NE MJ | 1.31 |
| SID Lysine, % | 1.16 |
| SID Methionine, % | 0.35 |
| Neutral detergent fibre, % | 17.93 |
| Calcium, % | 0.68 |
| Available phosphorous, % | 0.22 |

[1]Provided the following quantities of vitamins and trace minerals per kilogram of complete diet: Vitamin A as retinyl acetate, 11,128 IU; vitamin $D_3$ as cholecalciferol, 2,204 IU; vitamin E as DL-alpha tocopheryl acetate, 66 IU; vitamin K as menadione nicotinamide bisulfite, 1.42 mg; thiamin as thiamine mononitrate, 0.24 mg; riboflavin, 6.58 mg; pyridoxine as pyridoxine hydrochloride, 0.24 mg; vitamin $B_{12}$, 0.03 mg; D-pantothenic acid as D-calcium pantothenate, 23.5 mg; niacin as nicotinamide and nicotinic acid, 44 mg; folic acid, 1.58 mg; biotin, 0.44 mg; Cu, 10 mg as copper sulfate; Fe, 125 mg as iron sulfate; I, 1.26 mg as potassium iodate; Mn, 60 mg as manganese sulfate; Se, 0.3 mg as sodium selenite; and Zn, 100 mg as zinc oxide.

TABLE 17.2

Treatments identification

| Diet | Treatment ID | Phytase[1] (FTU/kg of feed) | Xylanase |
|---|---|---|---|
| Control | 1 | 500 FTU | 0 |
| Control + FveXyn4 | 2 | 500 FTU | 2000 U/kg |
| Control + Commercial xylanase[2] | 3 | 500 FTU | 75 ppm |

[1]Phytase from Dan sco Animal Nutrition
[2]Econase XT ® from AB Vista

A basal diet is formulated to meet the NRC nutrients recommendations for swine (Table 17.1). One batch of the basal diet is manufactured and split into four portions and each portion subsequently mixed with additives identified in Table 17.2. The experiment was designed and conducted according to a 4×4 Latin square design with 2 added columns to give 6 replicates per diet. All pigs are fed at a level of 3 times their maintenance energy requirement (106 kcal ME per $kg^{075}$; NRC, 1998), and provided at 0800 and 1700 h. Animals have free access to water through a bowl-type drinker. Pig weights are recorded at the beginning and at the end of each period and the amount of feed supplied each day is recorded. Each experimental period lasted for 7 d. The initial 5 days of each period is considered an adaptation period to the diet. Ileal digesta are collected for 8 h on d 6 and 7 using standard operating procedures. In brief, a plastic bag is attached to the cannula barrel and digesta flowing into the bag is collected. Bags are removed whenever they are filled with digesta—or at least once every 30 min and are immediately frozen at −20° C. On the completion of one experimental period, animals are deprived of feed overnight and the following morning, a new experimental diet is offered.

At the end of the experiment, ileal samples are thawed, mixed within animal and diet, and a sub-sample is collected for chemical analysis. A sample of basal diet is also collected and analyzed. Digesta samples are lyophilized and finely ground prior to chemical analysis. All samples are analyzed for dry matter. Titanium, gross energy, crude protein, fat and neutral detergent fibre according to standard procedures (AOAC, 2005). The values for apparent ileal digestibility of energy and nutrients are calculated as described previously (Stein et al., 2007 Livestock Science, 2007 vol. 109, issue 1 part 3 p282-285 and J ANIM SCI January 2007 vol. 85 no. 1 172-180). Data are analyzed using the MIXED procedures of SAS.

17.2 Results and Discussion

Results indicate that pigs fed FveXyn4 have significantly higher ($P<0.05$) apparent ileal digestibility of crude protein and fat than control and the commercial xylanase fed pigs (Table 17.3). Results suggest that FveXyn4 is effective in unlocking energy in fibrous feed fed to growing pigs by breaking down fibres. Indeed, pigs fed FveXyn4 show increased fibre digestibility by a range of 6 to 11 percentage units relative to the control and commercial xylanase (Table 17.3). Subsequently pigs fed FveXyn4 extract 106 and 219 kcal extra (Table 17.3) energy compared to pigs fed the control and commercial xylanase, respectively.

TABLE 17.3

Effect of new xylanase on apparent ileal nutrients and fibre energy digestibility (%) and energy utilization (kcal/kg) in growing pigs fed wheat based diets

| | Dry matter | Crude protein | Fat | Neutral detergent fibre | Energy |
|---|---|---|---|---|---|
| Control | 68.0ab | 74.7b | 62.2b | 66.3ab | 3,168ab |
| FveXyn4 | 71.2a | 77.0a | 67.7a | 72.1a | 3,274a |
| Commercial xylanase (Econase ® XT) | 65.8b | 74.6b | 56.3b | 61.3b | 3,055b |
| SEM | 1.44 | 0.84 | 2.03 | 2.65 | 47.6 |

Example 18

FveXyn4 in Animal Feed—Pigs 18.1 Materials and Methods

The efficacy of FveXyn4 on ileal and total tract nutrients and energy digestibility in growing pigs fed corn-corn DDGS and wheat/wheat bran based diets is studied. An Animal Care and Use Committee approves the use of the pigs and pigs are cared for according to the relevant welfare guidelines for the Country. A total of 24 barrows ([♀Yorkshire×Landrace]×♂ Duroc; initial body weight of 30 kg) are equipped with a T-cannula in the distal ileum for the purpose of the experiment. The pigs are individually housed in metabolism crates that a smooth transparent plastic sides and plastic-covered expanded metal sheet flooring in a temperature-controlled room (22±2° C.).

TABLE 18.1

Basal diets used

| Item | Corn based | Wheat based |
|---|---|---|
| Corn | 41.44 | |
| US corn DDGS | 40.00 | |
| Hard Wheat | | 56.57 |
| Wheat Bran | | 5.06 |
| Wheat middlings | | 19.94 |
| Soybean Meal | 15.00 | 13.50 |
| Tallow | | 0.99 |
| L-Lysine HCl | 0.75 | 0.73 |
| DL-Methionine | 0.10 | 0.17 |
| L-Threonine | 0.25 | 0.30 |
| L-Tryptophan | 0.06 | 0.01 |
| Digestibility marker (celite) | 0.30 | 0.30 |
| Salt | 0.30 | 0.47 |
| Limestone | 1.30 | 1.38 |
| Monocalcium Phosphate | 0.00 | 0.08 |
| Vitamins/Trace minerals premix[1] | 0.50 | 0.50 |
| Calculated provisions | | |
| Crude protein, % | 21.44 | 19.11 |
| Net energy, MJ/kg | 8.88 | 8.88 |
| SID Lysine g/NE MJ | 1.31 | 1.31 |
| SID Lysine, % | 1.16 | 1.16 |
| SID Methionine, % | 0.35 | 0.35 |
| Neutral detergent fibre, % | 20.63 | 17.93 |
| Calcium, % | 0.67 | 0.68 |
| Available phosphorous, % | 0.22 | 0.22 |

[1]The vitamin and trace mineral premix provided the following (per kg of diet): vitamin A, 11,000 IU; vitamin D3, 2,756 IU; vitamin E, 55 IU; vitamin B12, 55 µg; riboflavin, 16,000 mg; pantothenic acid, 44.1 mg; niacin, 82.7 mg; Zn, 150 mg; Fe, 175 mg; Mn, 60 mg; Cu, 17.5 mg; I, 2 mg; and Se, 0.3 mg Respective basal diets are formulated to meet the NRC nutrient recommendations for swine (NRC, 1998 Table 18.1). In each experiment, one batch of the basal diet is manufactured and split into four portions and each portion subsequently mixed with additives identified in Table 18.2.

TABLE 18.2

Treatments identification

| Diet | Treatment ID | Phytase[1] (FTU/kg of feed) | Xylanase |
|---|---|---|---|
| Control | 1 | 500 FTU | 0 |
| Control + FveXyn4 | 2 | 500 FTU | 4000 U/kg |
| Control + Commercial xylanase[2] | 3 | 500 FTU | 100 ppm |

[1]Phytase from Danisco Animal Nutrition
[2]Econase XT ® from AB Vista

The experiment is designed and conducted as two period cross-over design in which all corn diets are run in period one and all wheat diets run in period two. Within a period, the 4 treatments will be allocated to pigs in a completely randomized design to give 6 replicates per treatment. Pigs are fed a common commercial diet for a week before commencement of the second period. The pigs are fed their respective diets in two equal portions at 0830 and 1630. Daily feed allowance is based on the pig's BW at the beginning of the period and is calculated to supply 2.6 times the estimated maintenance requirements. Each experimental period lasts for 14 d: d 7 for adaptation, d 8 and 9 for grab fecal collection and d 10 and 11 for ileal digesta collection to examine coefficient of apparent ileal and total tract digestibility of N, DM, energy and crude fat. Pigs are allowed free accessible to water from nipple drinkers located in each pen at all times. Digesta flow measurements and blood samples collection are conducted from d 12 to 14. Data id analysed using GLM procedures of SAS. Statistical significance is accepted at $P<0.05$.

18.2 Results and Discussion

Preliminary results indicate that pigs fed FveXyn4 have significantly improved energy digestibility.

Example 19

FveXyn4 in Animal Feed (Poultry)

19.1 Materials and Methods

An experiment is conducted to evaluate the efficacy of FveXyn4 on growth performance of broiler chickens fed corn/corn DDGS based diets and wheat/wheat bran based diets. The experimental procedures are approved by an Animal Ethics Committee and, complied with relevant welfare guidelines for the Country. A two-phase feeding programme (starter and finisher) is used (Table 1). The starter and finisher diets are offered from d 0 to 21 and 22 to 42, respectively.

TABLE 19.1

Composition of the basal diets[1]

| | Starter, d 0-21 | | Finisher, d 22-42 | |
|---|---|---|---|---|
| | Corn | Wheat | Corn | Wheat |
| Corn | 57.39 | — | 58.50 | — |
| Corn DDGS | 11.00 | — | 15.00 | — |
| Wheat | — | 60.17 | — | 63.30 |

TABLE 19.1-continued

Composition of the basal diets[1]

|  | Starter, d 0-21 | | Finisher, d 22-42 | |
| --- | --- | --- | --- | --- |
|  | Corn | Wheat | Corn | Wheat |
| Wheat bran | — | 9.00 | — | 13.00 |
| Soybean meal, 45% | 26.50 | 22.34 | 19.00 | 14.00 |
| Tallow | 1.75 | 4.85 | 3.20 | 5.95 |
| Vitamin-mineral premix2 | 0.33 | 0.33 | 0.33 | 0.33 |
| Sodium bicarbonate | 0.20 | 0.22 | 0.20 | 0.29 |
| Salt | 0.38 | 0.38 | 0.34 | 0.35 |
| Monocalcium Phosphate | 0.35 | 0.37 | 0.13 | 0.20 |
| Limestone | 1.700 | 1.69 | 1.70 | 1.65 |
| L-Lysine HCl | 0.135 | 0.25 | 0.20 | 0.34 |
| DL-methionine | 0.185 | 0.23 | 0.13 | 0.19 |
| L-threonine | 0.100 | 0.19 | 0.09 | 0.22 |
| Calculated provisions | | | | |
| Crude protein | 21.0 | 21.1 | 18.6 | 18.2 |
| ME (MJ/kg) | 12.5 | 12.2 | 12.9 | 12.5 |
| Calcium | 0.81 | 0.80 | 0.75 | 0.73 |
| Available phosphorous | 0.25 | 0.25 | 0.21 | 0.21 |
| Sodium | 0.23 | 0.22 | 0.23 | 0.22 |
| Digestible Lysine | 1.01 | 0.99 | 0.90 | 0.87 |
| Digestible Methionine | 0.47 | 0.47 | 0.39 | 0.39 |
| Digestible Threonine | 0.74 | 0.74 | 0.64 | 0.66 |
| Digestible Tryptophan | 0.19 | 0.21 | 0.16 | 0.17 |

[1]A commercial phytase from Danisco Animal Nutrition top dressed to supply 500 FTU of final feed
2Supplied per kilogram of diet: antioxidant, 100 mg; biotin, 0.2 mg; calcium pantothenate, 12.8 mg; cholecalciferol, 60 μg; cyanocobalamin, 0.017 mg; folic acid, 5.2 mg; menadione, 4 mg; niacin, 35 mg; pyridoxine, 10 mg; trans-retinol, 3.33 mg; riboflavin, 12 mg; thiamine, 3.0 mg; dl-a-tocopheryl acetate, 60 mg; choline chloride, 638 mg; Co, 0.3 mg; Cu, 3.0 mg; Fe, 25 mg; I, 1 mg; Mn, 125 mg; Mo, 0.5 mg; Se, 200 μg; Zn, 60 mg.

Two basal diets, one based on wheat/wheat bran and soybean meal, and the other based on corn/corn DDGS and soybean meal, are formulated to meet or exceed the recommended requirements for nutrients, except AME, for broilers (Table 19.1). From each basal diet, four experimental diets are developed to constitute control, FveXyn4, commercial xylanases 1 and commercial xylanases 2 as identified in Table 19.2.

TABLE 19.2

Treatments identification

| Diet | Treatment ID | Phytase[1] (FTU/kg of feed) | Xylanase |
| --- | --- | --- | --- |
| Control | 1 | 500 FTU | 0 |
| Control + FveXyn4 | 2 | 500 FTU | 1250 U/kg |
| Control + Commercial xylanase[2] | 3 | 500 FTU | 50 ppm |

[1]Phytase from Danisco Animal Nutrition
[2]Econase XT ® from AB Vista

Male broiler (Ross 308) chicks are obtained as day-olds from a commercial hatchery. The chicks are individually weighed and allocated to 72 brooder cages (8 chicks per cage) and the 8 dietary treatments randomly assigned to eight cages each. On day 12, the birds are transferred to grower cages. The space allocation per bird in brooder and grower cages is 530 and 640 cm$^2$, respectively. The brooder and grower cages are housed in environmentally controlled rooms. The temperature is maintained at 31° C. in the first week and then gradually reduced to 22° C. by the end of third week. The birds receive 20 hours fluorescent illumination and, allowed free access to the diets and water. Body weights and feed intake are recorded at weekly intervals throughout the 42-day experimental period. Mortality is recorded daily. Any bird that dies is weighed and the weight is used to adjust FCR. Feed conversion ratios are calculated by dividing total feed intake by weight gain of live plus dead birds. Data are analysed as a two-way factorial arrangement of treatments using the General Linear Models procedure of SAS (2004).

19.2 Results and Discussion

Compared with the control and commercial xylanase 2, FveXyn4 improves gain and FCR in both corn and wheat based diets (Table 19.3). This demonstrates the efficaciousness of FveXyn4 in mitigating the negative effects of the insoluble and soluble fibrous fractions in cereal ingredients that may limit poultry performance.

TABLE 19.3

Effect of new xylanase on growth performance of broiler chickens fed corn-corn DDGS and wheat/wheat bran based diets

| Treatments | | Initial body weight, g | Final body weight, g | Feed intake, g | Body weight gain, g | Feed conversion ratio, g/g |
| --- | --- | --- | --- | --- | --- | --- |
| Grain | Xylanase | | | | | |
| Corn | Control | 38.3 | 2151 | 3738 | 2113 | 1.81 |
| Corn | FveXyn4 | 38.3 | 2306 | 3946 | 2268 | 1.76 |
| Corn | Commercial xylanase | 38.5 | 2304 | 3969 | 2265 | 1.78 |
| Wheat | Control | 38.4 | 2477 | 4056 | 2438 | 1.72 |
| Wheat | FveXyn4 | 38.3 | 2678 | 4294 | 2639 | 1.69 |
| Wheat | Commercial xylanase | 38.2 | 2456 | 4077 | 2418 | 1.71 |
| SEM | | 0.17 | 56.5 | 105 | 56.5 | 0.02 |
| Main effects, grains | | | | | | |
| Corn | | 38.3 | 2252b | 3851b | 2214b | 1.77a |
| Wheat | | 38.3 | 2588a | 4165a | 2550a | 1.68b |
| SEM | | 0.09 | 28.2 | 52.5 | 28.2 | 0.01 |
| Main effects, xylanases | | | | | | |
| Control | | 38.3 | 2314b | 3847 | 2275b | 1.76a |
| FveXyn4 | | 38.3 | 2492a | 4120 | 2453a | 1.72b |

TABLE 19.3-continued

Effect of new xylanase on growth performance of broiler chickens fed corn-corn DDGS and wheat/wheat bran based diets

| Treatments | Initial body weight, g | Final body weight, g | Feed intake, g | Body weight gain, g | Feed conversion ratio, g/g |
|---|---|---|---|---|---|
| Commercial xylanase | 38.3 | 2380b | 4023 | 2342b | 1.74ab |
| SEM | 0.12 | 39.9 | 74.3 | 39.9 | 0.01 |
| Probabilities | | | | | |
| Grain | — | <0.01 | <0.01 | <0.01 | <0.01 |
| Xylanase | — | <0.01 | 0.22 | <0.01 | <0.01 |
| Grain and xylanase interaction | — | 0.04 | 0.37 | 0.04 | 0.05 |

Within a column, means with different letters are significantly different, ($P < 0.05$).

Example 20

FveXyn4 in Animal Feed (Poultry)

20.1 Material and Methods

The experiment is conducted to evaluate the efficacy of FveXyn4 on energy and nutrient utilization/retention in broiler chickens fed corn/corn DDGS based diets. An Animal Care and Use Committee approved all bird handling and collection procedures. Two-hundred fifty-six male broiler chicks (Ross 708, Aviagen, Huntsville, AL) are housed in electrically heated battery cages (model SB 4 T, Alternative Design Manufacturing, Siloam Springs, AR) in an environmentally controlled room for a 21 day trial. Battery temperatures on d 1 to 8, d 8 to 15, and d 15 to 21 are kept at 35, 32, and 27° C., respectively.

A corn-based basal diet (Table 20.1) is formulated to meet the nutrient requirements of the broiler chicken. From the basal diet, four experimental diets are developed to constitute control, FveXyn4, and commercial xylanase as identified in Table 20.2.

TABLE 20.1

Composition of the basal diet

| Ingredients | Levels |
|---|---|
| Corn | 554.4 |
| Corn-DDGS | 110.0 |
| Soybean Meal | 244.4 |
| Soybean Oil | 10.0 |
| L-Lysine HCl | 4.3 |
| DL-Methionine | 2.7 |
| L-Threonine | 1.1 |
| Sodium Bicarbonate | 2.0 |
| Salt | 2.2 |
| Limestone (A) | 15.3 |
| MCP (B) | 5.6 |
| Vitamin/Trace minerals premix (C) | 3.0 |
| TiO2 Premix (D) | 25.0 |
| Phytase premix (E) | 10.0 |
| Calculated provisions | |
| Crude protein, g/kg | 211.4 |
| MEP, MJ/kg | 115.1 |
| Calcium, g/kg | 8.9 |

TABLE 20.1-continued

Composition of the basal diet

| Ingredients | Levels |
|---|---|
| Available phosphorous, g/kg | 2.8 |
| Digestible Lysine, g/kg | 11.5 |
| Digestible Methionine, g/kg | 5.5 |

(A) 38% Ca
(B) 16% Ca, 21% P.
(C) Supplies the following per kg DIET: Vit. A, 5484 IU; Vit. D3, 2643 ICU; Vit E, 11 IU; Menadione sodium bisulfite, 4.38 mg; Riboflavin, 5.49 mg; d-pantothenic acid, 11 mg; Niacin, 44.1 mg; Choline chloride, 771 mg; Vit B12, 13.2 ug; Biotin, 55.2 ug; Thiamine mononitrate, 2.2 mg; Folic acid, 990 ug; Pyridoxine hydrochloride, 3.3 mg; I, 1.11 mg; Mn, 66.06 mg; Cu, 4.44 mg; Fe, 44.1 mg; Zn, 44.1 mg; Se, 300 ug. Also contains per g of premix: Vit. A, 1828 IU; Vit. D3, 881 ICU; Vit E.3.67 IU; Menadione sodium bisulfite, 1.46 mg; Riboflavin, 1.83 mg; d-pantothenic acid, 3.67 mg; Niacin, 14.69 mg; Choline chloride, 257 mg; Vit B12, 4.4 ug; Biotin, 18.4 ug; Thiamine mononitrate, 735 ug; Folic acid, 330 ug; Pyridoxine hydrochloride, 1.1 mg; I, 370 ug; Mn, 22.02 mg; Cu, 1.48 mg; Fe, 14.69 mg; Zn, 14.69 mg; Se, 100 ug.
(D) Prepared as 5 g of TiO2 added to 20 g of fine ground SBM.
(E) Prepared as 0.2 g of phytase added to 9.8 g of fine ground SBM

TABLE 20.2

Treatments identification

| Diet | Treatment ID | Phytase[1] (FTU/kg of feed) | Xylanase |
|---|---|---|---|
| Control | 1 | 500 FTU | 0 |
| Control + FveXyn4 | 2 | 500 FTU | 1250 U/kg |
| Control + Commercial xylanase [2] | 3 | 500 FTU | 50 ppm |

[1] Phytase from Danisco Animal Nutrition
[2] Econase XT ® from AB Vista

Upon arrival at the research facility, chicks are weighed, grouped into 4 blocks by blocks, and randomly allocated to 4 dietary groups in each block with 8 birds per cage in a randomized complete block design. The chicks are fed experimental diets (mash) ad libitum from d 1 and are also allowed ad libitum access to clean drinking water. Excreta are collected twice daily on d 19, 20, and 21 post-hatch. During collection, waxed paper is placed in trays under the cages and excreta on the waxed paper are collected. The collected excreta samples are pooled per cage over the 3 d, stored in a freezer, dried, and ground to pass through a 0.5-mm screen using a mill grinder (Retsch Z M 100, GmbH & Co. K. C., Haan, Germany).

Excreta and diet samples are analyzed for gross energy, dry matter, fat and neutral detergent fibre using standard procedures (AOAC, 2005) for calculation of apparent retentions and AME. Data were subsequently subjected to GLM procedures of SAS.

20.2 Results and Discussion

Birds fed FveXyn4 retain more fat and fibre and subsequently extracted more energy (~57 kcal/kg) compared with the control fed birds (Table 6). Furthermore, FveXyn4 fed birds have significantly higher fibre retention compared to the commercial xylanase.

TABLE 20.3

Effect of new xylanase on apparent nutrients and fibre retention (%) and energy utilization (kcal/kg) in broiler chickens fed corn-corn DDGS based diets

| | Dry matter | Crude protein | Fat | Neutral detergent fibre | Energy |
|---|---|---|---|---|---|
| Control | 67.5ab | 60.4 | 51.6b | 27.4b | 3107b |
| FveXyn4 | 68.2ab | 60.1 | 57.8a | 30.1a | 3164a |
| Commercial xylanase (Econase ® XT) | 68.8a | 60.5 | 52.2ab | 26.8b | 3156ab |
| SEM | 0.48 | 0.91 | 2.05 | 1.15 | 21.8 |

Within a column, means with different letters are significantly different, (P < 0.05).

Example 21

FveXyn4 in Animal Feed (Poultry)

21.1 Material and Methods

An experiment is conducted to evaluate the efficacy of FveXyn4 on energy and nutrient utilization/retention in broiler chickens fed corn/corn DDGS based diets.

The experiment is approved by an Animal Experimentation Committee and conforms to the protocol required by relevant regulations. The birds are allocated to dietary treatments when they are 14 days old. At day old, the birds are brooded together and receive a commercial corn-soybean meal pre-experimental diet. The experiment is carried out in an environmentally controlled house.

TABLE 21.1

Composition of the basal diet

| Ingredient, % | Level |
|---|---|
| Corn | 54.4 |
| Corn-DDGS | 11.0 |
| Soybean Meal | 28.9 |
| Soybean Oil | 1.00 |
| L-Lysine HCl | 0.43 |
| DL-Methionine | 0.27 |
| L-Threonine | 0.11 |
| Sodium Bicarbonate | 0.20 |
| Salt | 0.22 |
| Limestone (A) | 1.53 |
| MCP (B) | 0.56 |
| Vitamin/Trace minerals premix (C) | 1.00 |
| Titanium dioxide | 0.30 |
| Calculated provisions | 100 |
| Crude protein, % | 21.1 |
| MEP, MJ/kg | 11.5 |
| Calcium, % | 0.89 |
| Available phosphorous | 0.28 |
| Digestible Lysine | 1.15 |
| Digestible Methionine | 0.55 |

The premix provided (unit kg- diets): Vit A 16,000 iu; Vit $D_3$ 3,000 iu; Vit E 75 iu; Vit B·, 3 mg; Vit $B_2$ 10 mg; Vit $B_6$ 3 mg; Vit $B_{12}$ 15 µg; Vit $K_3$ 5 mg; Nicotinic acid 60 mg; Pantothenic acid 14.5 mg; Folic acid 1.5 mg; Biotion 275 µg; Choline chloride 250 mg; Iron 20mg; Copper 10 mg; Manganese 100 mg; Cobalt 1 mg; Zinc 82 mg; Iodine 1 mg; Selenium 0.2 mg; Molybdenum 0.5 mg.

TABLE 21.2

Treatments identification

| Diet | Treatment ID | Phytase[1] (FTU/kg of feed) | Xylanase |
|---|---|---|---|
| Control | 1 | 500 FTU | 0 |
| Control + FveXyn4 | 2 | 500 FTU | 1250 U/kg |
| Control + Commercial xylanase[2] | 4 | 500 FTU | 50 ppm |

[1]Phytase from Danisco Animal Nutrition
[2]Econase XT ® from AB Vista

A corn-based basal diet (Table 21.1) is formulated to meet the nutrient requirements of the broiler chicken. From the basal diet, four experimental diets are developed to constitute control, FveXyn4 and commercial xylanase as identified in Table 21.2. One-hundred and ninety-two 14-d old birds are wing tagged and allocated to 4 treatments, with 8 replicate cages per treatment and 6 birds per replicate cage. The experimental design is a randomized complete block with blocks randomly allocated to spaces within a room. Birds are fed experimental diets from day 14 to day 21. Water from the mains is provided to the birds ad libitum. The total excreta voided are collected on days 19 to 21. This enables calculation of apparent total tract retention using total collection. The excreta are dried in forced air oven prior to chemical analyses. The diets and excreta are chemically analyzed. Dry matter (DM) is determined by drying in a force draft oven at 100° C. for 24 hours. The crude fat is determined using Soxhlet extractor system (AOAC 920.39). Nitrogen content is determined by combustion method using a Leco system (Sweeney, 1998). Titanium is determined using the method of Short et al. (1996). Gross energy is determined in an adiabatic calorimeter. Data are subsequently subjected to GLM procedures of SAS.

21.2 Results and Discussion

Compared with the control, FveXyn4 increases (P<0.05) retention of dry matter, crude protein and fat (Table 21.3) in a corn-corn DDGS based diet. Furthermore, FveXyn4 has higher retention of dry matter, protein and fat relative to commercially available feed xylanase. This demonstrates the efficaciousness of FveXyn4 in mitigating the negative effects of the insoluble and soluble fibrous fractions in corn grain and corn-co-products. Indeed, addition of FveXyn4 in the control diet results in significant energy uplift of 116 kcal/kg

TABLE 21.3

Effect of new xylanase on apparent nutrients and fibre retention (%) and energy utilization (kcal/kg) in broiler chickens fed corn-corn DDGS based diets

| | Dry matter | Crude protein | Fat | Energy |
|---|---|---|---|---|
| Control | 73.5bc | 69.2ab | 76.1b | 3431b |
| FveXyn4 | 76.1a | 72.2a | 79.6a | 3547a |
| Commercial xylanase (Econase ® XT) | 72.7c | 66.2b | 78.9ab | 3428b |
| SEM | 0.70 | 1.32 | 1.12 | 30.6 |

Within a column, means with different letters are significantly different, (P < 0.05).

Example 22

FveXyn4 in Animal Feed (Poultry)

22.1 Materials and Methods

An experiment is conducted to evaluate dose response efficacy of FveXyn4 on growth performance of broiler chickens fed corn/corn DDGS based diets and wheat/wheat bran based diets. The experimental procedures are approved by the Institutional Animal Ethics Committee and, comply with the relevant welfare guidelines of the Country. A two-phase feeding programme (starter and finisher) is used (Table 22.1). The starter and finisher diets are offered from d 0 to 21 and 22 to 42, respectively.

TABLE 22.1

Composition of the basal diets[1]

|  | Starter, d 0-21 | | Finisher, d 22-42 | |
| --- | --- | --- | --- | --- |
|  | Corn | Wheat | Corn | Wheat |
| Corn | 57.39 | — | 58.50 | — |
| Corn DDGS | 11.00 | — | 15.00 | — |
| Wheat | — | 60.17 | — | 63.30 |
| Wheat bran | — | 9.00 | — | 13.00 |
| Soybean meal, 45% | 26.50 | 22.34 | 19.00 | 14.00 |
| Tallow | 1.75 | 4.85 | 3.20 | 5.95 |
| Vitamin-mineral premix[2] | 0.33 | 0.33 | 0.33 | 0.33 |
| Sodium bicarbonate | 0.20 | 0.22 | 0.20 | 0.29 |
| Salt | 0.38 | 0.38 | 0.34 | 0.35 |
| Monocalcium Phosphate | 0.35 | 0.37 | 0.13 | 0.20 |
| Limestone | 1.700 | 1.69 | 1.70 | 1.65 |
| L-Lysine HCl | 0.135 | 0.25 | 0.20 | 0.34 |
| DL-methionine | 0.185 | 0.23 | 0.13 | 0.19 |
| L-threonine | 0.100 | 0.19 | 0.09 | 0.22 |
| Calculated provisions | | | | |
| Crude protein | 21.0 | 21.1 | 18.6 | 18.2 |
| ME (MJ/kg) | 12.5 | 12.2 | 12.9 | 12.5 |
| Calcium | 0.81 | 0.80 | 0.75 | 0.73 |
| Available phosphorous | 0.25 | 0.25 | 0.21 | 0.21 |
| Sodium | 0.23 | 0.22 | 0.23 | 0.22 |
| Digestible Lysine | 1.01 | 0.99 | 0.90 | 0.87 |
| Digestible Methionine | 0.47 | 0.47 | 0.39 | 0.39 |
| Digestible Threonine | 0.74 | 0.74 | 0.64 | 0.66 |
| Digestible Tryptophan | 0.19 | 0.21 | 0.16 | 0.17 |

[1]Phytase B top dressed to supply 500 FTU/kg of final feed
[2]Supplied per kilogram of diet: antioxidant, 100 mg; biotin, 0.2 mg; calcium pantothenate, 12.8 mg; cholecalciferol, 60 µg; cyanocobalamin, 0.017 mg; folic acid, 5.2 mg; menadione, 4 mg; niacin, 35 mg; pyridoxine, 10 mg; trans-retinol, 3.33 mg; riboflavin, 12 mg; thiamine, 3.0 mg; dl-a-tocopheryl acetate, 60 mg; choline chloride, 638 mg; Co, 0.3 mg; Cu, 3.0 mg; Fe, 25 mg; I, 1 mg; Mn, 125 mg; Mo, 0.5 mg; Se, 200 µg; Zn, 60 mg.

Two basal diets, one based on wheat/wheat bran and soybean meal, and the other based on corn/corn DDGS and soybean meal, are formulated to meet or exceed the recommended requirements for nutrients, except AME, for broilers (Table 22.1). From each basal diet, three experimental diets are developed to constitute control, 3 doses of FveXyn4 and commercial xylanase as identified in Table 22.2.

TABLE 22.2

Treatments identification

| Diet | Treatment ID | Phytase (FTU/kg of feed) | Xylanase |
| --- | --- | --- | --- |
| Control | 1 | 500 FTU | 0 |
| Control + FveXyn4-dose 1 | 2 | 500 FTU | 1250 U/kg |
| Control + FveXyn4-dose 2 | 3 | 500 FTU | 2500 U/kg |
| Control + FveXyn4-dose 3 | 4 | 500 FTU | 5000 U/kg |
| Control + Commercial xylanase1 | 5 | 500 FTU | 100 ppm |

1AB Vista

Male broiler (Ross 308) chicks are obtained as day-olds from a commercial hatchery. The chicks are individually weighed and allocated to 60 brooder cages (8 chicks per cage) and the 10 dietary treatments randomly assigned to six cages each. On day 12, the birds are transferred to grower cages. The space allocation per bird in brooder and grower cages is 530 and 640 cm$^2$, respectively. The brooder and grower cages are housed in environmentally controlled rooms. The temperature is maintained at 31° C. in the first week and then gradually reduced to 22° C. by the end of third week. The birds receive 20 hours fluorescent illumination and, allowed free access to the diets and water. Body weights and feed intake are recorded at weekly intervals throughout the 42-day experimental period. Mortality is recorded daily. Any bird that die is weighed and the weight is used to adjust FCR. Feed conversion ratios are calculated by dividing total feed intake by weight gain of live plus dead birds. Data are analysed as a two-way factorial arrangement of treatments using the General Linear Models procedure of SAS (2004).

22.2 Results and Discussion

Compared with the control and commercial xylanase, FveXyn4 improves feed conversion efficiency in a dose dependent manner in both corn and wheat based diets (Table 22.3). These observations suggested more value of the xylanase is derived at higher inclusion rate. This demonstrates the efficaciousness of FveXyn4 in mitigating the negative effects of the insoluble and soluble fibrous fractions in cereal ingredients that may limit poultry ability to utilize dietary nutrients to support growth performance.

TABLE 22.3

Dose response effect of new xylanase on growth performance of broiler chickens fed corn-corn DDGS and wheat/wheat bran based diets

| Treatments | | Initial body weight, g | Final body weight, g | Feed intake, g | Body weight gain, g | Feed conversion ratio, g/g |
| --- | --- | --- | --- | --- | --- | --- |
| Grain | Xylanase | | | | | |
| Corn | Control | 33.50 | 2569 | 4162 | 2536 | 1.726 |
| Corn | FveXyn4-Dose1 | 33.54 | 2584 | 4335 | 2551 | 1.708 |

TABLE 22.3-continued

Dose response effect of new xylanase on growth performance of broiler chickens fed corn-corn DDGS and wheat/wheat bran based diets

| Treatments | | Initial body weight, g | Final body weight, g | Feed intake, g | Body weight gain, g | Feed conversion ratio, g/g |
|---|---|---|---|---|---|---|
| Corn | FveXyn4-dose2 | 33.65 | 2585 | 4224 | 2552 | 1.671 |
| Corn | FveXyn4-Dose3 | 33.54 | 2580 | 4177 | 2546 | 1.683 |
| Corn | Commercial xylanase | 33.98 | 2646 | 4295 | 2612 | 1.677 |
| Wheat | Control | 33.56 | 2508 | 4456 | 2474 | 1.824 |
| Wheat | FveXyn4-Dose1 | 33.98 | 2485 | 4285 | 2451 | 1.814 |
| Wheat | FveXyn4-dose2 | 33.63 | 2674 | 4413 | 2641 | 1.656 |
| Wheat | FveXyn4-Dose3 | 33.81 | 2707 | 4330 | 2673 | 1.629 |
| Wheat | Commercial xylanase | 34.13 | 2590 | 4297 | 2556 | 1.694 |
| SEM | | 0.22 | 55.2 | 56.6 | 91.3 | 56.5 |
| Main effects, grains | | | | | | |
| Corn | | 33.64 | 2593 | 4238b | 2559 | 1.693 |
| Wheat | | 33.82 | 2593 | 4356a | 2559 | 1.723 |
| SEM | | 0.10 | 25.30 | 40.82 | 25.28 | 0.018 |
| Main effects, xylanases | | | | | | |
| Control | | 33.53 | 2539 | 4309 | 2505 | 1.775a |
| FveXyn4-Dose1 | | 33.76 | 2535 | 4310 | 2501 | 1.761ab |
| FveXyn4-Dose2 | | 33.64 | 2630 | 4318 | 2596 | 1.664c |
| FveXyn4-Dose3 | | 33.68 | 2643 | 4254 | 2610 | 1.656c |
| Commercial xylanase | | 34.05 | 2618 | 4296 | 2584 | 1.686bc |
| SEM | | 0.152 | 40.00 | 64.55 | 39.98 | 0.028 |
| Probabilities | | | | | | |
| Grain | | — | 0.993 | 0.046 | 0.989 | 0.237 |
| Xylanase | | — | 0.165 | 0.958 | 0.166 | 0.008 |
| Grain and xylanase interaction | | — | 0.190 | 0.329 | 0.189 | 0.212 |

Within a column, means with different letters are significantly different, (P < 0.05)

Example 23

FveXyn4 in Combination with Protease

The effect of FveXyn4 in combination with protease was investigated on the solubilization of pentosan and protein from prepared insoluble DDGS

23.1 Materials and Methods

Enzyme Samples

The xylanase used in this study is a new GH10 xylanase from *Fusarium verticilloides* (designated FveXyn4) expressed in *Trichoderma reesei*, wherein the xylanase was used in purified form—this enzyme may be referred to herein as FveXyn4.

The protease used in this study is the Multifect P-3000 product (available from Danisco Animal Nutrition). The preparation of protease was performed just prior to loadings. Proper amount of stock solution was diluted in cooled MQ-water and mixed while kept on ice. One protease unit (U) was defined as the release of 1.0 µg of phenolic compound (expressed as tyrosine equivalents) from a casein substrate per minute.

Substrate Preparation

For the preparation of insoluble DDGS substrate, removal of soluble non-starch polysaccharides (S-NSP) was performed according to Bach Knudsen (Bach Knudsen, K. E., Carbohydrate and lignin contents of plant materials used in animal feeding. *Animal Feed Science and Technology* 1997, 67, 319-338); Milled DDGS (<212 µm) and acetate/CaCl$_2$-buffer (0.1 M/20 mM, pH 5.0) was added together with thermostable a-amylase (E-BLAAM 53.7 U/mg, Megazyme International) and incubated for 1 h at 100° C. with frequent mixing. Complete degradation of starch was done by incubation with amyloglucosidase (E-AMGDF 36 U/mg, Megazyme International) for 2 h at 60° C. After removal of the starch, the S-NSP was extracted by a phosphate buffer (0.2 M, pH 7.0) and placed at 100° C. for 1 h, followed by centrifugation. The pellet was then thoroughly washed with phosphate buffer, ethanol (85% v/v), and finally acetone, with centrifugation and discard of supernatant in between washes. The sample was placed at room temperature until completely dry.

Procedure

FveXyn4 alone or in combination with protease was investigated on the solubilization of pentosan and protein of prepared insoluble DDGS. 87.5 mg of the prepared insoluble DDGS substrate was weighed into 1.5 ml eppendorf tubes and mixed with citrate buffer (25 mM, pH 6), xylanase (217 mg/kg substrate and 206 mg/kg substrate for corn- and wheat DDGS, respectively), and protease (8.6×10$^5$ U/kg substrate) to a final reaction volume of 1.0 ml. The incubations were carried out at 4 h, 39° C. and 1300 rpm by use of Eppendorf ThermoMixer incubator (Eppendorf). After incubation, samples were filtered and analyzed for soluble pentosan and -protein content, as described below. Reactions were performed in duplicates.

Protein Quantification

Soluble protein was quantified using the BCA (bicinchoninic acid) Protein Assay Kit from Pierce. The samples were prepared in microtiter plates (25 µl/well) and incubated with 200 µl premixed assay reagent for 30 minutes at 37° C., 1100 rpm. The absorbance was measured spectrophotometrically at 562 nm against a 0-2000 µg/ml Bovine Serum Albumin (BSA) standard, as described in the manual. Values were corrected for the amount of added enzymes.

Quantification of C5 Sugars (Pentosans)

The total amount of pentoses brought into solution was measured using the method of Rouau and Surget (1994, A rapid semi-automated method of the determination of total and water-extractable pentosan in wheat flours. Carbohydrate Polymers, 24, 123-32) with a continuous flow injection apparatus (FIG. 7). The supernatants were treated with acid to hydrolyse polysaccharides to monosugars. Phloroglucinol (1,3,5-trihydroxybenzen) was added for reaction with monopentoses and monohexoses, which forms a coloured complex.

By measuring the difference in absorbance at 550 nm compared to 510 mu, the amount of pentoses in the solution was calculated using a standard curve. Unlike the pentose-phloroglucinol complex, the absorbance of the hexose-phloroglucinol complex is constant at these wavelengths. Glucose was added to the phloroglucinol solution to create a constant glucose signal and further ensure no interference from hexose sugars.

Statistical Analysis

A one-way ANOVA was applied on the experimental data for comparison of treatments on both the solubilization of pentosan and protein, with pairwise comparisons performed by Holm-Sidak method, using SigmaPlot 12.0 (SyStat Software Inc.). Overall significance level at P=0.05.

23.2 Results and Discussion

Pentosan and protein solubilization was measured by incubation of insoluble corn and wheat DDGS with xylanase and protease alone and in combination.

Figure 27:
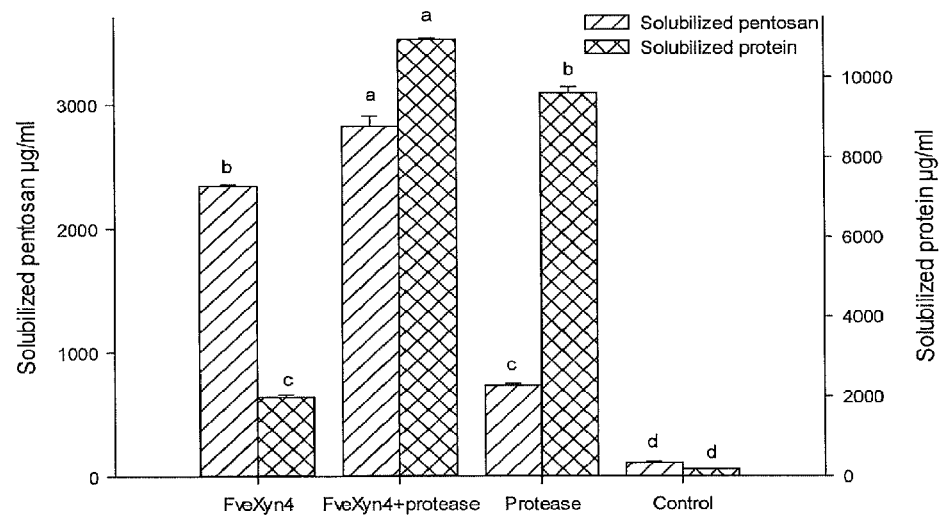
FIG. 27 shows the effect of the xylanase and protease treatments alone and in combination on the solubilization of pentosan and protein from insoluble corn DDGS. Letters a-d are significant different according to on-way ANOVA and Holm-Sidak comparisons with overall significance level at $P=0.05$. Error bars indicate S.D.
Figure 28:
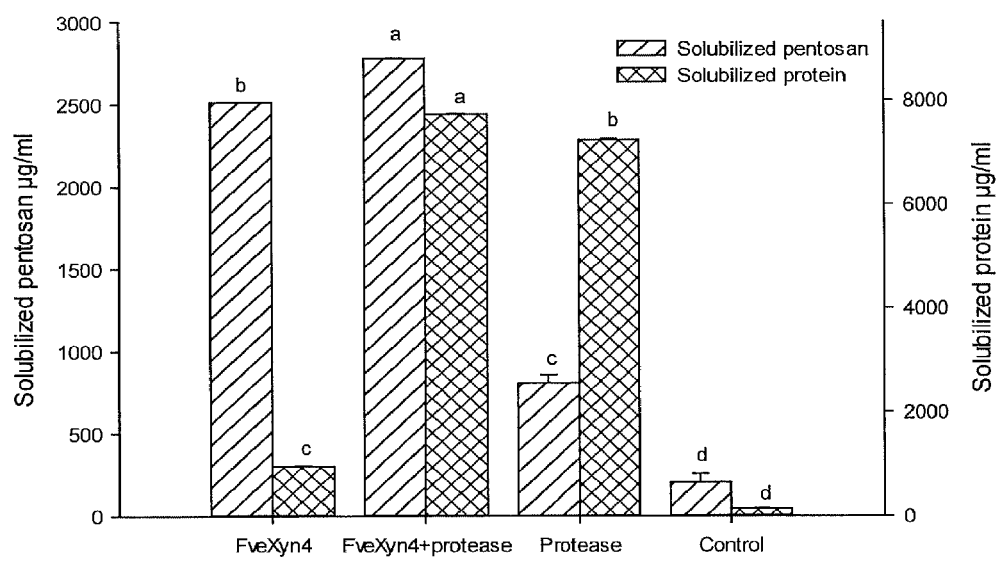
FIG. 28 shows the effect of the xylanase and protease treatments alone and in combination on the solubilization of pentosan and protein from insoluble wheat DDGS. Letters a-d are significant different according to on-way ANOVA and Holm-Sidak comparisons with overall significance level at $P=0.05$. Error bars indicate S.D.

The results are shown in FIG. 27 (insoluble corn DDGS) and in FIG. 28 (insoluble wheat DDGS).

FIG. 27 shows the effect of the xylanase and protease treatments alone and in combination on the solubilization of pentosan and protein from insoluble corn DDGS. Letters a-d are significant different according to on-way ANOVA and Holm-Sidak comparisons with overall significance level at P=0.05. Error bars indicate S.D.

FIG. 28 shows the effect of the xylanase and protease treatments alone and in combination on the solubilization of pentosan and protein from insoluble wheat DDGS. Letters a-d are significant different according to on-way ANOVA and Holm-Sidak comparisons with overall significance level at P=0.05. Error bars indicate S.D.

When compared to the effects of xylanase treatment by itself, the combination of xylanase and protease further increased the solubilization of protein from both corn and wheat DDGS. More interestingly, addition of protease also significantly increased the solubilization of pentosan from both corn and wheat DDGS, indicating a synergistic effect where addition of protease increase the accessibility of the xylanase towards the substrate by opening up the feed matrix structure through protein degradation. Furthermore, xylanase by itself and in combination with protease also increase the solubilization of protein as compared to control and protease alone, respectively. This further supports the theory of a synergistic effect between xylanase and protease.

Example 24

Comparison of FveXyn4 and FoxXyn2 in Pentosan Solubilisation (Breakdown or Solubilisation of Insoluble Arabinoxylan (AXinsol))

The ability to solubilize insoluble arabinoxylan from corn DDGS was used as one of the key selection criteria and in this experiment the ability to solubilise arabinoxylan from corn DDGS is compared for the two xylanases of the present invention (FveXyn4 and FoxXyn2).

The two xylanases showed strong and equal performance on pentosan solubilisation from corn DDGS, indicating equal performance of these homologous xylanases on solubilisation of arabinoxylan from fibrous by-products.

24.1 Materials and Methods

Enzyme Samples

The xylanases used in this study are:

A GH10 xylanase from *Fusarium verticilloides* (designated FveXyn4) expressed in *Trichoderma reesei*, wherein the xylanase was used in purified form—this enzyme may be referred to herein as FveXyn4, and a GH10 xylanase from *Fusarium oxysporum* (designated FoxXyn2) expressed in *Trichoderma reesei*, wherein the xylanase was used in purified form—this enzyme may be referred to herein as FoxXyn2.

Feed Raw Materials

The feed used in this experiments is corn DDGS.

Pentosan Solubilisation (AXinsol Solubilisation)

The method used for pentosan solubilisation was: 100 mg of feed raw material was transferred to a 2 ml Eppendorf centrifuge tube and the precise weight recorded. 750 µL incubation buffer (200 mM HEPES, 100 mM NaCl, 2 mM CaCl, pH 6.0) and 900 µl chloramphenicol solution (40 µg/ml in incubation buffer) was added. Enzyme of choice was added to make a total volume of 1.8 mL.

Each sample was assayed in doublets and in parallel with a blank (incubation without exogenously added enzyme). The samples were incubated on an Eppendorf thermomixer at 40° C. with shaking. After 2 or 18 hours of incubation the supernatant was filtered using 96 wells filterplates (Pall Corporation, AcroPrep 96 Filter Plate, 1.0 µm Glass, NTRL, 1 mL well). After filtration the samples were stored at 4° C. until analysis for total amount of C5 sugars, arabinose and xylose.

Quantification of C5 Sugars (Pentosans)

The total amount of pentoses brought into solution was measured using the method of Rouau and Surget (1994. A rapid semi-automated method of the determination of total and water-extractable pentosan in wheat flours. Carbohydrate Polymers, 24, 123-32) with a continuous flow injection apparatus (FIG. 7). The supernatants were treated with acid to hydrolyse polysaccharides to monosugars. Phloroglucinol (1,3,5-trihydroxybenzen) was added for reaction with monopentoses and monohexoses, which forms a coloured complex. By measuring the difference in absorbance at 550 nm compared to 510 nm, the amount of pentoses in the solution was calculated using a standard curve. Unlike the pentose-phloroglucinol complex, the absorbance of the hexose-phloroglucinol complex is constant at these wavelengths.

Glucose was added to the phloroglucinol solution to create a constant glucose signal and further ensure no interference from hexose sugars.

24.2 Result and Discussion

Pentosan solubilisation was monitored in a dose response setup using fibrous by-product of corn (namely cDDGS).

Figure 29:
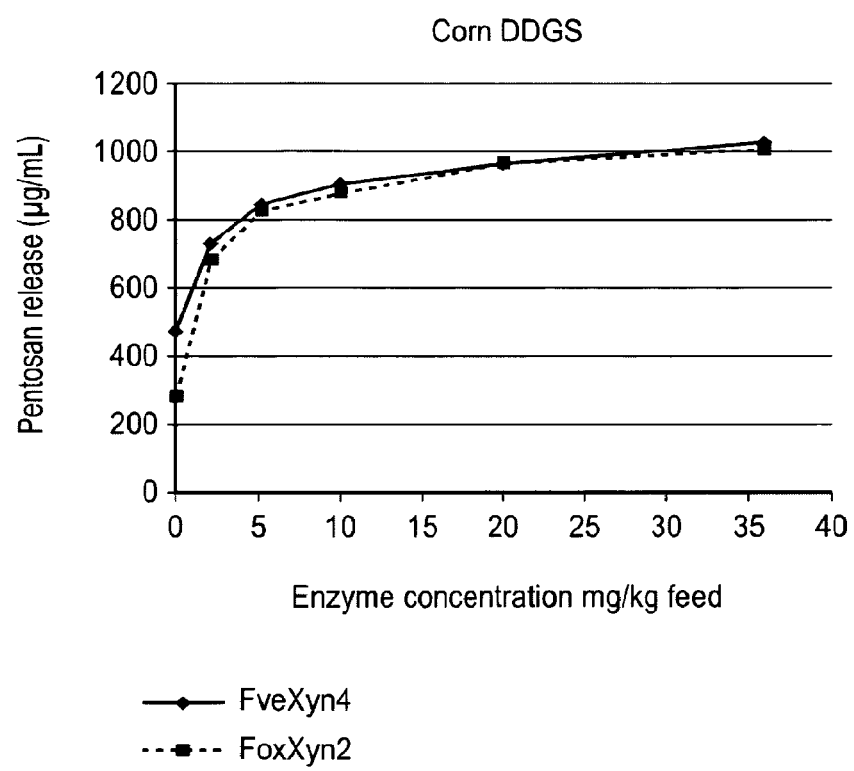
FIG. 29 shows solubilisation of pentosans from cDDGS as a function of xylanase dosage. The xylanases used were the xylanases of the present invention (FveXyn4 and FoxXyn2).

The results comparing the two xylanases of the present invention (FveXyn4 and FoxXyn2) are shown in FIG. 29 (in corn DDGS).

FIG. 29 shows solubilisation of pentosans from cDDGS as a function of xylanase dosage. The xylanases used were the xylanases of the present invention (FveXyn4 and FoxXyn2).

Both xylanases performs well on corn and are equally good a breaking down AXinsol (e.g. solubilising pentosans) in corn based substrates which clearly indicates that these two homologous xylanases perform equal on solubilisation of arabinoxylan from fibrous by-products.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

---

The invention claimed is:

1. A method for degrading arabinoxylan-containing material in a xylan-containing material, comprising admixing said xylan-containing material with a xylanase comprising a polypeptide sequence shown herein as SEQ ID No. 3, SEQ ID No. 2, or SEQ ID No. 1; or a variant thereof having at least 99.5% identity with SEQ ID No. 3, SEQ ID No. 2, or SEQ ID No. 1.

2. The method according to claim 1 wherein the arabinoxylan is insoluble arabinoxylan (AXinsol).

3. The method according to claim 1 wherein the xylan-containing material is selected from one or more of the group consisting of: a feed or feedstuff; a feed component; a grain-based material; a mash; a wort; a malt; malted barley; an adjunct, a barley mash; and a cereal flour.

4. The method according to claim 1 wherein the arabinoxylans are solubilized without increasing viscosity in the reaction medium.

5. The method or use according to claim 3 wherein the grain-based material comprises or consists of corn, distillers dried grain solubles (DDGS), wheat, wheat bran or a combination thereof.

6. The method or use according to claim 5 wherein the grain-based material is a corn-based material.

7. The method according to claim 1 wherein the xylanase is used in combination with one or more of the enzymes selected from the group consisting of a protease and an amylase.

8. The method of claim 1, wherein the method is or is part of a wheat gluten-starch separation process.

9. The method of claim 1, wherein the method is or is part of a biofuel or biochemical production process.

10. The method of claim 9, wherein the biofuel is bioethanol.

11. The method of claim 7, wherein the amylase is one or more of an α-amylase (E.C. 3.2.1.1), a G4-forming amylase (E.C. 3.2.1.60), a β-amylase (E.C. 3.2.1.2) or a γ-amylase (E.C. 3.2.1.3).

12. The method of claim 5, wherein the DDGS comprises corn-based distillers dried drain solubles (cDDGS).

\* \* \* \* \*